United States Patent
Nirogi et al.

(10) Patent No.: US 9,951,045 B2
(45) Date of Patent: Apr. 24, 2018

(54) INDAZOLE COMPOUNDS AS 5-HT$_4$ RECEPTOR AGONISTS

(71) Applicant: SUVEN LIFE SCIENCES LIMITED, Hyderabad, Andhra Pradesh (IN)

(72) Inventors: Ramakrishna Nirogi, Hyderabad (IN); Abdul Rasheed Mohammed, Hyderabad (IN); Anil Karbhari Shinde, Hyderabad (IN); Shankar Reddy Gagginapally, Hyderabad (IN); Venkateswarlu Jasti, Hyderabad (IN)

(73) Assignee: SUVEN LIFE SCIENCES LIMITED, Hyderabad, Andhra (IN)

( * ) Notice: Subject to any disclaimer, the term of this patent is extended or adjusted under 35 U.S.C. 154(b) by 0 days.

(21) Appl. No.: 15/104,521

(22) PCT Filed: Feb. 24, 2014

(86) PCT No.: PCT/IN2014/000116
§ 371 (c)(1),
(2) Date: Jun. 14, 2016

(87) PCT Pub. No.: WO2015/092804
PCT Pub. Date: Jun. 25, 2015

(65) Prior Publication Data
US 2016/0311797 A1    Oct. 27, 2016

(30) Foreign Application Priority Data
Dec. 16, 2013  (IN) ............................ 5852/CHE/2013

(51) Int. Cl.
*C07D 401/12* (2006.01)
*C07D 405/14* (2006.01)
*C07D 413/12* (2006.01)
*C07D 413/14* (2006.01)
*C07D 403/12* (2006.01)

(52) U.S. Cl.
CPC ......... *C07D 401/12* (2013.01); *C07D 403/12* (2013.01); *C07D 405/14* (2013.01); *C07D 413/12* (2013.01); *C07D 413/14* (2013.01)

(58) Field of Classification Search
CPC .. C07D 401/12; C07D 403/12; C07D 405/14; C07D 413/12; C07D 413/14
See application file for complete search history.

(56) References Cited

FOREIGN PATENT DOCUMENTS

| WO | 2005/061483 | 7/2005 |
|---|---|---|
| WO | 2011/099305 | 8/2011 |
| WO | 2013/042135 | 3/2013 |

OTHER PUBLICATIONS

Guido Furlotti, Maria Alessandra Alisi, Claudia Apicella, Alessandra Capezzone de Joannon, Nicola Cazzolla, Roberta Costi, Giuliana Cuzzucoli Crucitti, Beatrice Garrone, Alberto Iacovo, Gabriele Magarò, Giorgina Mangano, Gaetano Miele, Roselle Ombrato, Luca Pescatori, Lorenzo Polenzani, Federica Rosi, Marco Vitiello, and Roberto Di Santo, Discover.*
European Patent Office, "International Search Report", dated Aug. 4, 2014 in PCT Application No. PCT/IN2014/000116, filed Feb. 24, 2014.
European Patent Office, "Written Opinion", dated Aug. 4, 2014 in PCT Application No. PCT/IN2014/000116, filed Feb. 24, 2014.
Johnson et al., "The 5-Hydroxytryptamine4 Receptor Agonists Prucalopride and PRX-03140 Increase Acetylcholine and Histamine Levels in the Rat Prefrontal Cortex and the Power of Stimulated Hippocampal θ Oscillations" Journal Pharmacol. Exper. Ther. 341(3):681-691 (2012).
Lucas et al., "Serotonin4 (5-HT4) Receptor Agonists are Putative Antidepressants with a Rapid Onset of Action" Neuron 55:712-725 (2007).
Epix Pharmaceuticals, "Lead Product Candidate—PRX-03140", www.epixpharma.com, Jul. 17, 2008.
Marchetti-Gauthier et al., "BIMU1 Increases Associative Memory in Rats by Activating 5-HT4 Receptors" Neuropharmacology, 1997, 36, 4(5), 697-706.
Nirogi et al., "Synthesis of GR 125487, a selective 5-HT4 receptor antagonist" Synthetic Communications, 2016, 46, 12, 1036-1043.

* cited by examiner

*Primary Examiner* — Sarah Pihonak
*Assistant Examiner* — Jason Deck
(74) *Attorney, Agent, or Firm* — IPHorgan Ltd.

(57) ABSTRACT

The present invention relates to novel indazole compounds of the Formula (I), wherein, R$_1$ is alkyl or cycloalkyl; (Formula II) including their stereoisomers and their pharmaceutically acceptable salts. This invention also relates to methods of making such compounds and pharmaceutical compositions comprising such compounds. The compounds of this invention are useful in the treatment of various disorders that are related to 5-Hydroxy-tryptamine 4 (5-HT$_4$) receptor agonists.

7 Claims, 1 Drawing Sheet

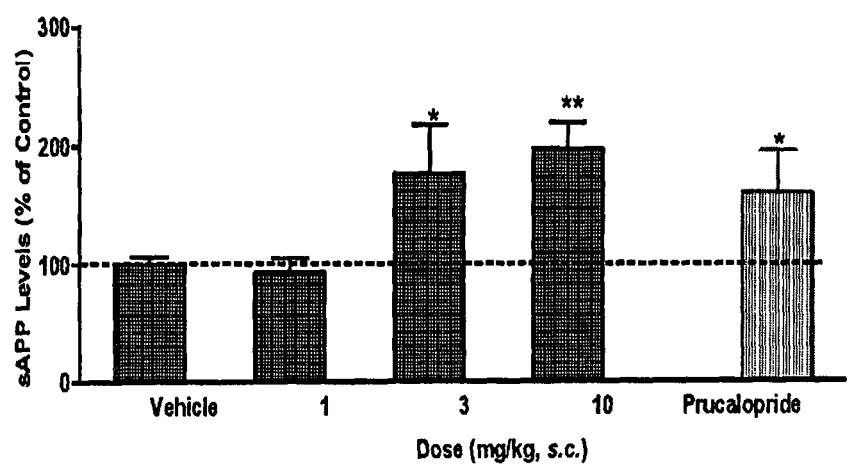

INDAZOLE COMPOUNDS AS 5-HT$_4$ RECEPTOR AGONISTS

CROSS REFERENCE TO RELATED APPLICATIONS

This application is a national stage completion application of PCT Application No. PCT/IN2014/000116, filed Feb. 24, 2014, and claims the benefit of India Application No. 5852/CHE/2013, filed Dec. 16, 2013. Each of these applications is incorporated by reference herein in its entirety.

FIELD OF INVENTION

The present invention relates to novel indazole compounds of the formula (I), stereoisomers thereof and pharmaceutically acceptable salts thereof as 5-Hydroxytryptamine 4 (5-HT$_4$) receptor agonists. The present invention also describes method of making such compounds and pharmaceutical compositions comprising such compounds

BACKGROUND OF THE INVENTION

The 5-HT$_4$ receptor is one of the seven subtypes of 5-Hydroxytryptamine (5-HT) receptors. It is a 7-transmembrane domain protein coupled to a G-protein positively linked to the activation of adenylate cyclase (Molecular Pharmacology, 1990, 37, 408-411). 5-HT$_4$R agonists are found to have potential utility in the treatment of disorders such as Alzheimer's disease, schizpherenia, depression, attention deficit hyperactivity disorder, Huntington's disease, parkinson's disease and several other psychiatric disorders (Behavioral brain research, 1996, 73, 249-252; Neuron, 2007, 55, 712-725; Schizophrenia Bulletin, 2007, 33(5), 1100-1119 and Neuroscience and Medicine, 2011, 2, 87-92). 5-HT$_4$ receptor agonists are known to improve memory in different behavioral experiments in rodents (Neuropharmacology, 1997, 36, 697-706; Journal of Pharmacology and Experimental Therapeutics, 1998, 286, 1115-1121; Journal of Pharmacology and Experimental Therapeutics, 2002, 302, 731-741; Naunyn-Schmiedeberg's Archives of Pharmacology, 2003, 367: 621-628). By injecting 5-HT$_4$ receptor agonist to rats and implanting a recording electrode in the hippocampal CA1 region, Kemp and Manahan-Vaughan (Cerebral Cortex, 2005, 15, 1037-1043) showed that 5-HT$_4$ receptors play a key role in the regulation of synaptic plasticity and the determination of particular properties of stored synaptic information. Autoradiographic studies using the 5-HT$_4$ receptor antagonists [125I]SB207710 and [3H] GR113808 in rat, mouse, guinea pig or post-mortem human brain showed that the 5-HT$_4$ receptor is present at a high density in the limbic system including the hippocampus and frontal cortex (Neuropharmacology 1994, 33, 527-541; European Neuropsychopharmacology, 2003, 13, 228-234) suggesting a role of 5-HT$_4$ receptor in memory and cognition.

The drugs currently available ameliorate late-stage symptoms such as cognitive deficits. No drugs are in the market that specifically targets the cellular mechanisms of Alzheimer's disease (AD), namely the generation of the neurotoxic amyloid β-protein (Aβ) from the amyloid precursor protein (APP). AD is a progressive neurodegenerative disorder characterized by the appearance of senile plaques mainly composed of amyloid β-protein (Aβ), and the development of neurofibrillary tangles in patient's brains (Journal of Neuropathology & Experimental Neurology, 1997, 56, 321-339). AD patients also have cognitive deficits, impaired long-term potentiation (LTP), learning and memory deficits (Neuron, 2004, 44, 181-193) and a consistent deficit in cholinergic neurotransmission. Several acetylcholine esterase inhibitors such as donepezil are available in the market for the treatment of patients with mild-to-moderate AD. However, beneficial effects of this symptomatic treatment can only be maintained for up to 36 months (Pharmacological Research, 2004, 50, 441-451).

Patent publications WO9410174, WO9408994, WO2003035649, WO2004094418, WO2005049608, WO2006090224, WO2011099305, WO2011101774, US20080207690 and US20080269211 disclosed some 5-HT$_4$ receptor compounds. While several 5-HT$_4$ receptor agonists/partial agonists have been disclosed in the literature, no compound, either agonist or partial agonist targeting 5-HT$_4$ receptor is launched in the market until now for the treatment of dementia related disorders. Therefore, there is need and scope to discover new 5-HT$_4$ receptor agonists/partial agonists with novel chemical structures for treatment of disorders that are affected by the 5-HT$_4$ receptor agonists.

SUMMARY OF THE INVENTION

The present invention relates to novel 5-HT$_4$ receptor agonists of formula (I),

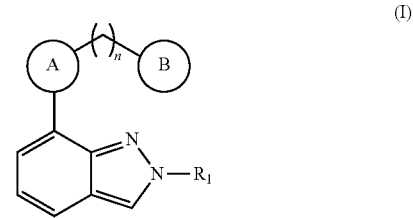

(I)

or their stereoisomers and pharmaceutically acceptable salts thereof,
wherein,
R$_1$ is alkyl or cycloalkyl;

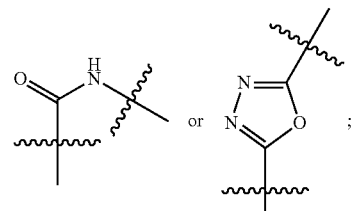

is

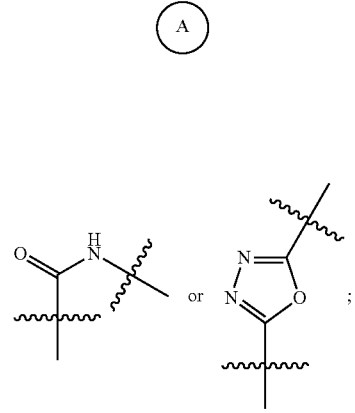

is

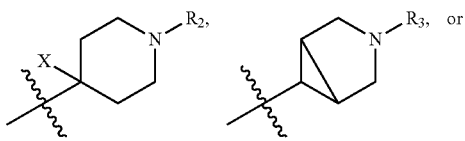

-continued

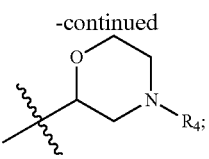

R₂ is alkyl,

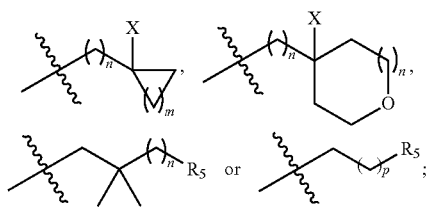

R₃ is alkyl

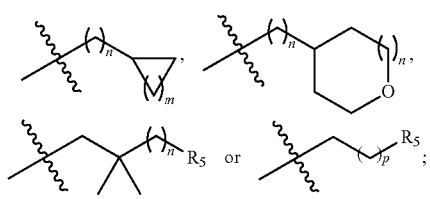

R₄ is

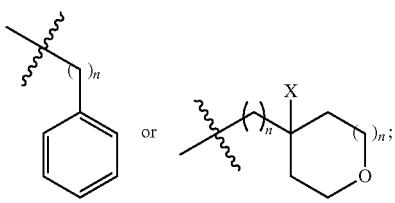

R₅ is fluoro, hydroxy, alkoxy or

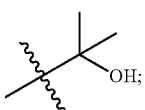 [SMILES: *C(C)(C)O]

X is hydrogen, hydroxy or halogen;
"n" is an integer ranging from 0 to 1, both inclusive;
"m" is an integer ranging from 1 to 4, both inclusive;
"p" is an integer ranging from 0 to 3, both inclusive.

In one aspect, the present invention relates to novel compounds of formula (I), stereoisomers thereof and pharmaceutically acceptable salts thereof as 5-HT₄ receptor agonists. Specifically, the compounds of this invention are useful in the treatment of various disorders such as Alzheimer's disease, schizophrenia, attention deficit hyperactivity disorder, Huntington's disease, Parkinson's disease or psychiatric disorders.

In another aspect, the invention relates to pharmaceutical composition containing a therapeutically effective amount of at least one compound of formula (I), stereoisomers thereof and pharmaceutically acceptable salts thereof.

In still another aspect, the invention relates to method of administering 5-HT₄ receptor agonists in a subject, which comprises administering to the subject a therapeutically effective amount of a compound of formula (I), stereoisomers thereof and pharmaceutically acceptable salts thereof.

In yet another aspect, the invention further relates to the process for preparing compounds of formula (I), stereoisomers thereof and pharmaceutically acceptable salts thereof.

Representative compounds of the present invention include those specified below. The present invention should not be construed to be limited to them.

N—[(N-tetrahydropyran-4-yl methyl) piperidin-4-yl methyl]-2-isopropyl-2H-indazole-7-carboxamide fumarate;

N—[(N-tetrahydropyran-4-yl methyl) piperidin-4-yl methyl]-2-ethyl-2H-indazole-7-carboxamide fumarate;

N—[N-(3-methoxy propyl)-3-aza bicyclo[3.1.0]hexane-6-yl methyl]-2-isopropyl-2H-indazole-7-carboxamide oxalate;

N—[N-(3-methoxy propyl) piperidin-4-ylmethyl]-2-ethyl-2H-indazole-7-carboxamide fumarate;

N—[N-(3-methoxy propyl)-3-aza bicyclo[3.1.0]hexane-6-yl methyl]-2-ethyl-2H-indazole-7-carboxamide oxalate;

N—[N-(3-hydroxy-2,2-dimethyl propyl) piperidin-4-ylmethyl]-2-isopropyl-2H-indazole-7-carboxamide L(+) Tartarate;

N—[N-(2-fluoroethyl) piperidin-4-yl methyl]-2-isopropyl-2H-indazole-7-carboxamide;

N—[N-benzyl morpholin-2-yl methyl]-2-isopropyl-2H-indazole-7-carboxamide fumarate;

N—[(N-tetrahydropyran-4-yl methyl) morpholine-2-yl methyl]-2-isopropyl-2H-indazole-7-carboxamide;

N—[N-(tetrahydropyran-4-yl methyl)-3-aza bicyclo[3.1.0] hexane-6-yl methyl]-2-isopropyl-2H-indazole-7-carboxamide;

N—[N-(1-hydroxy cyclopentylmethyl) piperidin-4-yl methyl]-2-isopropyl-2H-indazole-7-carboxamide L(+) tartarate;

N—[N-(tetrahydropyran-4-yl)-3-aza bicyclo[3.1.0]hexane-6-yl methyl]-2-isopropyl-2H-indazole-7-carboxamide;

N—(N-isopropyl piperidin-4-ylmethyl)-2-isopropyl-2H-indazole-7-carboxamide fumarate;

N—(N-cyclobutyl piperidin-4-yl methyl)-2-isopropyl-2H-indazole-7-carboxamide fumarate;

N—(N-cyclohexyl piperidin-4-yl methyl)-2-isopropyl-2H-indazole-7-carboxamide fumarate;

N—(N-isopropyl-3-aza bicyclo[3.1.0]hexane-6-yl methyl)-2-isopropyl-2H-indazole-7-carboxamide fumarate;

N—[N-(4-hydroxy tetrahydro pyran-4-yl methyl) piperidin-4-yl methyl]-2-isopropyl-2H-indazole-7-carboxamide fumarate;

N—[N-(tetrahydro pyran-4-yl)-3-aza bicyclo[3.1.0]hexane-6-yl methyl]-2-ethyl-2H-indazole-7-carboxamide oxalate;

N—(N-isopropyl piperidine-4-yl)-2-isopropyl-2H-indazole-7-carboxamide fumarate;

N—(N-cyclopropylmethyl piperidine-4-yl)-2-isopropyl-2H-indazole-7-carboxamide fumarate;

N—(N-cyclobutylmethyl piperidine-4-yl)-2-isopropyl-2H-indazole-7-carboxamide fumarate;

N—[(N-tetrahydropyran-4-yl methyl)-4-fluoro piperidin-4-yl methyl]-2-isopropyl-2H-indazole-7-carboxamide;

N—[(N-tetrahydrofuran-3-yl methyl) piperidin-4-yl methyl]-2-isopropyl-2H-indazole-7-carboxamide N—[N-(3-methoxy propyl) piperidin-4-yl methyl]-2-isopropyl-2H-indazole-7-carboxamide fumarate;

N—[N-(2-methoxy ethyl) piperidin-4-yl methyl]-2-isopropyl-2H-indazole-7-carboxamide fumarate;
N—[(N-tetrahydropyran-4-yl methyl)-4-hydroxy piperidin-4-yl methyl]-2-isopropyl-2H-indazole-7-carboxamide fumarate;
N—[(N-tetrahydropyran-4-yl)-4-hydroxy piperidin-4-yl methyl]-2-isopropyl-2H-indazole-7-carboxamide fumarate;
N—[N-(3-methoxy propyl)-4-hydroxypiperidin-4-yl methyl]-2-isopropyl-2H-indazole-7-carboxamide fumarate;
N—[N-(3-Hydroxy-3-methyl butyl) piperidin-4-yl methyl]-2-isopropyl-2H-indazole-7-carboxamide;
N—[N-(2-hydroxy-2-methyl propyl)-4-hydroxy piperidin-4-ylmethyl]-2-isopropyl-2H-indazole-7-carboxamide oxalate;
N—[N-(4-hydroxy tetrahydropyran-4-yl methyl)-4-fluoro piperidin-4-yl methyl]-2-isopropyl-2H-indazole-7-carboxamide L(+) Tartarate;
N—[N-(2-hydroxy-2-methyl propyl) piperidin-4-yl methyl]-2-isopropyl-2H-indazole-7-carboxamide L(+) Tartarate;
N—[N-(2-Methoxy-2-methyl propyl) piperidin-4-yl methyl]-2-isopropyl-2H-indazole-7-carboxamide;
N—[N-(2-fluoro-2-methyl propyl) piperidin-4-yl methyl]-2-isopropyl-2H-indazole-7-carboxamide L(+) Tartarate;
N—[N-(2-hydroxy-2-methyl propyl)-4-fluoro piperidin-4-ylmethyl]-2-isopropyl-2H-indazole-7-carboxamide L(+) Tartarate;
N—[N-(2-hydroxy-2-methyl propyl)-3-aza bicyclo[3.1.0] hexane-6-yl methyl]-2-isopropyl-2H-indazole-7-carboxamide L(+) Tartarate;
2-Isopropyl-7-{5-[1-(3-methoxy propyl) piperidin-4-yl]-[1,3,4]oxadiazol-2-yl}-2H-indazole fumarate;
2-Isopropyl-7-{5-[1-(tetrahydropyran-4-yl methyl) piperidin-4-yl]-[1,3,4]oxadiazol-2-yl}-2H-indazole fumarate;
2-Isopropyl-7-{5-[1-(tetrahydropyran-4-yl) piperidin-4-yl]-[1,3,4]oxadiazol-2-yl}-2H-indazole fumarate; and
N—[N-(2-hydroxy-2-methyl propyl) piperidin-4-yl methyl]-2-isopropyl-2H-indazole-7-carboxamide Oxalate.

BRIEF DESCRIPTION OF DRAWINGS

FIG. 1: Results of the test compound in comparison with control group.

DETAILED DESCRIPTION OF THE INVENTION

Unless otherwise stated, the following terms used in the specification and claims have the meanings given below:
The term "hydroxy" represents —OH.
The term "halogen" means fluorine, chlorine, bromine or iodine.
The term "alkyl" means straight or branched hydrocarbon chain consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.
The term "alkoxy" means an alkyl group attached via an oxygen linkage to the rest of the molecule. Exemplary "alkoxy" groups include methoxy, ethoxy, propyloxy, iso-propyloxy and the like.

The term "cycloalkyl" means non-aromatic mono or multi cyclic ring systems of 3 to 12 carbon atoms. Exemplary "Cycloalkyl" groups include cyclopropyl, cyclobutyl, cyclopentyl and the like.
The term "agonist" means full agonist or partial agonist.
The phrase "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.
Commercial reagents were utilized without further purification. Room temperature is defined as an ambient temperature range, typically from about 25° C. to about 35° C. Unless otherwise stated, all mass spectra were obtained using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.
The compounds of formula (I) may involve below mentioned embodiments. It is to be understood that the embodiments below are illustrative of the present invention and are not intended to limit the claims to the specific embodiment's exemplified.
One embodiment of formula (I) includes compounds of formula (Ia),

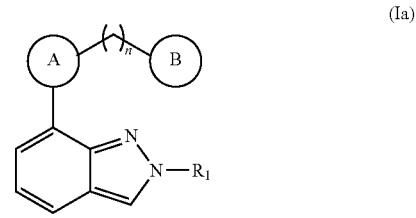

(Ia)

stereoisomers thereof and pharmaceutically acceptable salts thereof,
wherein,
R$_1$ is alkyl or cycloalkyl;

is

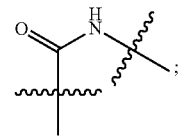

;

-continued

B 

is

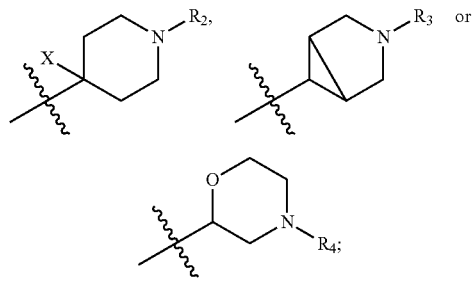

$R_2$ is alkyl,

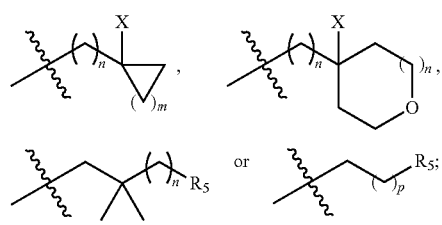

$R_3$ is alkyl,

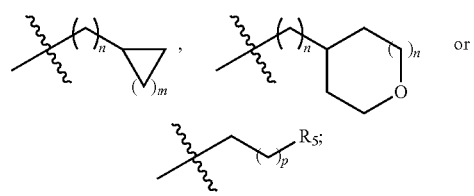

$R_4$ is

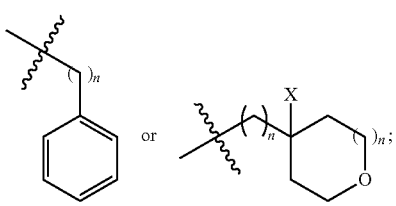

$R_5$ is fluoro, hydroxy or alkoxy;
X is hydrogen, hydroxy or halogen;
"n" is an integer ranging from 0 to 1, both inclusive;
"m" is an integer ranging from 1 to 4, both inclusive;
"p" is an integer ranging from 0 to 3, both inclusive.

Another embodiment of formula (I) includes compounds of formula (Ib),

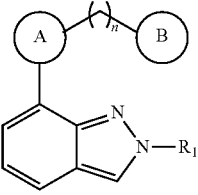 (Ib)

stereoisomers thereof and pharmaceutically acceptable salts thereof,
wherein,
$R_1$ is alkyl or cycloalkyl;

A is

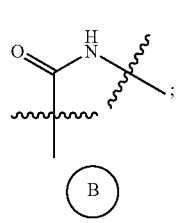

B is

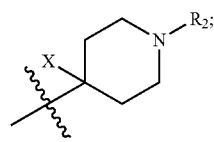

$R_2$ is

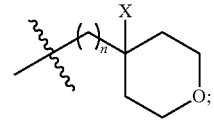

X is hydroxy;
"n" is an integer ranging from 0 to 1, both inclusive.

Another embodiment of formula (I) includes compounds of formula (Ic),

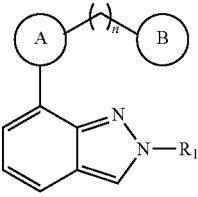 (Ic)

stereoisomers thereof and pharmaceutically acceptable salts thereof,
wherein,
$R_1$ is alkyl;

is

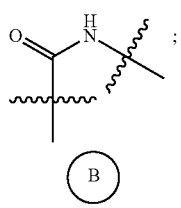

is

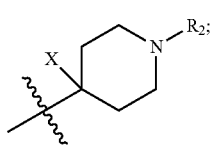

$R_2$ is

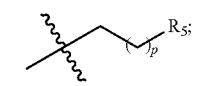

$R_5$ is alkoxy or

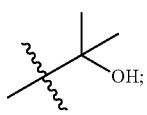 [SMILES: *C(C)(C)O]

X is hydrogen or hydroxy;
"n" is an integer ranging from 0 to 1, both inclusive;
"p" is an integer ranging from 0 to 3, both inclusive.
Another embodiment of formula (I) includes compounds of formula (Id), (Id)

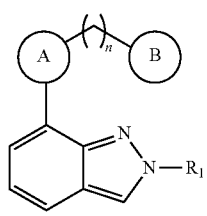

stereoisomers thereof and pharmaceutically acceptable salts thereof,
wherein,
$R_1$ is alkyl;

is

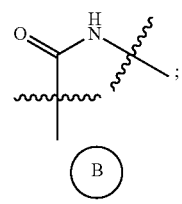

is

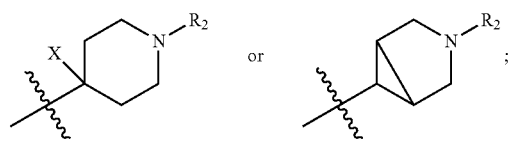

$R_2$ is

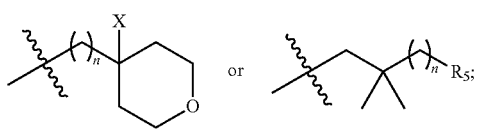

$R_5$ is fluoro, hydroxy or alkoxy;
X is hydrogen, hydroxy or halogen;
"n" is an integer ranging from 0 to 1, both inclusive.
Another embodiment of formula (I) includes compounds of formula (Ie), (Ie)

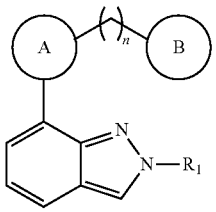

stereoisomers thereof and pharmaceutically acceptable salts thereof,
wherein,
$R_1$ is alkyl;

is

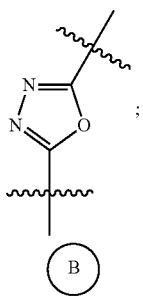

is

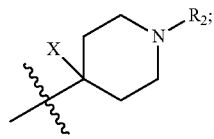

R₂ is alkyl,

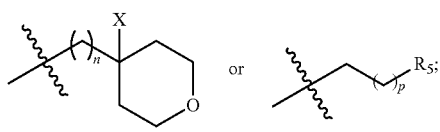

R₅ is alkoxy;
X is hydrogen;
"n" is an integer ranging from 0 to 1, both inclusive;
"p" is an integer ranging from 0 to 3, both inclusive.

Pharmaceutical Compositions

In order to use the compounds of formula (I) stereoisomers thereof and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipient is carrier or diluent. Thus, the active compounds of the invention may be formulated for oral dosing. Such pharmaceutical compositions and processes for preparing same are well known in the art (The Science and Practice of Pharmacy, D. B. Troy, 21$^{st}$ Edition, Williams & Wilkins, 2006).

The dose of the active compounds can vary depending on factors such as age and weight of patient, nature and severity of the disease to be treated and such other factors. Therefore, any reference regarding pharmacologically effective amount of the compounds of general formula (I), stereoisomers thereof and pharmaceutically acceptable salts thereof refers to the aforementioned factors.

Methods of Preparation

The compounds of formula (I) can be prepared by using Schemes I to V as shown below:

Scheme I:

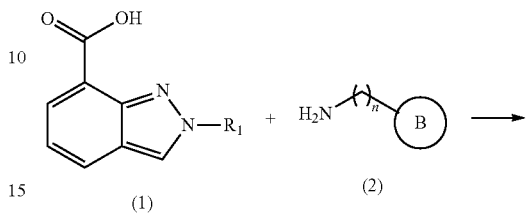

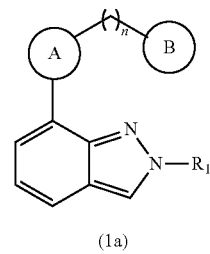

In above Scheme I, all symbols are as defined above. The compounds of formula (Ia) are prepared according to Scheme I.

The compound of formula (1) is coupled with compound of formula (2) by using coupling reagent to form compound of formula (Ia). The reaction is carried out by using coupling agent such as O-(Benzotriazol-1-yl)-N,N,N',N'-tetramethyluronium tetrafluoroborate, carbonyldiimidazole, O-(Benzotriazol-1-yl)-N,N,N',N'-tetramethyluronium hexafluorophosphate, O-(7-Azabenzotriazol-1-yl)-N,N,N',N'-tetramethyluronium hexafluorophosphate, O-(6-Chlorobenzotriazol-1-yl)-N,N,N',N'-8 tetramethyluronium hexafluorophosphate or thionyl chloride and preferably by using O-(Benzotriazol-1-yl)-N,N,N',N'-tetramethyluronium tetrafluoroborate or carbonyldiimidazole. This reaction is carried out in a solvent such as dichloromethane, methanol, tetrahydrofuran, toluene, dimethylformamide, dimethyl sulfoxide, diethyl ether and the like or a mixture thereof and preferably by using dichloromethane. The reaction may be affected in the presence of a base such as triethylamine, caesium carbonate potassium carbonate, diisopropylethylamine, pyridine and the like or a mixture thereof and preferable by using diisopropylethylamine. The reaction is carried out at room temperature. The duration of the reaction may range from 3 hours to 18 hours, preferably for the period of 10 hours to 16 hours.

The compounds of formula (1) may be prepared by using similar experimental procedure as mentioned in preparations 1 to 2 or can be prepared by conventional methods or may be commercially available. The compounds of formula (2) may be prepared by using similar experimental procedures as mentioned in preparations 3, 5, 6, 11 and 12 or can be prepared by conventional methods or may be commercially available Scheme II:

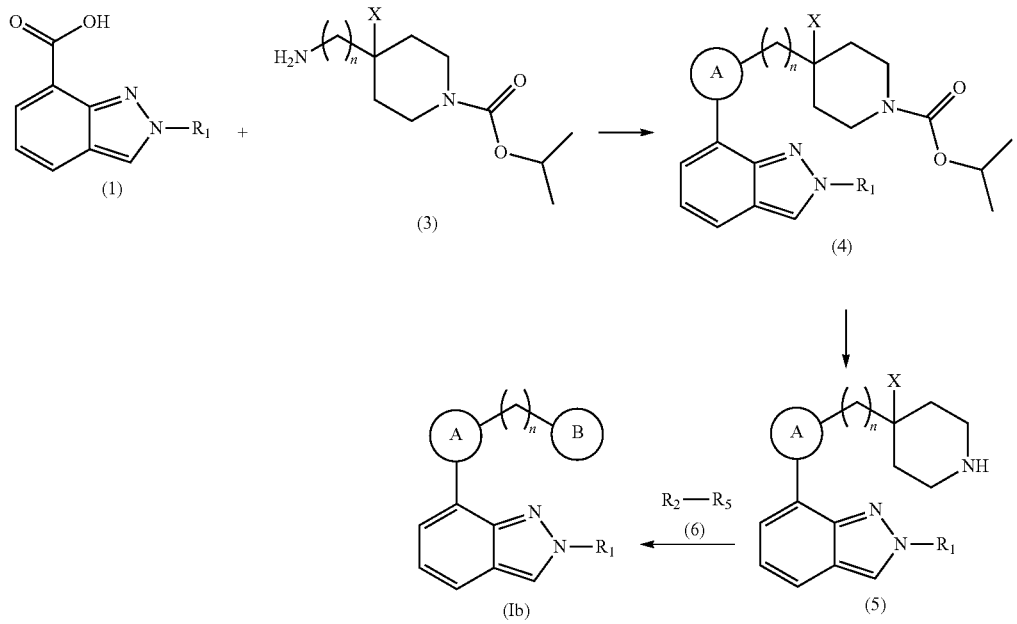

In Scheme II, all symbols are as defined above except $R_5$. The compounds of formula (Ib) are prepared according to Scheme II. $R_5$ represents a leaving group such as alkylsulfonate or halogen The compound of formula (1) is coupled with compound of formula (3) by using coupling reagent to form compound of formula (4). The reaction is carried out by using coupling agent such as O-(Benzotriazol-1-yl)-N,N,N',N'-tetramethyluronium tetrafluoroborate, carbonyldiimidazole, O-(Benzotriazol-1-yl)-N,N,N',N'-tetramethyluronium hexafluorophosphate, O-(7-Azabenzotriazol-1-yl)-N,N,N',N'-tetramethyluronium hexafluorophosphate, O-(6-Chlorobenzotriazol-1-yl)-N,N,N',N'-8 tetramethyluronium hexafluorophosphate, oxalyl chloride or thionyl chloride and preferably by using O-(Benzotriazol-1-yl)-N,N,N',N'-tetramethyluronium tetrafluoroborate. This reaction is carried out in a solvent such as dichloromethane, methanol, tetrahydrofuran, toluene, dimethylformamide, dimethyl sulfoxide, diethyl ether and the like or a mixture thereof and preferably by using dichloromethane. The reaction may be affected in the presence of a base such as triethylamine, caesium carbonate potassium carbonate, diisopropylethylamine, pyridine and the like or a mixture thereof and preferably by using diisopropylethylamine. The reaction is carried out at room temperature. The duration of the reaction may range from 12 hours to 18 hours, preferably for the period of 15 hours to 17 hours The compound of formula (4) is converted to the compound of formula (5) in presence of trifluoroacetic acid or dry hydrochloric acid followed by basification with inorganic bases such as sodiumbicarbonate. This reaction is carried out in a solvent such as isopropanol, dichloromethane, methanol, tetrahydrofuran, toluene, dimethylformamide, dimethyl sulfoxide, diethyl ether and the like or a mixture thereof and preferably by using isopropanol. The reaction is carried out at room temperature. The duration of the reaction may range from 1 hour to 14 hours, preferably for the period of 1 hour to 3 hours.

The compound of formula (5) is reacted with compound of formula (6) to form the compound of formula (Ib). This reaction is carried out in a solvent such as isopropanol, acetonitrile, dichloromethane, methanol, tetrahydrofuran, toluene, dimethylformamide, dimethyl sulfoxide, diethyl ether and the like or a mixture thereof and preferably by using methanol. The reaction may be affected in the presence of a base such as triethylamine, cesium carbonate, potassium carbonate, diisopropylethamine, pyridine and the like or a mixture thereof and preferably by using potassium carbonate. The reaction is carried out at room temperature. The duration of the reaction may range from 14 hours to 18 hours, preferably for the period of 15 hours to 17 hours.

The compounds of formula (1) may be prepared by using similar experimental procedure as mentioned in preparation 1 or can be prepared by conventional methods or may be commercially available.

The compounds of formula (3) may be prepared by using similar experimental procedure as mentioned in preparation 4 or can be prepared by conventional methods or may be commercially available.

The compounds of formula (6) can be prepared by conventional methods or may be commercially available.

Scheme III:

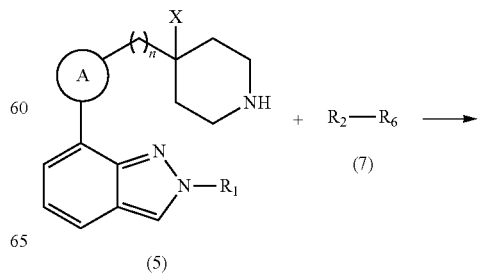

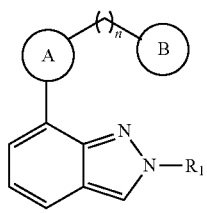

(Ic)

In Scheme III, all symbols are as defined above except $R_6$. The compounds of formula (Ic) are prepared according to Scheme III. $R_6$ represents a leaving group such as alkylsulfonate and halide or a formyl group. The compound of formula (5) is reacted with compound of formula (7) to form the compound of formula (Ic). This reaction is carried out in a solvent such as isopropanol, acetonitrile, dichloromethane, methanol, tetrahydrofuran, toluene, dimethylformamide, dimethyl sulfoxide, diethyl ether and the like or a mixture thereof and preferably by using dimethylformamide and acetonitrile. The displacement of the leaving group may be affected in the presence of bases such as cesium carbonate, triethylamine, potassium carbonate, diisopropylethylamine, pyridine and the like or a mixture thereof and preferably by using cesium carbonate or potassium carbonate. For reductive amination of carbonyl compounds, borane reagents such as sodium borohydride, sodium triacetoxyborohydride or sodium cyanoborohydride preferably sodium triacetoxyborohydride was used.

The compounds of formula (5) may be prepared by using similar experimental procedure as mentioned in step (ii) of example 26 and preparation 8 or can be prepared by conventional methods or may be commercially available.

The compounds of formula (7) can be prepared by conventional methods or may be commercially available.

Scheme IV:

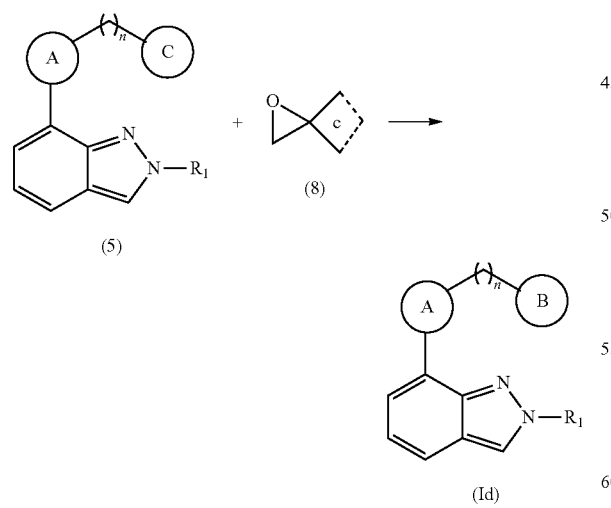

In Scheme IV, all symbols are as defined above. The compounds of formula (Id) are prepared according to Scheme IV. The compounds of formula (8) represents 2,2-dimethyloxirane, 1,6-dioxaspiro[2.5]octane and isobutylene oxide

represents

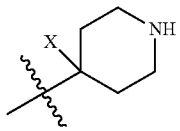 or 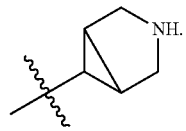

The compound of formula (5) is reacted with compound of formula (8) to form the compound of formula (Id). This reaction is carried out in a solvent such as isopropanol, acetonitrile, dichloromethane, methanol, tetrahydrofuran, toluene, dimethylformamide, dimethyl sulfoxide, diethyl ether and the like or a mixture thereof and preferably by using methanol, dimethylformamide and dichloromethane. The reaction may be affected in the presence of a base such as cesium carbonate, triethylamine, potassium carbonate, diisopropylethylamine, pyridine and the like or a mixture thereof and preferable by using triethylamine and cesium carbonate. The duration of the reaction may range from 5 hours to 25 hours, preferably for the period of 6 hours to 24 hours.

The compounds of formula (5) may be prepared by using similar experimental procedure as mentioned in step (ii) of example 26, step (i) of example 32, preparations 7 to 9 can be prepared by conventional methods or may be commercially available.

The compounds of formula (8) can be prepared by conventional methods or may be commercially available.

Scheme V:

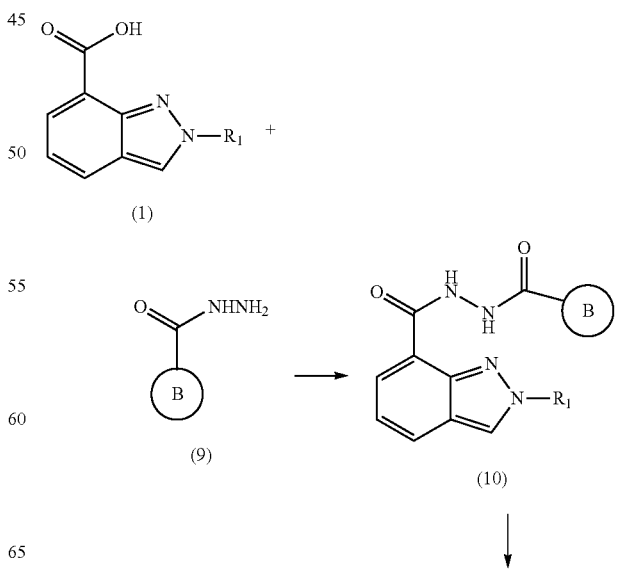

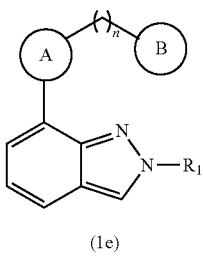

(Ie)

The compound of formula (1) is coupled with compound of formula (9) by using coupling reagent to form compound of formula (10). The reaction is carried out by using coupling agent such as O-(Benzotriazol-1-yl)-N,N,N',N'-tetramethyluronium tetrafluoroborate, carbonyldiimidazole, O-(Benzotriazol-1-yl)-N,N,N',N'-tetramethyluronium hexafluorophosphate, O-(7-Azabenzotriazol-1-yl)-N,N,N',N'-tetramethyluronium hexafluorophosphate, O-(6-Chlorobenzotriazol-1-yl)-N,N,N',N'-8 tetramethyluronium hexafluorophosphate oxalyl chloride or thionyl chloride and preferably by using thionyl chloride. This reaction is carried out in a solvent such as dichloromethane, dichloroethane, methanol, tetrahydrofuran, toluene, dimethylformamide, dimethyl sulfoxide, diethyl ether and the like or a mixture thereof and preferably by using dichloroethane. The duration of the reaction may range from 30 minutes to 2 hours, preferably for the period of 45 minutes to 1.5 hours.

The compound of formula (10) is cyclized to form compound of formula (Ie) by using dehydration agent. The reaction is carried out by using dehydration agent such as phosphorousoxychloride, polyphosphoric acid, phosphorus pentoxide or thionyl chloride, preferably by using phosphorousoxychloride. This reaction is carried out in a solvent such as dichloromethane, dichloroethane tetrahydrofuran, toluene, diethyl ether and the like or a mixture thereof, preferably by using dichloroethane. The duration of the reaction may range from 4 hours to 8 hours, preferably for the period of 5 hours to 7 hours.

The compounds of formula (9) may be prepared by using similar experimental procedure as mentioned in preparation 1 or can be prepared by conventional methods or may be commercially available.

The compounds of formula (10) may be prepared by using similar experimental procedures as mentioned in preparation 10 or can be prepared by conventional methods or may be commercially available.

If necessary, pharmaceutically acceptable salts for compounds of formula (I) may be prepared conventionally by reaction with the appropriate acid or acid derivative.

Suitable pharmaceutically acceptable salts will be apparent to those skilled in the art and include those described in Journal of Pharmaceutical Science, 1977, 66, 1-19. The salts are formed with inorganic acids e. g. hydrochloric, hydrobromic, sulfuric, nitric & phosphoric acid or organic acids e.g., succinic, maleic, acetic, fumaric, citric, malic, tartaric, benzoic, p-toluic, p-toluenesulfonic, benzenesulfonic acid, methanesulfonic or naphthalenesulfonic acid. The most preferred salts of compounds of formula (I) are tartarates, fumarates, oxalates and hydrochlorides.

Certain compounds of formula (I) are capable of existing in stereoisomeric forms (e. g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of compound of general formula (I) containing a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:

i) One or more of the reagents may be used in their optically active form.

ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

EXAMPLES

The novel compounds of the present invention were prepared according to the following experimental procedures, using appropriate raw materials and reaction conditions.

Preparation 1: Preparation of 2-isopropyl-2H-indazole-7-carboxylic acid

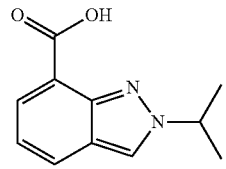

Step (i): Preparation of Isopropyl 2-isopropyl-2H-indazole-7-carboxylate

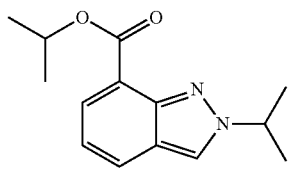 [SMILES: CC(C)OC(=O)c1cccc2cn(C(C)C)nc12]

To a stirred suspension of sodium hydride (NaH) (60% in nujol, 6.18 grams, 154.6 mmol) in dry dimethylformamide (DMF) (61 mL) cooled at 0° C. was added a solution of indazole-7-carboxylic acid (10.03 grams, 61.9 mmol) in DMF (61 mL). The reaction mixture was gradually warmed to room temperature and stirred for 2.5 hours. The reaction mixture was cooled again to 0° C. and neat 2-iodopropane (14.8 mL, 148 mmol) was added over a period of 15 minutes. The reaction mixture was gradually warmed to room temperature and stirred for 32 hours before being cooled to 0° C. and quenched by adding crushed ice. The mixture was extracted with dichloromethane (DCM). The combined organic layer was washed with brine and the solvent was removed under reduced pressure to obtain above ester (20.5 grams) which was taken up for the next reaction without further purification.

$^1$H-NMR CDCl$_3$ (δ ppm): 1.43 (6H, d, J=6.1 Hz), 1.68 (6H, bs), 4.93-5.05 (1H, m), 5.32-5.42 (1H, m), 7.11 (1H, t, J=7.6 Hz), 7.87 (1H, d, J=8.2 Hz), 8.0 (1H, d, J=7.5 Hz), 8.06 (1H, s).

Mass (m/z): 247.3 (M+H)$^+$.

Step (ii): Preparation of 2-isopropyl-2H-indazole-7-carboxylic acid

To a stirred solution of isopropyl 2-isopropyl-2H-indazole-7-carboxylate (20.49 grams, obtained in the above step) in a 1:1 mixture of tetrahydrofuran (THF) and water (122 mL) at 0° C. was added sodium hydroxide (NaOH) (8.36 grams, 208.0 mmol). The reaction mixture was gradually warmed to room temperature, heated to reflux and then refluxed for 16 hours. The reaction mixture was cooled to room temperature, the volatiles were removed under reduced pressure to obtain a crude mass which was diluted with water, extracted with ether, acidified to pH 5-6 and was extracted with DCM. The combined organic layer was washed with brine and the solvent was removed under reduced pressure to obtain the above title compound (11.1 grams). Yield: 88%.

$^1$H-NMR CDCl$_3$ (δ ppm): 1.71 (6H, d, J=6.6 Hz), 4.82-4.92 (1H, m), 7.26 (1H, t, J=7.0 Hz), 7.92 (1H, d, J=8.3 Hz), 8.12 (1H, s), 8.23 (1H, d, J=7.0 Hz), 12.1 (1H, bs).

Mass (m/z): 205.1 (M+H)$^+$.

Preparation 2: Preparation of 2-ethyl-2H-indazole-7-carboxylic acid

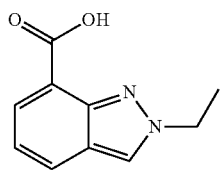

Step (i): Preparation of ethyl 2-ethyl-2H-indazole-7-carboxylate

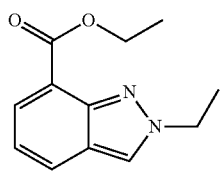 [SMILES: CCOC(=O)c1cccc2cn(CC)nc12]

To a stirred suspension of NaH (60% in nujol, 0.62 grams, 15.4 mmol) in dry DMF (8 mL) cooled at 0° C. was added a solution of indazole-7-carboxylic acid (1.0 gram, 6.1 mmol) in DMF (16 mL). The reaction mixture was gradually warmed to room temperature and stirred for 2.5 hours. The reaction mixture was cooled again to 0° C. and neat ethyl iodide (1.2 mL, 14.8 mmol) was added over a period of 15 minutes. The reaction mixture was gradually warmed to room temperature and stirred for 32 hours before being cooled to 0° C. and quenched by adding crushed ice. The mixture was extracted with DCM. The combined organic layer was washed with brine and the solvent was removed under reduced pressure to obtain the title compound (1.8 grams) which was taken up for the next reaction without further purification.

$^1$H-NMR (δ ppm, CDCl3): 1.44 (3H, t, J=7.0 Hz), 1.67 (3H, t, J=7.3 Hz), 4.76 (2H, q), 4.47 (2H, q), 7.13 (1H, t, J=7.6 Hz), 7.89 (1H, d, J=8.2 Hz), 8.05 (1H, s), 8.07 (1H, d, J=9.5 Hz).

Mass (m/z): 219.1 (M+H)$^+$.

Step (ii): Preparation of 2-ethyl-2H-indazole-7-carboxylic acid

To a stirred solution of ethyl 2-ethyl-2H-indazole-7-carboxylate (1.8 grams, obtained in the above step) in a 1:1 mixture of THF and water (32 mL) at 0° C. was added NaOH (0.83 grams, 20.7 mmol). The reaction mixture was gradually warmed to room temperature then refluxed for 16 hours. The reaction mixture was cooled to room temperature, the volatiles were removed under reduced pressure to obtain a crude mass which was diluted with water, extracted with ether, acidified to pH 5-6 and was extracted with DCM. The combined organic layer was washed with brine and the solvent was removed under reduced pressure to obtain the above titled compound (1.02 grams). Yield: 87% for above two steps.

¹H-NMR (δ ppm, CDCl3): 1.69 (3H, t, J=7.3 Hz), 4.55 (2H, q), 7.26 (1H, t, J=7.1 Hz), 7.92 (1H, d, J=8.23 Hz), 8.10 (1H, s), 8.23 (1H, d, J=7.0 Hz), 12.0 (1H, bs).

Mass (m/z): 191.2 (M+H)⁺.

Preparation 3:
4-Aminomethyl-1-(tetrahydropyran-4-yl methyl) piperidine

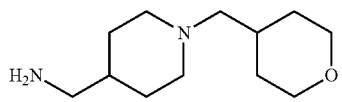

Step (i): Preparation of 1-(Tetrahydropyran-4-carbonyl) piperidine-4-carboxamide

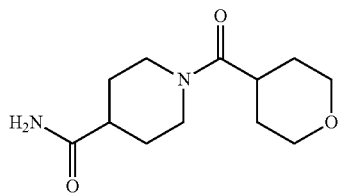

To a stirred solution of tetrahydropyran-4-carboxylic acid (10.0 grams, 76.9 mmols) in DCM (308 mL) cooled at 0° C., CDI (15.0 grams, 92.3 mmols) was added. The reaction mass was gradually warmed to room temperature and stirred for 30 minutes. The volatiles were removed under reduced pressure and the crude mass, thus obtained, was dissolved in DMF (154 mL). The solution of piperidine-4-carboxamide (11.8 grams, 92.3 mmols) in DMF (154 mL) was added over a period of 30 minutes. After stirring for 16 hours, the volatiles were removed under reduced pressure and the crude product was triturated with ethylacetate (EtOAc) to obtain the title compound as a white solid (15.1 grams). Yield: 82%.

¹H-NMR DMSO-d6 (δ ppm): 1.20-1.35 (1H, m), 1.35-1.65 (5H, m), 1.65-1.80 (2H, m), 2.25-2.35 (11, m), 2.50-2.60 (1H, m), 3.80-3.90 (1H, m), 2.95-3.08 (1H, m), 3.35-3.45 (2H, m), 3.80-3.88 (2H, m), 3.90-4.00 (1H, m), 4.30-4.40 (1H, m), 6.79 (1H, bs), 7.28 (1H, bs).

Mass (m/z): 241.4 (M+H)⁺.

Step (ii): Preparation of 4-Aminomethyl-1-(tetrahydropyran-4-yl methyl) piperidine

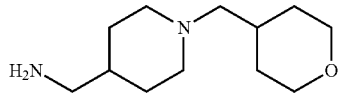

To the stirred solution of 1-(tetrahydropyran-4-carbonyl) piperidine-4-carboxamide (8.2 grams, 34.1 mmols, obtained in the above step) in THF (136 mL) cooled at 0° C., a solution of lithium aluminum hydride (LiAlH₄) (1M, 136.4 mL) in THF was added over a period of 30 minutes. The reaction mixture was gradually warmed to room temperature and then refluxed for 5 hours. The reaction mass was cooled to 0° C. and aqueous solution of sodium hydroxide (NaOH) (2.5 N, 34 mL) was added. After stirring for 15 minutes, the crude mass was filtered through a pad of celite. The celite pad was washed with 1:9 mixtures of methanol and DCM. The filtrate was dried over anhydrous sodium sulphate (Na₂SO₄) and the volatiles were removed under reduced pressure to obtain the above titled compound (8.3 grams). Yield: Quantitative.

¹H-NMR CDCl₃ (δ ppm): 1.12-1.32 (5H, m), 1.62-1.80 (5H, m), 1.80-1.90 (2H, m), 2.14 (2H, d, J=7.0 Hz), 2.83-2.90 (2H, m), 3.32-3.42 (2H, m), 3.92-4.40 (m, 2H).

Mass (m/z): 213.3 (M+H)⁺.

Preparation 4: Preparation of tert-butyl 4-aminomethyl-4-hydroxy piperidine-1-carboxylate

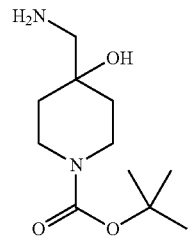 [SMILES: CC(C)(C)OC(=O)N1CCC(O)(CN)CC1]

Step (i): Preparation of tert-butyl 1-oxa-6-aza-spiro [2.5]octane-6-carboxylate

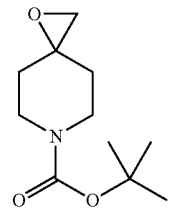

To a stirred suspension of NaH (60% in nujol, 0.24 grams, 6.03 mmol), washed with hexanes before use) in dimethyl sulfoxide (DMSO) (10.0 mL) at room temperature, trimethyloxosulfonium iodide (1.32 grams, 6.0 mmol) was added. After stirring for 15 minutes, N-boc piperidin-4-one (1.0 gram, 5.0 mmols) was added. The reaction mixture was stirred for 4 hours at room temperature before being quenched by the addition of ice water. The reaction mass was then extracted with ethyl acetate (EtOAc) and the combined organic layer was washed with brine solution, dried over anhydrous Na₂SO₄. The volatiles were removed under reduced pressure to obtain the above titled compound (0.65 gram). Yield: 60%.

¹H-NMR (δ ppm): 1.47 (9H, s), 1.59-1.62 (2H, m), 1.76-1.83 (2H, m), 2.69 (2H, s), 3.39-3.45 (2H, m), 3.70-3.73 (1H, m).

Mass (m/z): 158 (M−56)⁺.

Step (ii): Preparation of tert-butyl 4-aminomethyl-4-hydroxypiperidine-1-carboxylate To a stirred solution of tert-butyl 1-oxa-6-aza-spiro[2.5]octane-6-carboxylate (0.64 grams, 3.0 mmol, obtained in the above step) in methanol (4 mL) at room temperature, a solution of ammonia ($NH_3$) in methanol (7M, 8 mL) was added and the reaction was stirred for 12 hours. The volatiles were removed under reduced pressure to obtain the crude mass which was triturated with hexanes and ether which yielded the above titled compound (0.6 gram).

Yield: 86%.

$^1$H-NMR $CDCl_3$ (δ ppm): 1.45 (9H, s), 1.35-1.60 (4H, m), 2.63 (2H, s), 3.10-3.25 (2H, m), 3.80-3.95 (2H, m).

Mass (m/z): 231.5 (M+H)$^+$.

Preparation 5: 6-Aminomethyl-3-(3-methoxypropyl)-3-azabicyclo[3.1.0]hexane

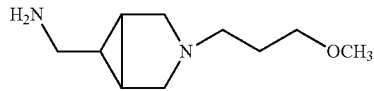 [SMILES: COCCCN1CC2C(CN)C2C1]

Step (i): Preparation of (3-Aza bicyclo[3.1.0]hex-6-yl) methanol

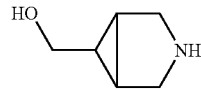

Hydrogen gas was passed into a stirred solution of (3-benzyl-3-azabicyclo[3.1.0]hex-6-yl)methanol (SYNLETT, 1996, 1097; 15.50 grams, 0.076 mole) and palladium hydroxide (7.75 grams, 50% w/w) in methanol (150 mL) over a period of 6 hours, while monitoring the progress of the reaction by thin layer chromatography (TLC). After completion of the reaction (TLC), the reaction mass was filtered through celite bed and the filtrate was concentrated under vacuum to afford the title compound (8.20 grams). Yield: 69%.

$^1$H-NMR (δ ppm): 0.89-0.96 (1H, m), 1.35-1.42 (2H, m), 2.05-2.07 (2H, m), 2.85-2.88 (2H, m), 2.98-3.01 (2H, m), 3.50-3.52 (1H, m), 3.94-3.96 (1H, m).

Mass (m/z): 114.3 (M+H)$^+$.

Step (ii): Preparation of tert-butyl 6-hydroxymethyl-3-azabicyclo[3.1.0]hexane-3-carboxylate

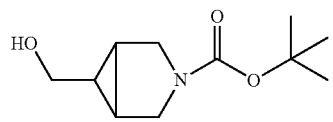

Di-tert-butyl dicarbonate (16.96 grams, 0.077 mole) was added to a solution of (3-aza bicyclo[3.1.0]hex-6-yl) methanol (8.00 grams, 0.070 mole, obtained in the above step) and TEA (11.40 grams, 0.112 mole) in DCM (150 mL) at 10° C. The reaction mass was stirred for 2 hours at 10° C., while monitoring the progress of the reaction by TLC. After completion of the reaction (TLC), the reaction mass was washed with chilled water (50 mL), brine solution (50 mL) and dried over sodium sulphate. The organic phase was concentrated under vacuum to obtain a crude residue, which was further purified by flash chromatography using ethyl acetate:n-hexane (50:50) to afford the above title compound (7.84 grams). Yield: 52%.

$^1$H-NMR (δ ppm): 0.92-0.97 (1H, m), 1.33-1.36 (1H, m), 1.43 (9H, s), 1.55-1.60 (2H, m), 3.32-3.37 (2H, m), 3.43-3.48 (1H, m), 3.53-3.58 (2H, m), 3.61-3.64 (1H, m).

Mass (m/z): 158.1 (M+H)$^+$.

Step (iii): Preparation of tert-butyl 6-methanesulfonyloxymethyl-3-aza bicyclo[3.1.0]hexane-3-carboxylate

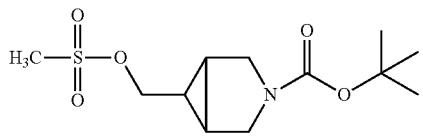 [SMILES: CC(C)(C)OC(=O)N1CC2C(COS(C)(=O)=O)C2C1]

A solution of methanesulfonylchloride (4.42 grams, 0.038 mole) in DCM (25 mL) was added to a solution of tert-butyl 6-hydroxymethyl-3-azabicyclo[3.1.0]hexane-3-carboxylate (7.80 grams, 0.036 mole, obtained in the above step) and TEA (5.58 grams, 0.055 mole) in DCM (100 mL) at 0° C. The reaction mass was stirred over night at room temperature, while monitoring the progress of the reaction by TLC. After completion of the reaction (TLC), the reaction mass was washed with chilled water (50 mL), brine solution (50 mL) and dried over sodium sulphate. The organic phase was concentrated under vacuum to afford the title compound (9.30 grams). Yield: 87%.

$^1$H-NMR (δ ppm): 1.11-1.15 (1H, m), 1.40-1.42 (1H, m), 1.45 (9H, s), 3.05 (3H, s), 3.17-3.19 (1H, m), 3.37-3.41 (2H, m), 3.58-3.68 (2H, m), 4.09-4.18 (2H, m).

Mass (m/z): 236.2 (M−56)$^+$.

Step (iv): Preparation of tert-butyl 6-Azidomethyl-3-azabicyclo[3.1.0]hexane-3-carboxylate

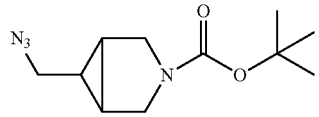

Sodium azide (7.30 grams, 0.112 mole) was added to a solution of tert-butyl 6-methanesulfonyloxymethyl-3-azabicyclo[3.1.0]hexane-3-carboxylate (9.30 grams, 0.039 mole, obtained in the above step) and $K_2CO_3$ (11.00 grams, 0.079 mole) in DMF (100 mL) at 10° C. Then the reaction mass was stirred over night at room temperature, while monitoring the progress of the reaction by TLC. After completion of the reaction (TLC), the reaction mass was poured onto chilled water (200 mL). The product was extracted with EtoAc (3×150 mL) and the combined organic phase was washed with chilled water (150 mL), brine solution (150 mL) and dried over sodium sulphate. The organic phase was concentrated under vacuum to afford the title compound (7.0 grams). Yield: 90%.

$^1$H-NMR (δ ppm): 0.97-1.00 (1H, m), 1.45 (9H, s), 1.50-1.53 (2H, m), 3.10-3.15 (1H, m), 3.22-3.27 (1H, m), 3.35-3.39 (2H, m), 3.57-3.67 (2H, m).

Mass (m/z): 183.3 (M−56)$^+$.

Step (v): Preparation of tert-butyl 6-aminomethyl-3-azabicyclo[3.1.0]hexane-3-carboxylate

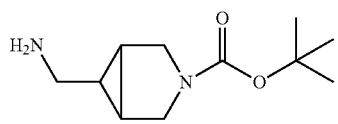

A solution of tert-butyl 6-azidomethyl-3-azabicyclo[3.1.0]hexane-3-carboxylate (1.50 grams, 0.006 mole, obtained in the above step) in THF (30 mL) and water (3 mL) mixture was treated with triphenylphosphine (2.1 grams, 0.008 mole). The reaction mass was stirred for 36 hours at room temperature, while monitoring the progress of the reaction by TLC. After completion of the reaction (TLC), the reaction mass was concentrated under vacuum to obtain a crude residue, which was further purified by flash chromatography using triethylamine (TEA): methanol:DCM (2:8:90) to afford the title compound (1.2 grams). Yield: 90%.

$^1$H-NMR (δ ppm): 0.66-0.70 (1H, m), 0.95-0.99 (1H, t), 1.17-1.19 (1H, m), 1.33 (9H, s), 1.53-1.55 (2H, m), 2.67-2.69 (2H, m), 3.36-3.41 (2H, m), 7.73 (2H, bs).

Mass (m/z): 213.3 (M+H)$^+$.

Step (vi): Preparation of 6-Azidomethyl-3-aza bicyclo[3.1.0]hexane hydrochloride

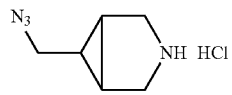

To a stirred solution of tert-butyl 6-Azidomethyl-3-azabicyclo[3.1.0]hexane-3-carboxylate (19.95 grams, 83.84 mmol, obtained in the above step) in isopropanol (42 mL) cooled at 0° C., a solution of dry hydrochloride (HCl) in isopropanol (3 M, 335 mL) was added over a period of 30 minutes. The reaction mixture was gradually warmed to room temperature and stirred for 12 hours. The volatiles were removed under reduced pressure and the crude mass was triturated with diethylether to obtain above titled compound (14.39 grams). Yield: 98%.

$^1$H-NMR CDCl$_3$ (δ ppm): 1.55-1.65 (1H, m), 1.65-1.80 (2H, m), 3.25 (2H, d, J=6.3 Hz), 3.40-3.50 (2H, m), 3.50-3.60 (2H, m), 9.28 (1H, bs), 9.96 (1H, bs).

Mass (m/z): 139.1 (M+H)$^+$.

Step (vii): Preparation of 6-Azidomethyl-3-(3-methoxy propyl)-3-aza bicyclo[3.1.0]hexane

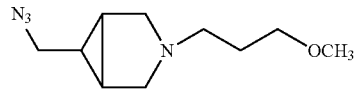 [SMILES: COCCCN1CC2C(CN=[N+]=[N-])C2C1]

To a stirred suspension of 6-Azidomethyl-3-azabicyclo[3.1.0]hexane hydrochloride (3.06 grams, 17.53 mmol, obtained in the above step) in acetonitrile (90 mL) at room temperature, added solid cesium carbonate (Cs$_2$CO$_3$) (17.1 grams, 52.6 mmol) followed by neat 1-bromo-3-methoxypropane (2.6 mL, 22.8 mmol). The reaction mixture was then gradually heated to reflux and refluxed for 8 hours. The insolubles were filtered after cooling the reaction mass to room temperature and the filtrate was evaporated. The crude product was diluted with water and extracted with EtOAc. The combined organic layer was dried over anhydrous Na$_2$SO$_4$ and the solvent was removed under reduced pressure to obtain the above titled compound (3.3 grams). Yield: 89%.

$^1$H-NMR CDCl$_3$ (δ ppm): 1.43-1.55 (1H, m), 1.62-1.72 (2H, m), 2.29 (2H, d, J=8.2 Hz), 2.46 (2H, t, J=7.2 Hz), 3.04 (2H, d, J=8.4 Hz), 3.08 (2H, t, J=6.9 Hz), 3.31 (3H, s), 3.38 (2H, t, J=6.4 Hz).

Mass (m/z): 211.0 (M+H)$^+$.

Step (viii): Preparation of 6-aminomethyl-3-(3-methoxypropyl)-3-azabicyclo[3.1.0]hexane To a stirred solution of 6-azidomethyl-3-(3-methoxy propyl)-3-aza bicyclo[3.1.0]hexane (3.3 grams, 15.7 mmol, obtained in the above step) in THF (75 mL) cooled at 0° C., triphenylphosphine (4.5 grams, 17.26 mmol) followed by water (1.0 mL, 55.0 mmols) was added. The reaction mixture was gradually warmed to room temperature and stirred for 12 hours. The volatiles were removed under reduced pressure and the crude mass was diluted with HCl (2N, 33 mL) and extracted with ether. The aqueous layer was cooled to 0° C. and basified with aqueous sodium bicarbonate (NaHCO$_3$) solution to pH 8-9 and extracted with DCM. The combined organic layer was dried over anhydrous Na$_2$SO$_4$ and the solvent was removed under reduced pressure to obtain the above titled compound (2.15 grams). Yield: 74%.

$^1$H-NMR CDCl$_3$ (δ ppm): 1.18-1.22 (2H, m), 1.22-1.30 (1H, m), 1.63-1.74 (2H, m), 2.25-2.31 (2H, m), 2.45 (2H, t, J=7.2 Hz), 2.50 (2H, d, J=7.0 Hz), 2.98-3.05 (2H, m), 3.30 (3H, s), 3.34-3.42 (2H, m).

Mass (m/z): 185.2 (M+H)$^+$.

Preparation 6: Preparation of 3-(4-Aminomethyl piperidin-1-yl)-2,2-dimethyl propan-1-ol

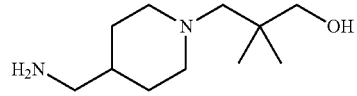

Step (i): Preparation of methyl 3-{4-[(N,N-dibenzy-lamino) methyl]piperidin-1-yl}-2,2-dimethyl propionate

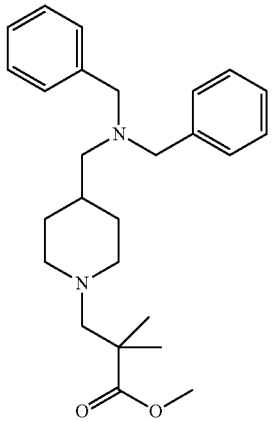 [SMILES: COC(=O)C(C)(C)CN1CCC(CN(Cc2ccccc2)Cc2ccccc2)CC1]

A solution of 4-(N,N-dibenzylamino methyl) piperidine (1 gram, 3.40 mmol) and methyl 2,2-dimethyl-3-oxo propionate (1.3 grams, 10 mmol) in dichloroethane (DCE) (25 mL) was cooled to 10° C. and treated with sodium triacetoxyborohydride (1.58 grams, 7.45 mmol). The reaction mass was stirred overnight at room temperature, while monitoring the progress of the reaction by TLC. As TLC showed complete conversion of the starting material into product, the reaction mass was concentrated and the obtained slurry was diluted with water (30 mL). The pH of the mass was adjusted to ~9.5 using aqueous $NH_3$ and the compound was extracted with DCM (3×10 mL). The combined organic phase was washed with water (15 mL), brine solution (15 mL) and dried over $Na_2SO_4$. The organic phase was concentrated on rotavacuum to obtain the crude residue, which was further purified by flash chromatography using ethyl acetate:n-hexane (5:95) to afford the title compound (0.78 gram). Yield: 56.53%.
$^1$H-NMR (δ ppm): 0.86-0.91 (2H, m), 1.01-1.25 (9H, m), 2.04-2.13 (1H, m), 2.19-2.29 (4H, m), 2.42 (1H, m), 2.68-2.71 (1H, m), 3.49-3.56 (4H, m), 3.63-3.71 (4H, m), 7.20-7.35 (10H, m).
Mass (m/z): 409.2 (M+H)$^+$.

Step (ii): Preparation of 3-{4-[(N,N-dibenzylamino) methyl]piperidin-1-yl}-2,2-dimethyl propanol

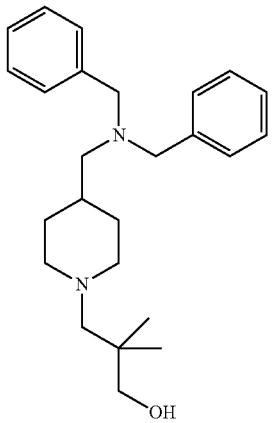 [SMILES: CC(C)(CO)CN1CCC(CN(Cc2ccccc2)Cc2ccccc2)CC1]

1M solution of $LiAlH_4$ (5.73 mL) was added to a stirred solution of methyl 3-{4-[(N,N-dibenzylamino) methyl]piperidin-1-yl}-2,2-dimethyl propionate (0.78 gram, 1.91 mmole, obtained in the above step) in THF (25 mL) at 0° C. Then reaction mass temperature was slowly raised to room temperature and stirred for 4 hours at same temperature. The progress of the reaction was monitored by thin layer chromatography. After completion of the reaction (TLC), the mass was cooled to 0° C. and added water (1 mL), followed by EtOAc (25 mL). The resulting solution was filtered through celite pad and was washed with EtOAc (20 mL). The filtrate was dried over $Na_2SO_4$. The organic phase was filtered and concentrated under vacuum to afford the title compound (0.57 gram). Yield: 79.7%.
$^1$H-NMR (δ ppm): 0.89-0.92 (6H, m), 1.05-1.07 (2H, m), 1.19-1.26 (2H, m), 1.69-1.78 (2H, m), 2.05-2.13 (2H, m), 2.20-2.36 (6H, m), 2.89-2.92 (2H, m), 3.46-3.51 (4H, m), 7.20-7.35 (10H, m).
Mass (m/z): 381.4 (M+H)$^+$.

Step (iii): Preparation of 3-(4-aminomethyl piperidin-1-yl)-2,2-dimethyl propanol Hydrogen gas was passed into a stirred solution of 3-{4-[(N,N-dibenzylamino) methyl]piperidin-1-yl}-2,2-dimethyl propanol (0.55 gram, 1.44 mmol, obtained in the above step) and palladium hydroxide (0.275 grams, 50% w/w) in methanol (25 mL) over a period of 4 hours, while monitoring the progress of the reaction by TLC. After completion of the reaction (TLC), the reaction mass was filtered through celite bed and the filtrate was concentrated under vacuum to afford the title compound (0.24 gram). Yield: 82.75%.
$^1$H-NMR (δ ppm): 0.74 (6H, S), 1.00-1.07 (2H, m), 1.20-1.25 (1H, m), 1.32-1.41 (1H, m), 1.53-1.58 (2H, m), 1.98-2.09 (3H, m), 2.34-2.36 (1H, m), 2.74-2.77 (2H, m), 3.13-3.15 (4H, m), 4.30-4.37 (1H, m), 4.59-4.63 (1H, m).
Mass (m/z): 201.4 (M+H)$^+$.

Preparation 7: Preparation of N-[(4-fluoro piperidin-4-yl)methyl]-2-isopropyl-2H-indazole-7-carboxamide

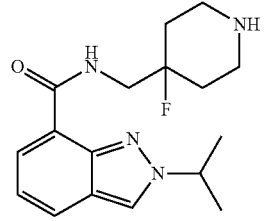 [SMILES: CC(C)n1cc2cccc(C(=O)NCC3(F)CCNCC3)c2n1]

Step (i): Preparation of tert-butyl 1-Oxa-6-aza spiro[2.5]octane-6-carboxylate

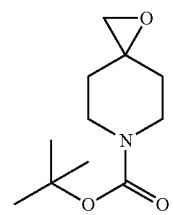

Trimethylsulfoxonium iodide (13.3 grams, 0.06 mole) was added to a stirred solution of NaH (60% dispersion in oil, 3.0 grams, 0.126 mole) in THF (150 mL) at 10° C. Reaction mass temperature was slowly raised to room temperature and stirred further for 2 hours at the same temperature. Reaction mass was then cooled to 10° C. and added N-boc-piperidin-4-one (10.0 grams, 0.05 mole) solution in THF (50 mL) at the same temperature. Then reaction mass temperature was slowly raised to room temperature and stirred for 3 hours at same temperature. The progress of the reaction was monitored by TLC. After completion of the reaction (TLC), the mass was quenched in chilled water (300 mL), the compound was extracted with DCM (3×150 mL). The combined organic phase was washed with water (100 mL), brine solution (100 mL) and dried over Na₂SO₄. The organic phase was concentrated on rotavacuum to obtain the crude residue, which was further purified by flash chromatography using ethyl acetate:n-hexane (15:85) to afford the title compound (7.1 grams). Yield: 66%.

¹H-NMR (δ ppm): 1.47 (9H, s), 1.59-1.62 (2H, m), 1.76-1.83 (2H, m), 2.69 (2H, s), 3.39-3.45 (2H, m), 3.70-3.73 (2H, m).

Mass (m/z): 158.2 (M−56)$^+$.

Step (ii): Preparation of tert-butyl 4-[(dibenzylamino) methyl]-4-hydroxy piperidine-1-carboxylate

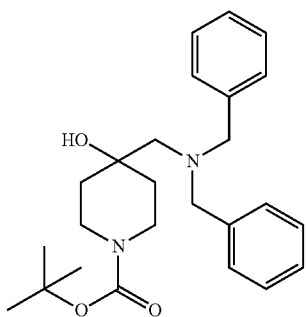 [SMILES: CC(C)(C)OC(=O)N1CCC(O)(CN(Cc2ccccc2)Cc2ccccc2)CC1]

Dibenzylamine (7.98 grams, 0.04 mole) was added to a stirred solution of tert-butyl 1-oxa-6-aza-spiro[2.5]octane-6-carboxylate (7.86 grams, 0.036 mole, obtained in the above step) and TEA (11.19 grams, 0.118 mole) in methanol (100 mL) at room temperature. Then reaction mass temperature was slowly raised to 75° C. and stirred for 38 hours at same temperature. The progress of the reaction was monitored by TLC. After completion of the reaction (TLC), the reaction mass was concentrated on rotavacuum to obtain the crude residue, which was further purified by flash chromatography using ethyl acetate:n-hexane (15:85) to afford the title compound (7.1 grams). Yield: 46%.

¹H-NMR (δ ppm): 1.43 (9H, s), 1.89-1.94 (2H, m), 2.14-2.19 (1H, m), 2.55-2.60 (2H, m), 2.92 (1H, s), 3.03-3.09 (2H, m), 3.43-3.45 (1H, m), 3.64 (4H, bs), 3.69-3.84 (2H, m), 7.16-7.35 (10H, m).

Mass (m/z): 411.3 (M+H)$^+$.

Step (iii): Preparation of tert-butyl 4-[(dibenzylamino) methyl]-4-fluoro piperidine-1-carboxylate

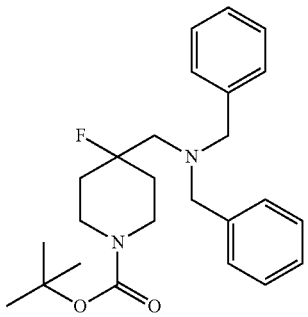 [SMILES: CC(C)(C)OC(=O)N1CCC(F)(CN(Cc2ccccc2)Cc2ccccc2)CC1]

Diethylaminosulfur trifluoride (DAST) (3.3 grams, 0.02 mole) was added to a stirred solution of tert-butyl 4-[(dibenzylamino) methyl]-4-hydroxy piperidine-1-carboxylate (7.0 grams, 0.017 mole, obtained in the above step) in DCM (70 mL) at −40° C. Then reaction mass temperature was slowly raised to room temperature and stirred over night at the same temperature. The progress of the reaction was monitored by TLC. After completion of the reaction (TLC), the mass was quenched in chilled water (100 mL). The pH of the mass was adjusted to ~9.5 using aqueous NH₃ and the compound was extracted with DCM (3×50 mL). The combined organic phase was washed with water (75 mL), brine solution (75 mL) and dried over sodium sulphate. The organic phase was concentrated on rotavacuum to obtain the crude residue, which was further purified by flash chromatography using ethyl acetate:n-hexane (5:95) to afford the title compound (4.35 grams). Yield: 61%.

¹H-NMR (δ ppm): 1.45 (9H, s), 1.89-1.94 (2H, m), 2.14-2.19 (1H, m), 2.55-2.60 (2H, m), 3.03-3.09 (2H, m), 3.43-3.45 (1H, m), 3.64 (4H, bs), 3.69-3.84 (2H, m), 7.16-7.35 (10H, m).

Mass (m/z): 413.3 (M+H)$^+$.

Step (iv): Preparation of tert-Butyl 4-aminomethyl-4-fluoro piperidine-1-carboxylate

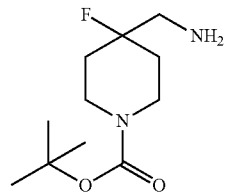 [SMILES: CC(C)(C)OC(=O)N1CCC(F)(CN)CC1]

Hydrogen gas was passed into a stirred solution of tert-Butyl 4-aminomethyl-4-fluoro piperidine-1-carboxylate (1.37 grams, 3.28 mmole, obtained in the above step) and palladium hydroxide (1.37 grams, 50% w/w) in methanol (30 mL) over a period of 8 hours. The progress of the reaction was monitored by TLC. After completion of the reaction (TLC), the reaction mass was filtered through celite bed and the filtrate was concentrated on rotavacuum to afford the title compound (0.66 gram). Yield: 85%.

¹H-NMR (δ ppm): 1.38 (9H, s), 1.44-1.71 (6H, m), 2.60-2.64 (2H, m), 2.95 (2H, bs), 3.73-3.76 (2H, m).

Mass (m/z): 233.2 (M+H)$^+$.

Step (v): Preparation of N-[(1-tert-butyloxy carbonyl-4-fluoro piperidin-4-yl)methyl]-2-isopropyl-2H-indazole-7-carboxamide

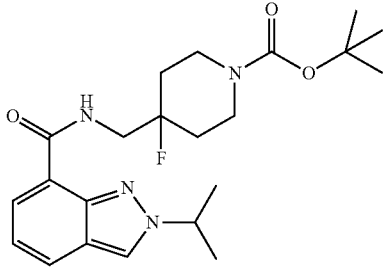 [SMILES: CC(C)n1cc2cccc(C(=O)NCC3(F)CCN(C(=O)OC(C)(C)C)CC3)c2n1]

A solution of 2-isopropyl-2H-indazole-7-carboxylic acid (0.21 gram, 1.02 mmol, obtained in the preparation 1) and CDI (0.25 gram, 1.54 mmole) in DCM (10 mL) was stirred for 3 hours at room temperature. Then added a solution of with 4-aminomethyl-4-fluoro piperidine-1-carboxylic acid tert-butyl ester (0.3 gram, 1.29 mmol, obtained in the above step) in DCM (5 mL). The reaction mass was stirred over night (12 hours) at room temperature under nitrogen atmosphere, while monitoring the progress of the reaction by TLC. After completion of the reaction (TLC), the reaction mass was washed with chilled water (5 mL), brine solution (5 mL) and dried over $Na_2SO_4$. The organic phase was concentrated on rotavacuum to obtain the crude residue, which was further purified by flash chromatography using ethyl acetate:n-hexane (50:50) to afford the title compound (0.38 gram). Yield: 88.37%.

$^1$H-NMR (δ ppm): 1.40 (9H, s), 1.57-1.59 (6H, d), 1.71-1.75 (2H, m), 1.83-1.86 (2H, m), 3.15-3.16 (2H, m), 3.68-3.79 (4H, m), 4.87-4.93 (1H, m), 7.17-7.21 (1H, m), 7.91-8.00 (2H, m), 8.65 (1H, s), 9.46 (1H, bs).

Mass (m/z): 419.3 $(M+H)^+$.

Step (vi): Preparation of N-[(4-fluoro piperidin-4-yl)methyl]-2-isopropyl-2H-indazole-7-carboxamide Ethanolic hydrogen chloride (23% w/w, 0.33 gram, 9.08 mmol) was added to a solution of N-[(1-tert-butyloxy carbonyl-4-fluoro piperidin-4-yl)methyl]-2-isopropyl-2H-indazole-7-carboxamide (0.38 gram, 0.9 mmole, obtained in the above step) in ethanol (10 mL) at 10° C. The reaction mass was stirred 5 hours at room temperature, while monitoring the progress of the reaction by TLC. As TLC reveals completion of the reaction, the reaction mass was concentrated and the slurry, thus obtained, was dissolved in cold water (15 mL). The pH was adjusted to ~9.5 using aqueous $NH_3$ solutions and the product was extracted with DCM (3×10 mL). The combined organic phase was washed with water (10 mL), brine solution (10 mL) and dried over sodium sulphate. The organic phase was concentrated under vacuum to afford the title compound (0.2 gram). Yield: 71.42%.

$^1$H-NMR (δ ppm): 1.66-1.68 (6H, d), 1.78-1.85 (2H, m), 1.90-1.96 (2H, m), 2.89-2.91 (5H, m), 3.74-3.80 (2H, m), 4.87-4.93 (1H, m), 7.19-7.22 (1H, m), 7.93-8.09 (2H, m), 8.43, (1H, s), 9.46 (1H, bs).

Mass (m/z): 319.4 $(M+H)^+$.

Preparation 8: Preparation of N-(piperidin-4-yl methyl)-2-isopropyl-2H-indazole-7-carboxamide

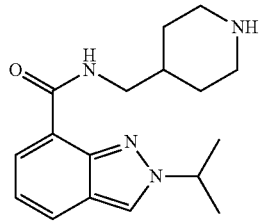 [SMILES: CC(C)n1cc2cccc(C(=O)NCC3CCNCC3)c2n1]

Step (i): Preparation of N-[(1-tert-butyloxy carbonyl piperidin-4-yl)methyl]-2-isopropyl-2H-indazole-7-carboxamide

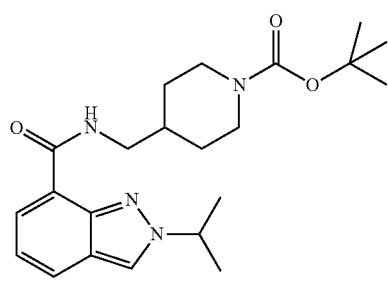 [SMILES: CC(C)n1cc2cccc(C(=O)NCC3CCN(C(=O)OC(C)(C)C)CC3)c2n1]

A solution of 2-isopropyl-2H-indazole-7-carboxylic acid (0.4 gram, 1.96 mmol, obtained in the preparation 1) and carbonyldiimidazole (0.41 gram, 2.53 mmole) in DCM (10 mL) was stirred for 3 hours at room temperature. Then added a solution of tert-butyl 4-(aminomethyl) piperidine-1-carboxylate (0.47 grams, 2.20 mmole) in DCM (5 ml). The reaction mass was stirred over night (12 hours) at room temperature under nitrogen atmosphere, while monitoring the progress of the reaction by TLC. After completion of the reaction (TLC), the reaction mass was transferred into a separating funnel, washed with cold water (5 mL), brine solution (5 mL) and dried over $Na_2SO_4$. The organic phase was concentrated on rotavacuum to obtain the crude residue, which was further purified by flash chromatography using ethyl acetate:n-hexane (50:50) to afford the title compound (0.59 gram). Yield: 75.64%.

$^1$H-NMR (δ ppm): 1.13-1.16 (1H, m), 1.41 (9H, s), 1.57-1.59 (6H, d), 1.71-1.75 (4H, m), 2.70-2.76 (2H, m), 3.32-3.36 (2H, m), 3.95-3.97 (2H, m), 4.87-4.94 (1H, m), 7.16-7.19 (1H, m), 7.91-7.97 (2H, m), 8.65 (1H, s), 9.25 (1H, bs).

Mass (m/z): 401.3 $(M+H)^+$.

Step (ii): Preparation of N-(piperidin-4-yl methyl)-2-isopropyl-2H-indazole-7-carboxamide Ethanolic hydrogen chloride (23% w/w, 0.33 gram, 9.08 mmole) was added to a solution of N-[(1-tert-butyloxy carbonyl piperidin-4-yl)methyl]-2-isopropyl-2H-indazole-7-carboxamide (0.58 gram, 1.45 mmol, obtained in the above step) in ethanol (20 mL) at 10° C. The reaction mass was stirred 5 hours at room temperature, while monitoring the progress of the reaction by TLC. After TLC reveals completion of the reaction, the reaction mass was concentrated and the slurry, thus obtained, was diluted with cold water (15 mL). The pH was adjusted to ~9.5 using aqueous NH₃ solution and the product was extracted with DCM (3×10 mL). The combined organic phase was washed with water (10 mL), brine solution (10 mL) and dried over Na₂SO₄. The organic phase was concentrated under vacuum to afford the title compound (0.34 gram). Yield: 79.06%.

¹H-NMR (δ ppm): 1.18-1.24 (4H, m), 1.57-1.59 (6H, d), 1.66-1.73 (4H, m), 2.49-2.55 (2H, m), 2.96-3.01 (2H, m), 4.87-4.94 (1H, m), 7.16-7.20 (1H, m), 7.91-7.97 (2H, m), 8.65 (1H, s), 9.26-9.28 (1H, t).

Mass (m/z): 301.3 (M+H)⁺.

Preparation 9: Preparation of N-[(3-aza bicyclo [3.1.0]hexane-6-yl)methyl]-2-Isopropyl-2H-indazole-7-carboxamide

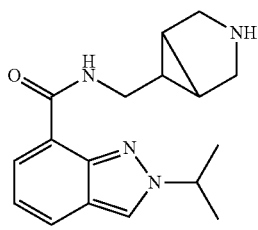 [SMILES: CC(C)n1cc2cccc(C(=O)NCC3C4CNCC43)c2n1]

Step (i): Preparation of (3-aza bicyclo[3.1.0]hexane-6-yl) methanol

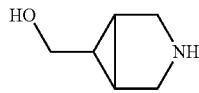

Hydrogen gas was passed into a stirred solution of (3-benzyl-3-aza bicyclo[3.1.0]hexane-6-yl) methanol (15.50 grams, 0.076 mole) and palladium hydroxide (7.75 grams, 50% w/w) in methanol (150 mL) over a period of 6 hours, while monitoring the progress of the reaction by TLC. After completion of the reaction (TLC), the reaction mass was filtered through celite bed and the filtrate was concentrated under vacuum to afford the title compound (8.2 grams). Yield: 69%.

¹H-NMR (δ ppm): 0.89-0.96 (1H, m), 1.35-1.42 (2H, m), 2.05-2.07 (2H, m), 2.85-2.88 (2H, m), 2.98-3.01 (2H, m), 3.50-3.52 (1H, m), 3.94-3.96 (1H, m).

Mass (m/z): 114.3 (M+H)⁺.

Step (ii): Preparation of tert-butyl 6-hydroxymethyl-3-aza bicyclo[3.1.0]hexane-3-carboxylate

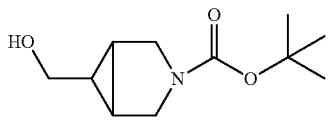

Di-tert-butyl dicarbonate (16.96 grams, 0.077 mole) was added to a solution of (3-aza bicyclo[3.1.0]hex-6-yl) methanol (8.0 grams, 0.070 mole, obtained in the above step) and TEA (11.40 grams, 0.112 mole) in DCM (150 mL) at 10° C. The reaction mass was stirred for 2 hours at 10° C., while monitoring the progress of the reaction by TLC. After completion of the reaction (TLC), the reaction mass was washed with chilled water (50 mL), brine solution (50 mL) and dried over Na₂SO₄. The organic phase was concentrated under vacuum to obtain a crude residue, which was further purified by flash chromatography using ethyl acetate:n-hexane (50:50) to afford the title compound (7.84 grams). Yield: 52%.

¹H-NMR (δ ppm): 0.92-0.97 (1H, m), 1.33-1.36 (1H, m), 1.43 (9H, s), 1.55-1.60 (2H, m), 3.32-3.37 (2H, m), 3.43-3.48 (1H, m), 3.53-3.58 (2H, m), 3.61-3.64 (1H, m).

Mass (m/z): 158.1 (M+H)⁺.

Step (iii): Preparation of tert-butyl 6-methanesulfonyloxymethyl-3-aza bicyclo[3.1.0]hexane-3-carboxylate

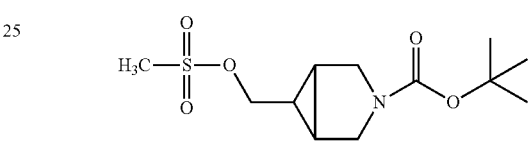

A solution of methanesulfonylchloride (4.42 grams, 0.038 mole) in DCM (25 mL) was added to a solution of tert-butyl 6-hydroxymethyl-3-azabicyclo[3.1.0]hexane-3-carboxylate (7.80 grams, 0.036 mole, obtained in the above step) and TEA (5.58 grams, 0.055 mole) in DCM (100 mL) at 0° C. The reaction mass was stirred over night at room temperature, while monitoring the progress of the reaction by TLC. After completion of the reaction (TLC), the reaction mass was washed with chilled water (50 mL), brine solution (50 mL) and dried over Na₂SO₄. The organic phase was concentrated under vacuum to afford the title compound (9.30 grams). Yield: 87%.

¹H-NMR (δ ppm): 1.11-1.15 (1H, m), 1.40-1.42 (1H, m), 1.45 (9H, s), 3.05 (3H, s), 3.17-3.19 (1H, m), 3.37-3.41 (2H, m), 3.58-3.68 (2H, m), 4.09-4.18 (2H, m).

Mass (m/z): 236.2 (M–56)⁺.

Step (iv): Preparation of tert-butyl 6-Azidomethyl-3-azabicyclo[3.1.0]hexane-3-carboxylate

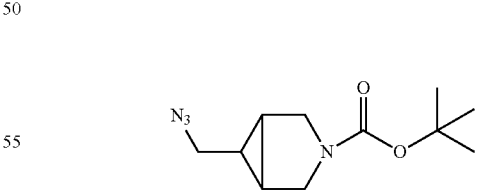

Sodium azide (7.30 grams, 0.112 mole) was added to a solution of tert-butyl 6-methanesulfonyloxymethyl-3-azabicyclo[3.1.0]hexane-3-carboxylate (9.30 grams, 0.039 mole, obtained in the above step) and K₂CO₃ (11.00 grams, 0.079 mole) in DMF (100 mL) at 10° C. Then the reaction mass was stirred over night at room temperature, while monitoring the progress of the reaction by TLC. After completion of the reaction (TLC), the reaction mass was poured onto chilled water (200 mL). The product was extracted with EtOAc (3×150 mL) and the combined organic phase was washed with chilled water (150 mL), brine solution (150 mL) and dried over Na₂SO₄. The organic layer was concentrated under vacuum to afford the title compound (7.0 grams). Yield: 90%.

¹H-NMR (δ ppm): 0.97-1.00 (1H, m), 1.45 (9H, s), 1.50-1.53 (2H, m), 3.10-3.15 (1H, m), 3.22-3.27 (1H, m), 3.35-3.39 (2H, m), 3.57-3.67 (2H, m).

Mass (m/z): 183.3 (M−56)⁺.

Step (v): Preparation of tert-butyl 6-aminomethyl-3-azabicyclo[3.1.0]hexane-3-carboxylate

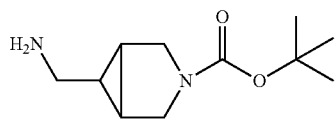

A solution of tert-butyl 6-azidomethyl-3-azabicyclo[3.1.0]hexane-3-carboxylate (1.50 grams, 0.006 mole, obtained in the above step) in THF (30 mL) and water (3 mL) mixture was treated with triphenylphosphine (2.1 grams, 0.008 mole). The reaction mass was stirred for 36 hours at room temperature, while monitoring the progress of the reaction by TLC. After completion of the reaction (TLC), the reaction mass was concentrated under vacuum to obtain a crude residue, which was further purified by flash chromatography using triethylamine, methanol and dichloromethane in 2:8:90 ratio respectively to afford the title compound (1.2 grams). Yield: 90%.

¹H-NMR (δ ppm): 0.66-0.70 (1H, m), 0.95-0.99 (1H, t), 1.17-1.19 (1H, m), 1.33 (9H, s), 1.53-1.55 (2H, m), 2.67-2.69 (2H, m), 3.36-3.41 (2H, m), 7.73 (2H, bs).

Mass (m/z): 213.3 (M+H)⁺.

Step (vi): Preparation of N-[(3-tert-butyloxy carbonyl-3-aza bicyclo[3.1.0]hexane-6-yl)methyl]-2-isopropyl-2H-indazole-7-carboxamide

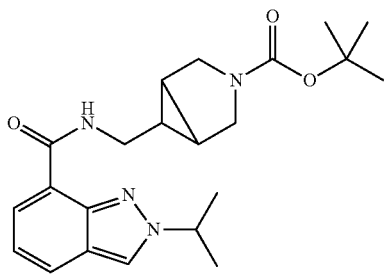 [SMILES: CC(C)n1cc2cccc(C(=O)NCC3C4CN(C(=O)OC(C)(C)C)CC34)c2n1]

A solution of 2-isopropyl-2H-indazole-7-carboxylic acid (0.25 grams, 1.21 mmol, obtained in the preparation 1) and CDI (0.294 gram, 1.81 mmole) in DCM (10 mL) was stirred for 3 hours at room temperature. Then added a solution of tert-butyl 6-aminomethyl-3-azabicyclo[3.1.0]hexane-3-carboxylate (0.364 gram, 1.71 mmole, obtained in the above step) in DCM (5 mL). The reaction mass was stirred over night (16 hours) at room temperature under nitrogen atmosphere, while monitoring the progress of the reaction by TLC. After completion of the reaction (TLC), the reaction mass was washed with chilled water (5 mL), brine solution (5 mL) and dried over Na₂SO₄. The organic phase was concentrated on rotavacuum to obtain the crude residue, which was further purified by flash chromatography using EtOAc:n-hexane (50:50) to afford the title compound (0.36 gram). Yield: 73.46%.

¹H-NMR (δ ppm): 0.81-0.85 (2H, m), 1.40 (9H, s), 1.60-1.62 (6H, d), 3.29-3.47 (7H, m), 4.87-4.93 (1H, m), 7.16-7.20 (1H, m), 7.91-7.97 (2H, m), 8.66 (1H, s), 9.36 (1H, bs).

Mass (m/z): 399.4 (M+H)⁺.

Step (vii): Preparation of N-[(3-aza bicyclo[3.1.0]hexane-6-yl)methyl]-2-Isopropyl-2H-indazole-7-carboxamide Ethanolic hydrogen chloride (23% w/w, 0.33 gram, 9.03 mmole) was added to a solution of N-[(3-tert-butyloxy carbonyl-3-aza bicyclo[3.1.0]hexane-6-yl)methyl]-2-isopropyl-2H-indazole-7-carboxamide (0.36 gram, 0.9 mmole, obtained in the above step) in ethanol (20 mL) at 10° C. The reaction mass was stirred 5 hours at room temperature, while monitoring the progress of the reaction by TLC. After TLC showing completion of the reaction, the reaction mass was concentrated and the slurry, thus obtained, was dissolved in chilled water (15 mL). The pH was adjusted to ~9.5 using aqueous NH₃ solution and the product was extracted with DCM (3×10 mL). The combined organic phase was washed with water (10 mL), brine solution (10 mL) and dried over Na₂SO₄. The organic phase was concentrated under vacuum to afford the title compound (0.22 gram). Yield: 81.48%.

¹H-NMR (δ ppm): 1.03-1.07 (1H, m), 1.43-1.47 (2H, m), 1.60-1.61 (6H, d), 2.69-2.72 (2H, m), 2.87-2.93 (2H, m), 3.27-3.43 (3H, m), 4.88-4.95 (1H, m), 7.15-7.19 (1H, m), 7.89-7.98 (2H, m), 8.63 (1H, s), 9.28 (1H, bs).

Mass (m/z): 299.2 (M+H)⁺.

Preparation 10: Preparation of 1-(3-methoxy propyl) piperidine-4-carboxylic acid hydrazide

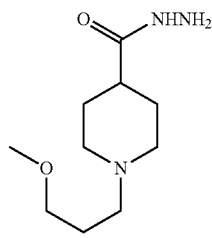

Step (i) Preparation of ethyl 1-(3-methoxy propyl) piperidine-4-carboxylate

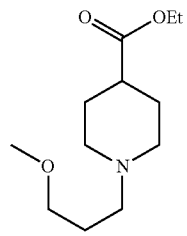 [SMILES: CCOC(=O)C1CCN(CCCOC)CC1]

To a stirred mixture of ethyl isonipecotate (50.5 grams, 321 mmol), K₂CO₃ (59.1 grams, 428 mmol) in acetonitrile at room temperature, 1-bromo-3-methoxypropane (40 mL, 350.0 mmol) was added over a period of 15 minutes. The reaction was heated gradually to reflux and maintained at this temperature for 7 hours. The volatiles were removed under reduced pressure. The crude mass was diluted with water (500 mL) and extracted with DCM (2×500 mL). The combined organic layer was dried over anhydrous $Na_2SO_4$ and the solvent was evaporated under vacuum to obtain above title compound as gummy liquid (65.3 grams). Yield: 90%.

$^1$H-NMR $CDCl_3$ (δ ppm): 1.20 (3H, t, J=7.0 Hz). 1.68-1.74 (4H, m), 1.82-1.85 (2H, m), 1.90-1.95 (2H, m), 2.18-2.22 (2H, m), 2.31-2.35 (2H, m), 2.80-2.83 (2H, m), 3.27 (3H, s), 3.35 (2H, t, J=6.4 Hz), 4.04-4.09 (2H, q).

Mass (m/z): 230.4 (M+H)$^+$.

Step (ii): Preparation of 1-(3-methoxy propyl) piperidine-4-carboxylic acid hydrazide To a stirred solution of ethyl 1-(3-methoxy propyl) piperidine-4-carboxylate (65.3 grams, 285 mmol, obtained in the above step) in methanol (500 mL) hydrazine hydrate (100 mL, 2.0 mmol) was added. The reaction mixture was gradually heated to reflux for 10 hours. The volatiles were removed under reduced pressure. The wet solid was diluted with water (50 mL) and DCM (500 mL). The two layers were separated and the organic layer was dried over anhydrous $Na_2SO_4$. The solvent was removed under reduced pressure to obtain the above title compound as gummy liquid (56.4 grams). Yield: 91.9%.

$^1$H-NMR $CDCl_3$ (δ ppm): 1.70-1.83 (6H, m), 1.90-1.96 (2H, m), 2.01-2.11 (1H, m), 2.36-2.40 (2H, m), 2.90-2.99 (2H, m), 3.31 (3H, s), 3.41 (2H, t, J=6.4 Hz), 4.0 (2H, bs), 6.99 (1H, bs).

Mass (m/z): 216.3 (M+H)$^+$.

Preparation 11: Preparation of 4-aminomethyl-1-(2-fluoro ethyl) piperidine

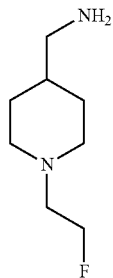

Step (i): Preparation of 2-[4-(N,N-dibenzylamino methyl) piperidin-1-yl]ethanol

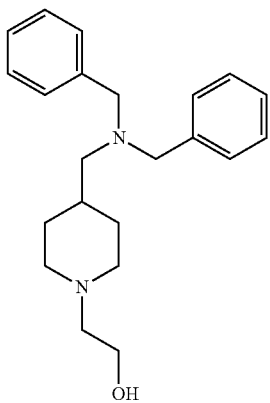 [SMILES: OCCN1CCC(CN(Cc2ccccc2)Cc2ccccc2)CC1]

A mixture of 4-(N,N-dibenzylamino methyl) piperidine (1.0 gram, 3.40 mmol), bromo ethanol (0.64 gram, 5.10 mmole), $K_2CO_3$ (1.0 gram, 7.24 mmole) and acetonitrile (25 mL) was stirred for 16 hours at reflux temperature. The progress of the reaction was monitored by TLC. After TLC showing completion of the reaction, the reaction mass was poured onto chilled water (40 mL). The compound was extracted with ethyl acetate (3×20 mL). The combined organic layer was washed with water (15 mL), brine solution (15 mL) and dried over $Na_2SO_4$. The organic layer was concentrated on rotavacuum to afford the title compound (0.91 gram). Yield: 79.82%.

$^1$H-NMR (δ ppm): 0.83-0.91 (2H, m), 1.14-1.18 (2H, m), 1.50-1.55 (2H, m), 1.65-1.69 (2H, m), 1.82-1.87 (2H, m), 1.94-1.97 (2H, m), 2.14-2.18 (2H, m), 2.72-2.76 (2H, m), 3.27-3.56 (6H, m), 7.19-7.32 (10H, m).

Mass (m/z): 339.3 (M+H)$^+$.

Step (ii): Preparation of 4-(N,N-dibenzylaminomethyl)-1-(2-fluoroethyl) piperidine

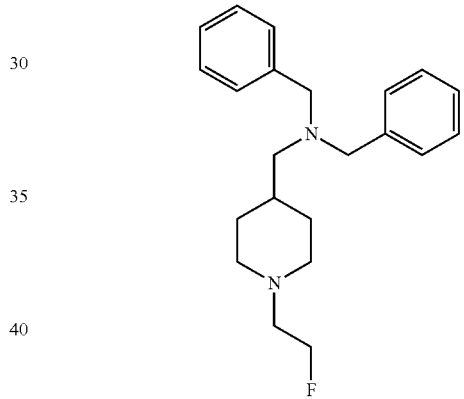

Diethylaminosulfur trifluoride (DAST) (0.6 gram, 3.69 mmol) was added to a stirred solution of 2-[4-(N,N-dibenzylamino methyl) piperidin-1-yl]ethanol (0.5 gram, 1.47 mmol, obtained in the above step) in DCM (20 mL) at −40° C. Then reaction mass temperature was slowly raised to room temperature and stirred over night at the same temperature. The progress of the reaction was monitored by TLC. After completion of the reaction, the mass was quenched in chilled water (20 mL). The pH of the mass was adjusted to ~9.5 using aqueous $NH_3$, the compound was extracted with DCM (3×15 mL). The combined organic phase was washed with water (15 mL), brine solution (15 mL) and dried over $Na_2SO_4$. The organic phase was concentrated on rotavacuum to obtain the crude residue, which was further purified by flash chromatography using EtoAc:n-hexane (5:95) to afford the title compound (0.22 gram). Yield: 44%.

$^1$H-NMR (δ ppm): 1.11-1.14 (2H, m), 1.53-1.59 (3H, m), 1.79-1.82 (2H, m), 2.01-2.05 (2H, m), 2.23-2.26 (2H, m), 2.62-2.69 (2H, m), 2.89-2.92 (2H, m), 3.51 (4H, s), 7.20-7.36 (10H, m).

Mass (m/z): 341.4 (M+H)$^+$.

Step (iii): Preparation of 4-aminomethyl-1-(2-fluoro ethyl) piperidine

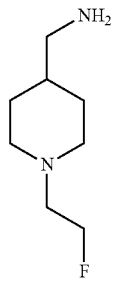

A mixture of 4-(N,N-dibenzylaminomethyl)-1-(2-fluoroethyl) piperidine (0.22 gram, 0.647 mmole, obtained in the above step), 10% palladium carbon (0.22 gram, 100% w/w) and methanol (20 mL) was stirred for over night (10 hours) at room temperature under hydrogen gas atmosphere. The progress of reaction was monitored by TLC. After completion of the reaction, the reaction mass was filtered through celite bed and the filtrate was concentrated under vacuum to afford the title compound (0.1 gram). Yield: 97.08%.

$^1$H-NMR (δ ppm): 1.03-1.06 (2H, m), 1.59-1.62 (2H, m), 1.82-1.85 (2H, m), 2.30-2.33 (2H, m), 2.37-2.41 (1H, m), 2.80-2.84 (2H, m), 3.00-3.50 (6H, m).

Mass (m/z): 161.2 (M+H)$^+$.

Preparation 12: Preparation of 2-aminomethyl-N-benzyl morpholine

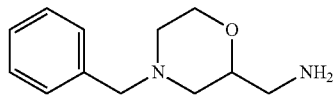 [SMILES: NCC1CN(Cc2ccccc2)CCO1]

Step (i) Preparation of 2-benzylaminoethanol

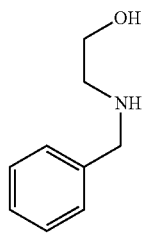 [SMILES: OCCNCc1ccccc1]

A mixture of benzaldehyde (10.0 grams, 94.3 mmol), 2-aminoethanol (6.9 grams, 113.2 mmol), NaHCO$_3$ (12.0 grams, 143.3 mmol) and methanol (188 mL) was heated to reflux for 4 hours and cooled to 0° C. Sodiumborohydride (4.2 grams, 113.2 mmol) was added portion wise to the stirred reaction mass over a period of 0.5 hour. The reaction mixture was gradually warmed to room temperature and stirred for 1 hour. The insoluble materials were removed by filtration and the filtrate was evaporated under vacuum and the crude product thus obtained was purified by silica gel column to obtain above titled compound (9.2 grams). Yield: 64%.

$^1$H-NMR CDCl$_3$ (δ ppm): 2.14 (2H, bs), 2.82 (2H, t, J=4.8 Hz), 3.68 (2H, t, J=4.8 Hz), 3.83 (2H, s), 7.25-7.31 (1H, m), 7.32-7.40 (4H, m).

Mass (m/z): 152.3 (M+H)$^+$.

Step (ii) Preparation of N-benzyl-2-chloromethylmorpholine

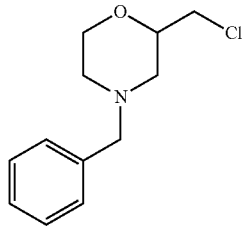 [SMILES: ClCC1CN(Cc2ccccc2)CCO1]

A mixture of 2-benzylaminoethanol (5.1 grams, 33.7 mmol) and (±)-epichlorohydrin (2.91 mL, 37.1 mmol) were stirred at room temperature for 12 hours. Concentrated sulphuric acid (12.9 mL, 242.6 mmol) was added drop wise over a period of 15 minutes to the cooled (0° C.) reaction mass. The reaction mixture was gradually warmed to room temperature then heated at 130° C. for 1 hour. The cooled (0° C.) reaction mass was quenched by slow addition of cold water followed by the addition of 40% aqueous NaOH solution to basify the reaction mass to pH 10. The basified reaction mass was extracted with DCM, the combined organic layer was dried over anhydrous Na$_2$SO$_4$ and the solvent was evaporated under reduced pressure and the crude mass was purified by silica gel column chromatography to obtain above titled compound (6.7 grams). Yield: 88%.

$^1$H-NMR CDCl$_3$ (δ ppm): 1.88-2.08 (1H, m), 2.21 (1H, ddd, J=3.3, 11.3, 14.5 Hz), 2.60-2.70 (1H, m), 2.80-2.90 (1H, m), 3.45-3.56 (4H, m), 3.67-3.83 (2H, m), 3.87-3.96 (1H, m), 7.25-7.31 (1H, m), 7.31-7.40 (4H, m).

Mass (m/z): 226.1, 228.1 (M+H)$^+$.

Step (iii) Preparation of 2-azidomethyl-N-benzyl morpholine

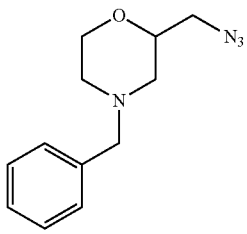 [SMILES: [N-]=[N+]=NCC1CN(Cc2ccccc2)CCO1]

A mixture of N-benzyl-2-chloromethylmorpholine (100 mg, 0.44 mmol, obtained in the above step), NaN$_3$ (114.4 mg, 1.76 mmol), tetrabutylammonium iodide (16.7 mg, 0.044 mmol) and DMF was heated to 110° C. and was stirred at this temperature for 12 hours. The reaction mass was cooled to room temperature, diluted with water and extracted with solvent ether. The combined organic layer was dried over anhydrous Na$_2$SO$_4$ and the volatiles were removed under reduced pressure to obtain the above titled compound (101.5 mg).

¹H-NMR CDCl₃ (δ ppm): 1.98-2.10 (1H, m), 2.27 (1H, ddd, J=2.8, 11.2, 13.9 Hz), 2.65-2.75 (1H, m), 2.85-2.90 (1H, m), 3.26-3.38 (1H, m), 3.50-3.60 (3H, m), 3.70-3.82 (2H, m), 3.92-3.98 (1H, m), 7.30-7.35 (1H, m), 7.35-7.42 (4H, m).

Mass (m/z): 233.2 (M+H)⁺.

Step (iv) Preparation of 2-aminomethyl-N-benzyl morpholine

To a stirred solution of 2-azidomethyl-N-benzyl morpholine (100 mg, 0.43 mmol, obtained in the above step) in THF (1.7 mL) cooled at 0° C., triphenylphosphine (124.3 mg, 0.47 mmol) and water (0.03 mL, 1.6 mmol) was added. The reaction mixture was gradually warmed to room temperature stirred for 12 hours. The volatiles were removed under reduced pressure and the crude mass was diluted with hydrochloride (2N, 1 mL) and extracted with ether. The aqueous layer was cooled to 0° C. and basified with aqueous NaHCO₃ solution to pH 8-9 and extracted with DCM. The combined organic layer was dried over anhydrous Na₂SO₄ and the solvent was removed under reduced pressure to obtain the above titled compound (31.6 mg). Yield: 35% for above two steps.

¹H-NMR CDCl₃ (δ ppm): 1.87-1.95 (1H, m), 2.20 (1H, ddd, J=3.2, 11.4, 14.6 Hz), 2.65-2.80 (4H, m), 3.48-3.60 (3H, m), 3.68-3.76 (1H, m), 3.90-3.96 (11, m), 7.28-7.32 (1H, m), 7.32-7.41 (4H, m).

Mass (m/z): 207.3 (M+H)⁺.

Preparation 13: Preparation of 2-Aminomethyl-4-(tetrahydropyran-4-yl methyl) morpholine Step (i): Preparation of (4-Benzyl morpholin-2-yl methyl) carbamic acid tert-butyl ester

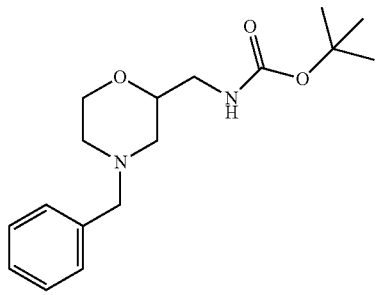 [SMILES: CC(C)(C)OC(=O)NCC1CN(Cc2ccccc2)CCO1]

A mixture of 2-aminomethyl-N-benzyl morpholine (44 grams, 0.213 mole, obtained in the preparation 12), BOC anhydride (58.8 mL, 0.256 mole), TEA (60 mL, 0.427 mole) and DCM (500 mL) was stirred for 4 hours at room temperature. The progress of reaction was monitored by TLC. After completion of the reaction (TLC), reaction mass was poured onto chilled water (1000 mL) and extracted with solvent DCM (500 mL×4). The combined organic layer was dried over anhydrous Na₂SO₄ and the solvent was evaporated under reduced pressure and the crude mass was purified by silica gel column chromatography to obtain above titled compound (49.17 grams). Yield: 75%.

¹H-NMR (δ ppm): 1.32 (9H, s), 1.66-3.75 (11H, m), 6.78-6.81 (1H, m), 7.21-7.32 (5H, m).

Mass (m/z): 307.4 (M+H)⁺.

Step (ii): Preparation of Morpholin-2-ylmethyl carbamic acid tert-butyl ester

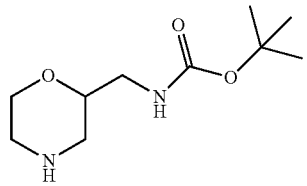

A mixture of (4-benzyl morpholin-2-yl methyl) carbamic acid tert-butyl ester (29.0 grams, 0.094 mole, obtained in the above step), 10% palladium carbon (29.0 grams, 100% w/w) and methanol (500 mL) was stirred for 5 hours at room temperature under hydrogen gas atmosphere. The progress of reaction was monitored by TLC. After completion of the reaction, the reaction mass was filtered through celite bed and the filtrate was concentrated under vacuum to afford the compound (19.38 grams). Yield: 94%.

¹H-NMR (δ ppm): 1.35 (9H, s), 2.13-2.88 (10H, m), 6.76-6.79 (2H, m).

Mass (m/z): 216.9 (M+H)⁺.

Step (iii): Preparation of [4-(Tetrahydro pyran-4-carbonyl) morpholin-2-yl methyl]carbamic acid tert-butyl ester

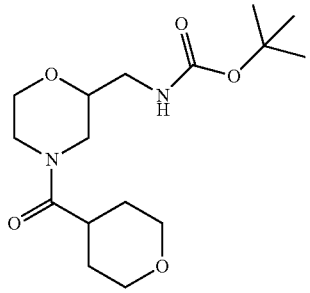 [SMILES: CC(C)(C)OC(=O)NCC1CN(C(=O)C2CCOCC2)CCO1]

A solution of tetrahydropyran-4-carboxylic acid (0.6 gram, 4.61 mmol) and CDI (0.9 gram, 5.55 mmol) in DCM (20 mL) was stirred for 1 hour at room temperature. A solution of morpholin-2-ylmethyl-carbamic acid tert-butyl ester (1.0 gram, 4.58 mmol, obtained in the above step) in DCM (10 mL) was added. After stirring for 24 hours, the TLC revealed completion of the reaction. The reaction mass was poured onto cold water and extracted with DCM, the combined organic layer was dried over anhydrous Na₂SO₄ and the solvent was evaporated under reduced pressure and the crude mass was purified by silica gel column chromatography to obtain above titled compound (1.3 grams). Yield: 86%.

¹H-NMR (δ ppm): 1.39 (9H, s), 1.40-4.27 (18H, m), 6.92-6.94 (1H, m).

Mass (m/z): 329.3 (M+H)⁺.

Step (iv): Preparation of (2-Aminomethyl morpholin-4-yl) (tetrahydro-pyran-4-yl) methanone

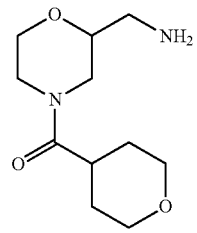 [SMILES: NCC1CN(C(=O)C2CCOCC2)CCO1]

Ethanolic hydrogen chloride (23% w/w, 1.44 gram, 39.63 mmole) was added to a solution of [4-(tetrahydro pyran-4-carbonyl) morpholin-2-yl methyl]carbamic acid tert-butyl ester (1.3 grams, 3.96 mmole, obtained in above step) in ethanol (30 mL) at 10° C. The reaction mass was stirred for 15 hours at room temperature at which time TLC revealed the completion of the reaction. The reaction mass was concentrated and the slurry, thus obtained, was dissolved in chilled water (15 mL). The pH was adjusted to ~9.5 using aqueous NH$_3$ solution and the product was extracted with DCM (3×10 mL). The combined organic phase was washed with water (10 mL), brine solution (10 mL) and dried over Na$_2$SO$_4$. The organic phase was concentrated under vacuum to afford the title compound (0.8 gram). Yield: 88.88%
1H-NMR (δ ppm): 1.57-4.30 (20H, m).
Mass (m/z): 229.2 (M+H)$^+$.

Step (v): Preparation of 2-Aminomethyl-4-(tetrahydropyran-4-yl methyl) morpholine To the stirred solution of (2-aminomethyl morpholin-4-yl) (tetrahydro-pyran-4-yl) methanone (0.8 gram, 3.50 mmols, obtained in the above step) in THF (20 mL) cooled at 0° C., a solution of LiAlH$_4$ (1M, 6.8 mL) in THF was added over a period of 15 minutes. The reaction mixture was gradually warmed to room temperature and then it was refluxed for 14 hours. The reaction mass was cooled to 0° C. and added water (2 mL) and EtoAc (20 mL). After stirring for 15 minutes, the crude mass was filtered through a pad of celite. The celite pad was washed with EtoAc. The filtrate was dried over anhydrous sodium sulphate (Na$_2$SO$_4$) and the volatiles were removed under reduced pressure to obtain the above titled compound (0.62 gram). Yield: 82.66%.
$^1$H-NMR (δ ppm): 1.07-3.98 (22H, m).
Mass (m/z): 215.3 (M+H)$^+$.

Preparation 14: Preparation of 2-methoxy-2-methyl propyl toluene-4-sulfonate

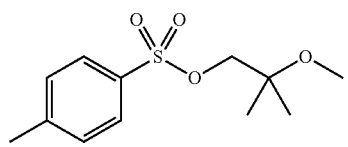

Step (i): Preparation of 2-methoxy-2-methyl propan-1-ol

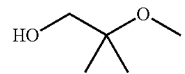

A solution of isobutyleneoxide (1.0 gram, 13.88 mmol) and indium chloride (0.61 gram, 2.757 mmol) in methanol (20 mL) was stirred at 50° C. for 5 hours while monitoring the progress of the reaction by TLC. After completion of the reaction, the reaction mass was concentrated under vacuum and the residue was diluted with dichloromethane (50 mL). The organic layer was washed with saturated sodium bicarbonate solution (10 mL) and dried over Na$_2$SO$_4$. The organic phase was concentrated under vacuum to afford the title compound (0.18 gram). Yield: 12.5%.
$^1$H-NMR (δ ppm): 1.16 (6H, s), 1.94-1.97 (1H, t), 3.23 (3H, s), 3.42-3.44 (2H, d).
Mass (m/z): 105.1 (M+H)$^+$.

Step (ii): Preparation of 2-methoxy-2-methyl propyl toluene-4-sulfonate p-Toluene sulfonyl chloride (0.36 gram, 1.889 mmol) was added to a stirred solution of 2-methoxy-2-methyl propan-1-ol (0.18 gram, 1.73 mmol, obtained in the above step) in pyridine (2.0 mL) portion wise at 0° C. The reaction mass was stirred for 48 hours at room temperature under nitrogen atmosphere, while monitoring the progress of the reaction by TLC. After completion of the reaction, the reaction mass was poured onto chilled 1 N solution of aqueous HCl (10 mL) and the product was extracted with EtOAc (3×5 mL). The combined organic layer was washed with water (5 mL), brine solution (5 mL) and dried over Na$_2$SO$_4$. The organic layer was concentrated under vacuum to afford the title compound (0.26 gram). Yield: 12.5%.
$^1$H-NMR (δ ppm): 1.13 (6H, s), 2.45 (3H, s), 3.14 (3H, s), 3.85 (2H, s), 7.33-7.35 (2H, d, J=8.00 Hz), 7.79-7.81 (2H, d, J=8.00 Hz).
Mass (m/z): 259.2 (M+H)$^+$.

Preparation 15: Preparation of N-[(piperidine-4-yl) methyl]-2-Isopropyl-2H-indazole-7-carboxamide

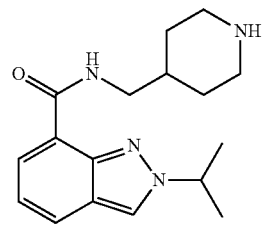 [SMILES: CC(C)n1cc2cccc(C(=O)NCC3CCNCC3)c2n1]

Step (i): Preparation of N-[(1-tert-butyloxy carbonyl piperidin-4-yl)methyl]-2-isopropyl-2H-indazole-7-carboxamide

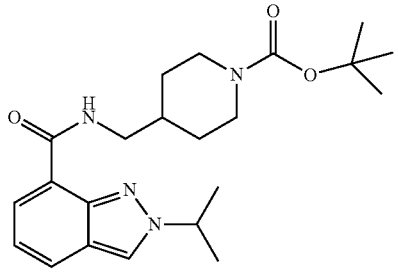 [SMILES: CC(C)n1cc2cccc(C(=O)NCC3CCN(C(=O)OC(C)(C)C)CC3)c2n1]

A solution of 2-isopropyl-2H-indazole-7-carboxylic acid (0.4 gram, 1.96 mmol, obtained in preparation 1) and carbonyldiimidazole (0.41 gram, 2.53 mmol) in DCM (10 mL) was stirred for 3 hours at room temperature. A solution of with tert-butyl 4-aminomethyl piperidine-1-carboxylate (0.47 gram, 2.20 mmol) in DCM (5 mL) was added. The reaction mass was stirred over night (12 hours) at room temperature under nitrogen atmosphere, while monitoring the progress of the reaction by TLC. After completion of the reaction, the reaction mass was washed with chilled water (5 mL), brine solution (5 mL) and dried over $Na_2SO_4$. The organic phase was concentrated on rotavacuum to obtain the crude residue, which was further purified by flash chromatography using EtoAc:n-hexane (50:50) to afford the title compound (0.59 gram). Yield: 75.64%.

$^1$H-NMR (δ ppm): 1.13-1.16 (1H, m), 1.41 (9H, s), 1.57-1.59 (6H, d), 1.71-1.75 (4H, m), 2.70-2.76 (2H, m), 3.32-3.36 (2H, m), 3.95-3.97 (2H, m), 4.87-4.94 (1H, m), 7.16-7.19 (1H, m), 7.91-7.97 (2H, m), 8.65 (1H, s), 9.25 (1H, bs).

Mass (m/z): 401.3 (M+H)$^+$.

Step (ii): Preparation of N-[(piperidin-4-yl)methyl]-2-Isopropyl-2H-indazole-7-carboxamide Ethanolic hydrogen chloride (23% w/w, 0.33 gram, 9.08 mmole) was added to a solution of N-[(1-tert-butyloxy carbonyl piperidin-4-yl)methyl]-2-isopropyl-2H-indazole-7-carboxamide (0.58 gram, 1.45 mmol, obtained in the above step) in ethanol (20 mL) at 10° C. The reaction mass was stirred 5 hours at room temperature, while monitoring the progress of the reaction by TLC. After completion of the reaction, it was concentrated under reduced pressure. The slurry, thus obtained, was dissolved in chilled water (15 mL). The pH was adjusted to ~9.5 using aqueous $NH_3$ solution and the product was extracted with DCM (3×10 mL). The combined organic phase was washed with water (10 mL), brine solution (10 mL) and dried over $Na_2SO_4$. The organic phase was concentrated under vacuum to afford the title compound (0.34 gram). Yield: 79.06%.

$^1$H-NMR (δ ppm): 1.18-1.24 (4H, m), 1.57-1.59 (6H, d), 1.66-1.73 (4H, m), 2.49-2.55 (2H, m), 2.96-3.01 (2H, m), 4.87-4.94 (1H, m), 7.16-7.20 (1H, m), 7.91-7.97 (2H, m), 8.65 (1H, s), 9.26-9.28 (1H, t).

Mass (m/z): 301.3 (M+H)$^+$.

Example 1: Preparation of N—[(N-tetrahydropyran-4-yl methyl) piperidin-4-yl methyl]-2-isopropyl-2H-indazole-7-carboxamide fumarate

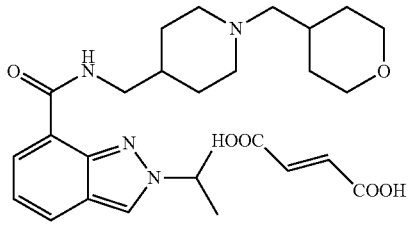

Step (i): Preparation of N—[(N-tetrahydropyran-4-yl methyl) piperidin-4-yl methyl]-2-isopropyl-2H-indazole-7-carboxamide

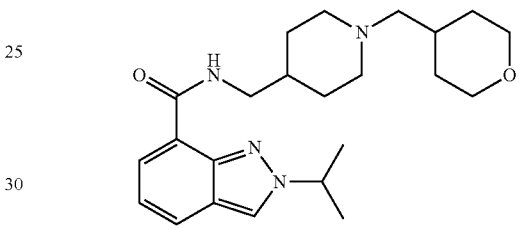

To a stirred solution of 2-isopropyl-2H-indazole-7-carboxylic acid (1.25 grams, 6.12 mmol, obtained in the preparation 1) in DCM (24 mL) cooled at 0° C. was added diisopropylethylamine (1.59 mL, 9.2 mmol) and O-(Benzotriazol-1-yl)-N,N,N',N'-tetramethyluronium tetrafluoroborate (TBTU) (2.16 grams, 6.7 mmols). After stirring for 15 minutes, 4-aminomethyl-[N-(tetrahydropyran-4-yl)methyl] piperidine (1.56 grams, 7.34 mmol, obtained in the preparation 3) was added. The reaction mixture was gradually warmed to room temperature and stirred for 16 hours. The reaction mixture was diluted with DCM and water. The two layers were separated, the organic layer was washed with brine, dried over anhydrous $Na_2SO_4$ and the volatiles were removed under reduced pressure and the crude mass was purified by silica gel column chromatography to obtain the titled compound (1.26 grams). Yield: 52%.

$^1$H-NMR $CDCl_3$ (δ ppm): 1.16-1.30 (2H, m), 1.38-1.50 (2H, m), 1.68 (6H, d, J=6.6 Hz), 1.60-1.79 (4H, m), 1.80-1.90 (2H, m), 1.90-2.00 (2H, m), 2.16 (2H, d, J=7.0 Hz), 2.85-2.95 (2H, m), 3.37 (2H, t, J=11.5 Hz), 3.45-3.52 (2H, m), 3.92-4.00 (2H, m), 4.75-4.88 (1H, m), 7.20 (1H, t, J=7.6 Hz), 7.80 (1H, d, J=8.2 Hz), 8.05 (1H, s), 8.25 (1H, d, J=7.0 Hz), 9.38 (bs, 1H).

Mass (m/z): 399.4 (M+H)$^+$.

Step (ii): Preparation of N—[(N-tetrahydropyran-4-yl methyl) piperidin-4-yl methyl]-2-isopropyl-2H-indazole-7-carboxamide fumarate To the stirred solution of N—[(N-tetrahydropyran-4-yl methyl) piperidin-4-yl methyl]-2-isopropyl-2H-indazole-7-carboxamide (1.25 grams, 3.13 mmols, obtained in the above step) in ethanol (12 mL) fumaric acid (0.34 grams, 2.98 mmols) was added. The reaction mass was stirred for 1 hour at room temperature and the volatiles were removed under reduced pressure to obtain a crude mass which was triturated with ether and filtered which yielded the above titled compound (1.54 grams). Yield: 95%.

¹H-NMR DMSO-d₆ (δ ppm): 1.00-1.18 (2H, m), 1.31-1.42 (2H, m), 1.59 (6H, d, J=6.5 Hz), 1.50-1.68 (3H, m), 1.68-1.85 (3H, m), 2.00-2.10 (2H, m), 2.25 (2H, d, J=6.9 Hz), 2.90-3.0 (2H, m), 3.25 (2H, t, J=11.3 Hz), 3.36 (2H, t, J=5.8 Hz), 3.75-3.82 (2H, m), 4.84-4.96 (1H, m), 6.57 (2H, s), 7.18 (1H, t, J=7.6 Hz), 7.93 (1H, d, J=8.2 Hz), 7.97 (1H, d, J=6.9 Hz), 8.65 (1H, s), 9.27 (1H, bs).

Mass (m/z): 399.4 (M+H)⁺.

Example 2: Preparation of N—[(N-tetrahydropyran-4-yl methyl) piperidin-4-yl methyl]-2-ethyl-2H-indazole-7-carboxamide fumarate

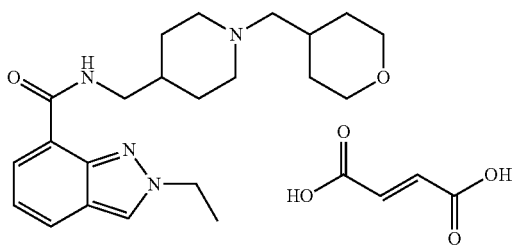

Step (i): Preparation of N—[(N-tetrahydropyran-4-yl methyl) piperidin-4-yl methyl]-2-ethyl-2H-indazole-7-carboxamide

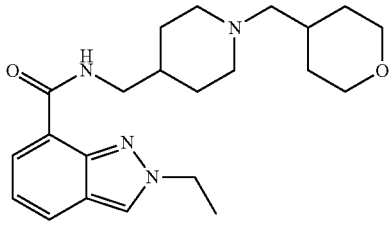 [SMILES: CCn1cc2cccc(C(=O)NCC3CCN(CC4CCOCC4)CC3)c2n1]

To a stirred solution of 2-ethyl-2H-indazole-7-carboxylic acid (0.38 gram, 2.01 mmol, obtained in the preparation 2) in DCM (8 mL) cooled at 0° C. was added diisopropylethylamine (0.52 mL, 3.1 mmol) and TBTU (0.71 gram, 2.2 mmol, obtained in the preparation 3). After stirring for 15 minutes, 4-Aminomethyl-1-(tetrahydropyran-4-yl methyl) piperidine (0.51 gram, 2.41 mmol, obtained in the preparation 3) was added. The reaction mixture was gradually warmed to room temperature and stirred for 16 hours. The reaction mixture was diluted with DCM and water. The two layers were separated, the organic layer was washed with brine, dried over anhydrous Na₂SO₄ and the volatiles were removed under reduced pressure and the crude mass was purified by silica gel column chromatography to obtain the titled compound (0.53 gram). Yield: 68%.

¹H-NMR CDCl₃ (δ ppm): 1.20-1.32 (2H, m), 1.36-1.48 (2H, m), 1.67 (3H, t, J=7.3 Hz), 1.60-1.78 (4H, m), 1.78-1.85 (2H, m), 1.88-1.97 (2H, m), 2.16 (2H, d, J=7.0 Hz), 2.82-2.92 (2H, m), 3.32-3.43 (2H, m), 3.45-3.52 (2H, m), 3.90-4.00 (2H, m), 4.51 (2H, q), 7.20 (1H, t, J=7.2 Hz), 7.80 (1H, d, J=8.2 Hz), 8.0 (1H, s), 8.25 (1H, d, J=7.0 Hz), 9.31 (1H, bs).

Mass (m/z): 385.3 (M+H)⁺.

Step (ii): Preparation of N—[(N-tetrahydropyran-4-yl methyl) piperidin-4-yl methyl]-2-ethyl-2H-indazole-7-carboxamide fumarate To the stirred solution of N—[(N-tetrahydropyran-4-yl methyl) piperidin-4-yl methyl]-2-ethyl-2H-indazole-7-carboxamide (0.53 gram, 1.38 mmol, obtained in the above step) in ethanol (6 mL), fumaric acid (0.15 gram, 1.31 mmol) was added. The reaction mass was stirred for 1 hour at room temperature and the volatiles were removed under reduced pressure to obtain a crude mass which was triturated with ether and filtered to obtain the above titled compound (0.6 gram). Yield: 92%.

¹H-NMR DMSO-d₆ (δ ppm): 1.00-1.15 (2H, m), 1.28-1.42 (2H, m), 1.54 (3H, t, J=7.3 Hz), 1.55-1.65 (3H, m), 1.65-1.80 (3H, m), 1.98-2.10 (2H, m), 2.25 (2H, d, J=6.9 Hz), 2.90-3.00 (2H, m), 3.25 (2H, t, J=11.1 Hz), 3.35 (2H, t, J=5.9 Hz), 3.75-3.85 (2H, m), 4.53 (2H, q), 6.57 (2H, s), 7.18 (1H, t, J=7.7 Hz), 7.94 (1H, d, J=8.2 Hz), 7.98 (1H, d, J=7.0 Hz), 8.62 (1H, s), 9.23 (1H, bs), 13.00 (1H, bs).

Mass (m/z): 385.3 (M+H)⁺.

Example 3: Preparation of N—[N-(3-methoxy propyl)-3-aza bicyclo[3.1.0]hexane-6-yl methyl]-2-isopropyl-2H-indazole-7-carboxamide oxalate

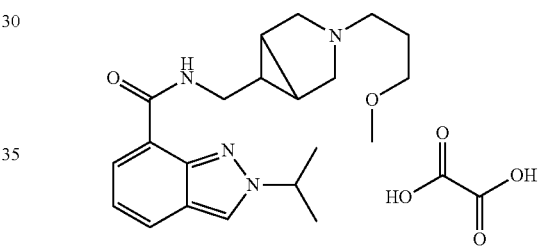

Step (i): Preparation of N—[N-(3-methoxy propyl)-3-aza bicyclo[3.1.0]hexane-6-yl methyl]-2-isopropyl-2H-indazole-7-carboxamide

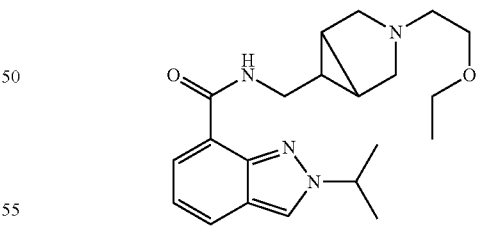

To a stirred solution of 2-isopropyl-2H-indazole-7-carboxylic acid (2.11 grams, 10.33 mmol, obtained in the preparation 1) in DCM (42.0 mL) cooled at 0° C., diisopropylethylamine (DIPEA) (2.70 mL, 15.49 mmol), 6-aminomethyl-3-(3-methoxypropyl)-3-azabicyclo[3.1.0]hexane (2.09 grams, 11.36 mmol, obtained in the preparation 5) and TBTU (3.64 grams, 11.36 mmol) were added. The reaction mixture was gradually warmed to room temperature and stirred for 16 hours. The reaction mass was diluted with DCM and water and the two layers were separated. The organic layer was dried over anhydrous Na₂SO₄ and the solvent was removed under reduced pressure to obtain a crude mass which was purified by silica gel column (100-200 mesh) chromatography which afforded the above titled compound (2.01 grams). Yield: 52%.

¹H-NMR CDCl₃ (δ ppm): 1.44-1.48 (2H, m), 1.50-1.60 (1H, m), 1.71 (6H, d, J=6.6 Hz), 1.70-1.80 (2H, m), 2.30-2.40 (2H, m), 2.47 (2H, t, J=7.2 Hz), 3.08 (2H, d, J=8.6 Hz), 3.31 (3H, s), 3.38 (2H, t, J=6.5 Hz), 3.49 (2H, t, J=7.5 Hz), 4.78-4.90 (1H, m), 7.20 (1H, t, J=7.6 Hz), 7.80 (1H, d, J=8.2 Hz), 8.05 (1H, s), 8.24 (1H, d, J=7.0 Hz), 9.34 (1H, bs).

Mass (m/z): 371.3 (M+H)⁺.

Step (ii): Preparation of N—[N-(3-methoxy propyl)-3-aza bicyclo[3.1.0]hexane-6-yl methyl]-2-isopropyl-2H-indazole-7-carboxamide oxalate To a stirred solution of N—[N-(3-methoxy propyl)-3-aza bicyclo[3.1.0]hexane-6-yl methyl]-2-isopropyl-2H-indazole-7-carboxamide (2.0 grams, 5.40 mmol, obtained in the above step) in ethanol (22 mL) cooled at 0° C., oxalic acid (0.46 gram, 5.13 mmol) was added. The reaction mass stirred for 1 hour and the volatiles were removed under reduced pressure and the residual mass was further recrystallized from C₃H₇OH, water system which afforded the above titled compound as white crystalline solid (2.21 grams). Yield: 93.9%.

¹H-NMR DMSO-d₆ (δ ppm): 1.36-1.45 (1H, m), 1.59 (6H, d, J=6.3 Hz), 1.72-1.88 (4H, m), 3.05-3.15 (4H, m), 3.19 (3H, s), 3.22-3.40 (6H, m), 4.88-5.00 (1H, m), 7.18 (1H, t, J=7.6 Hz), 7.94 (1H, d, J=8.2 Hz), 7.98 (1H, d, J=6.8 Hz), 8.67 (1H, s), 9.29 (1H, bs).

Mass (m/z): 371.3 (M+H)⁺.

Example 4: Preparation of N—[N-(3-methoxy propyl) piperidin-4-ylmethyl]-2-ethyl-2H-indazole-7-carboxamide fumarate

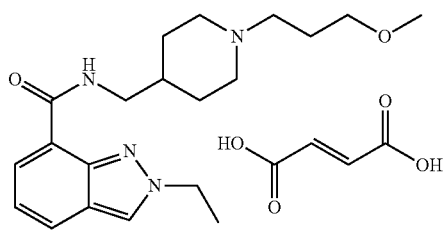

Step (i): Preparation of N—[N-(3-methoxy propyl) piperidin-4-ylmethyl]-2-ethyl-2H-indazole-7-carboxamide

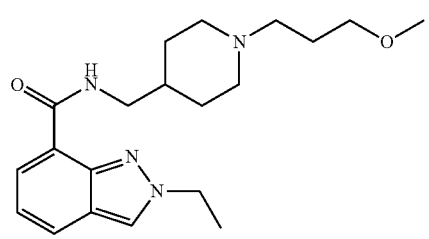 [SMILES: CCn1cc2cccc(C(=O)NCC3CCN(CCCOC)CC3)c2n1]

To a stirred solution of 2-ethyl-2H-indazole-7-carboxylic acid (101.2 mg, 0.53 mmol, obtained in the preparation 2) in DCM (5.3 mL) cooled at 0° C., DIPEA (0.14 mL, 0.79 mmol), 4-aminomethyl-1-(3-methoxypropyl) piperidine (119.0 mg, 0.64 mmol) and TBTU (187.8 mg, 0.58 mmol) were added. The reaction mass was gradually warmed to room temperature and stirred for 16 hours. The reaction mass was diluted with DCM, washed with water; the organic layer was dried over anhydrous Na₂SO₄ and the solvent was removed under reduced pressure to obtain the crude mass which was purified by silica gel column chromatography which afforded the above titled compound (132.8 mg). Yield: 69%.

¹H-NMR CDCl₃ (δ ppm): 1.37-1.48 (2H, m), 1.67 (3H, t, J=7.3 Hz), 1.70-1.80 (3H, m), 1.80-1.90 (2H, m), 1.90-2.00 (2H, m), 2.35-2.43 (2H, m), 2.90-3.00 (2H, m), 3.32 (3H, s), 3.41 (2H, t, J=6.4 Hz), 3.49 (2H, t, J=6.2 Hz), 4.52 (2H, q), 7.20 (1H, t, J=7.7 Hz), 7.80 (1H, d, J=8.2 Hz), 8.03 (1H, s), 8.25 (1H, d, J=7.0 Hz), 9.32 (1H, bs).

Mass (m/z): 359.3 (M+H)⁺.

Step (ii): Preparation of N—[N-(3-methoxy propyl) piperidin-4-ylmethyl]-2-ethyl-2H-indazole-7-carboxamide fumarate To the stirred solution of N—[N-(3-methoxy propyl) piperidin-4-ylmethyl]-2-ethyl-2H-indazole-7-carboxamide (128.5 mg, 0.36 mmol, obtained in the above step) in ethanol (3.6 mL) cooled at 0° C., fumaric acid (39.5 mg, 0.34 mmol) was added. The reaction mass was gradually warmed to room temperature and stirred for 1 hour. The volatiles were removed under reduced pressure and the crude mass was triturated several times with solvent ether which afforded the above titled compound as hygroscopic solid (140.2 mg). Yield: 86%.

¹H-NMR DMSO-d₆ (δ ppm): 1.32-1.48 (2H, m), 1.55 (3H, t, J=7.2 Hz), 1.60-1.85 (5H, m), 2.15-2.32 (2H, m), 2.53-2.65 (2H, m), 3.02-3.12 (2H, m), 3.19 (3H, s), 3.31 (2H, t, J=6.1 Hz), 3.37 (2H, t, J=6.0 Hz), 4.53 (2H, q), 6.52 (2H, s), 7.18 (1H, t, J=7.7 Hz), 7.94 (1H, d, J=8.2 Hz), 7.98 (1H, d, J=6.9 Hz), 8.62 (1H, s), 9.23 (1H, bs).

Mass (m/z): 359.3 (M+H)⁺.

Example 5: Preparation of N—[N-(3-methoxy propyl)-3-aza bicyclo[3.1.0]hexane-6-yl methyl]-2-ethyl-2H-indazole-7-carboxamide oxalate

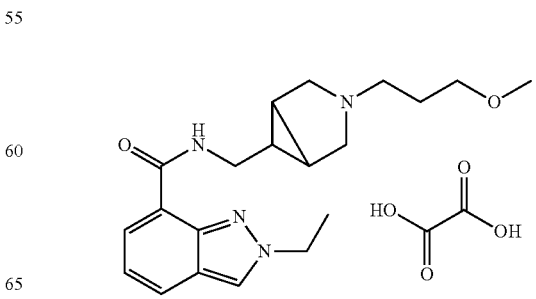

Step (i): Preparation of N—[N-(3-methoxy propyl)-3-aza bicyclo[3.1.0]hexane-6-yl methyl]-2-ethyl-2H-indazole-7-carboxamide

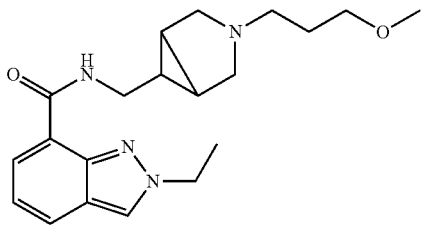 [SMILES: CCn1cc2cccc(C(=O)NCC3C4CN(CCCOC)CC34)c2n1]

To the stirred solution of 2-ethyl-2H-indazole-7-carboxylic acid (104.8 mg, 0.55 mmol, obtained in the preparation 2) in DCM (5.5 mL) cooled at 0° C., DIPEA (0.14 mL, 0.82 mmol), 6-aminomethyl-3-(3-methoxypropyl)-3-azabicyclo[3.1.]hexane (121.8 hexane, 0.66 methyol, obtained in the preparation 5) and TBTU (194.5 mg, 0.60 mmol) were added. The reaction mixture was gradually warmed to room temperature and stirred for 16 hours. The reaction mass was diluted with DCM and water and the two layers were separated. The organic layer was dried with anhydrous $Na_2SO_4$ and the solvent was removed under reduced pressure. The crude mass, thus obtained, was purified by silica gel column chromatography which afforded above titled compound (80.4 mg). Yield: 41%.

$^1$H-NMR $CDCl_3$ (δ ppm): 1.42-1.48 (2H, m), 1.52-1.62 (1H, m), 1.67 (3H, t, J=7.3 Hz), 1.68-1.80 (2H, m), 2.30-2.40 (2H, m), 2.46-2.58 (2H, m), 3.02-3.12 (2H, m), 3.31 (3H, s), 3.38 (2H, t, J=6.5 Hz), 3.47 (2H, t, J=6.4 Hz), 4.54 (2H, q), 7.20 (1H, t, J=7.6 Hz), 7.80 (1H, d, J=8.2 Hz), 8.03 (1H, s), 8.24 (1H, d, J=7.0 Hz), 9.28 (1H, bs).

Mass (m/z): 357.3 $(M+H)^+$.

Step (ii): Preparation of N—[N-(3-methoxy propyl)-3-aza bicyclo[3.1.0]hexane-6-yl methyl]-2-ethyl-2H-indazole-7-carboxylic acid To the stirred solution of N—[N-(3-methoxy propyl)-3-aza bicyclo[3.1.0.]hexane-6-yl methyl]-2-ethyl-2H-indazole-7-carboxamide (80.0 mg, 0.22 mmol, obtained in the above step) in ethanol (2.2 mL) cooled at 0° C., oxalic acid (19.2 mg, 0.213 mmol) was added. The reaction mass was stirred for 1 hour at room temperature and the solvent was removed under reduced pressure to obtain a gummy liquid which was triturated with solvent ether, which afforded above titled compound as white hygroscopic salt (72.9 mg). Yield: 76%.

$^1$H-NMR DMSO-$d_6$ (δ ppm): 1.30-1.50 (m, 4H), 1.60-1.90 (4H, m), 2.90-3.00 (2H, m), 3.18 (3H, s), 3.30-3.70 (8H, m), 4.53 (2H, bs), 7.18 (1H, bs), 7.96 (2H, bs), 8.63 (1H, s), 9.23 (1H, bs).

Mass (m/z): 357.3 $(M+H)^+$.

Example 6: Preparation of N—[N-(3-hydroxy-2,2-dimethyl propyl) piperidin-4-ylmethyl]-2-isopropyl-2H-indazole-7-carboxamide L(+) Tartarate

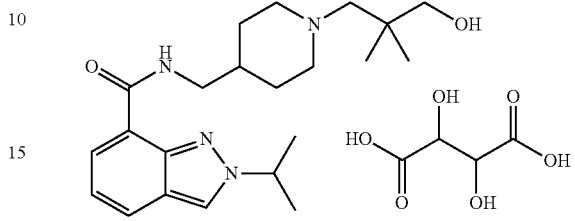

Step (i): Preparation of N—[N-(3-hydroxy-2,2-dimethyl propyl) piperidin-4-ylmethyl]-2-isopropyl-2H-indazole-7-carboxamide

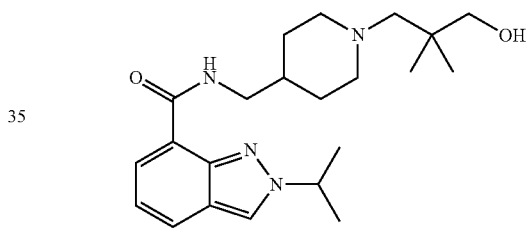

A solution of 2-isopropyl-2H-indazole-7-carboxylic acid (0.075 gram, 0.367 mmol, obtained in the preparation 1) and carbonyldiimidazole (0.072 gram, 0.444 mmol) in DCM (5 mL) was stirred for 3 hours at room temperature. Then added a solution of 3-(4-aminomethyl piperidin-1-yl)-2,2-dimethyl propan-1-ol (0.089 gram, 0.445 mmol, obtained in preparation 6) in DCM (3 mL). The reaction mass was stirred over night (12 hours) at room temperature under nitrogen atmosphere, while monitoring the progress of the reaction by TLC. After completion of the reaction, it was washed with chilled water (2 mL), brine solution (2 mL) and dried over sodium sulphate. The organic phase was concentrated on rotavacuum to obtain the crude residue, which was further purified by flash chromatography using 20% methanolic ammonia: chloroform (2:98) to afford the title compound (0.035 gram). Yield: 24.82%.

1H-NMR (δ ppm): 0.92 (6H s), 1.37-1.45 (2H, m), 1.67-1.69 (8H, m), 1.84-1.87 (2H, m), 2.15-2.21 (2H, m), 2.38 (2H, s), 2.99-3.02 (2H, m), 3.44-3.50 (4H, m), 4.79-4.85 (1H, m), 7.18-7.22 (1H, m), 7.78-7.80 (1H, d), 8.05 (1H, s), 8.23-8.24 (1H, m), 9.40 (1H, bs).

Mass (m/z): 387.4 (M+H)+.

Step (ii): N—[N-(3-hydroxy-2,2-dimethyl propyl) piperidin-4-ylmethyl]-2-isopropyl-2H-indazole-7-carboxamide L(+) Tartarate A solution of L(+)-tartaric acid (0.013 gram, 0.086 mmol) in 1 mL CH3OH was added to a stirred solution of N—[N-(3-hydroxy-2,2-dimethyl propyl) piperidin-4-ylmethyl]-2-isopropyl-2H-indazole-7-carboxamide (0.035 gram, 0.09 mmole, obtained in the above step) in methanol (3 mL). The clear mass, thus obtained, was stirred further for 2 hours at room temperature. The solvent was evaporated to afford solid mass. The solid mass was triturated with diethyl ether (20 mL) and dried under reduced pressure to obtain the title compound (0.038 gram). Yield: 79.16%.

1H-NMR (δ ppm): 1.06 (6H, s), 1.67-1.76 (8H, m), 2.01-2.08 (3H, m), 3.11-3.15 (6H, m), 3.48-3.61 (6H, m), 4.40 (2H, s), 7.19-7.23 (1H, t), 7.93-7.95 (1H, d), 8.07-8.09 (1H, d), 8.45 (1H, s), 9.71 (1H, bs).

Mass (m/z): 387.3 (M+H)+.

Example 7: Preparation of N—[N-(2-fluoroethyl) piperidin-4-yl methyl]-2-isopropyl-2H-indazole-7-carboxamide

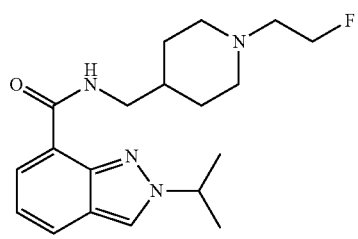 [SMILES: CC(C)n1cc2cccc(C(=O)NCC3CCN(CCF)CC3)c2n1]

A solution of 2-isopropyl-2H-indazole-7-carboxylic acid (0.1 gram, 0.49 mmol, obtained in the preparation 1) and carbonyldiimidazole (0.1 gram, 0.617 mmol) in DCM (5 mL) was stirred for 3 hours at room temperature. Then added a solution of 4-aminomethyl-1-(2-fluoro ethyl) piperidine (0.1 gram, 0.625 mmol, obtained in the preparation 11) in DCM (3 mL). The reaction mass was stirred over night (12 hours) at room temperature under nitrogen atmosphere, while monitoring the progress of the reaction by TLC. After completion of the reaction (TLC), the reaction mass was washed with chilled water (2 mL), brine solution (2 mL) and dried over Na2SO4. The organic phase was concentrated on rotavacuum to obtain the crude residue, which was further purified by flash chromatography using 20% methanolic NH3: CHCl3 (2:98) to afford the title compound (0.035 gram). Yield: 24.82%.

1H-NMR (δ ppm): 1.41-1.55 (2H, m), 1.66-1.67 (7H, m), 1.86-1.89 (2H, m), 2.08-2.14 (2H, t), 2.66-2.68 (1H, t), 2.73-2.78 (1H, t), 3.00-3.03 (2H, d), 3.47-3.51 (2H, t), 4.50-4.52 (1H, t), 4.62-4.64 (1H, t), 4.77-4.83 (1H, m), 7.16-7.20 (1H, m), 7.77-7.79 (1H, m), 8.05 (1H, s), 8.21-8.23 (1H, m), 9.43 (1H, bs).

Mass (m/z): 347.2 (M+H)+.

Example 8: Preparation of N—[N-benzyl morpholin-2-yl methyl]-2-isopropyl-2H-indazole-7-carboxamide fumarate

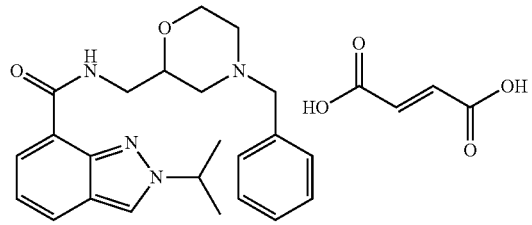

Step (i): Preparation of N—[N-benzyl morpholin-2-yl methyl]-2-isopropyl-2H-indazole-7-carboxamide

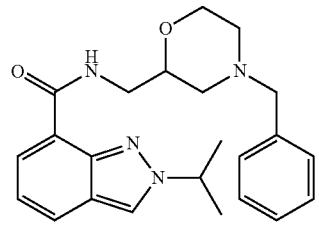 [SMILES: CC(C)n1cc2cccc(C(=O)NCC3CN(Cc4ccccc4)CCO3)c2n1]

To the stirred solution of 2-isopropyl-2H-indazole-7-carboxylic acid (101.2 mg, 0.50 mmol, obtained in preparation 1) in DCM (5.0 mL) cooled at 0° C., DIPEA (0.13 mL, 0.74 mmol), 2-aminomethyl-N-benzyl morpholine (102.2 mg, 0.5 mmol, obtained in the preparation 12) and TBTU (175.1 mg, 0.60 mmol) were added. The reaction mixture was gradually warmed to room temperature and stirred for 16 hours. The reaction mass was diluted with DCM and water and the two layers were separated. The organic layer was dried with anhydrous Na2SO4 and the solvent was removed under reduced pressure. The crude mass thus obtained was purified by silica gel column chromatography which afforded above titled compound (158.3 mg). Yield: 81%.

1H-NMR CDCl3 (δ ppm): 1.69 (d, J=6.6 Hz, 6H), 2.07-2.13 (1H, m), 2.13-2.28 (1H, m), 2.64-2.70 (1H, m), 2.85-2.92 (1H, m), 3.45-3.60 (3H, m), 3.70-3.90 (3H, m), 3.90-4.00 (1H, m), 4.75-4.85 (1H, m), 7.19 (1H, t, J=7.9 Hz), 7.25-7.30 (1H, m), 7.30-7.35 (4H, m), 7.80 (1H, d, J=8.2 Hz), 8.04 (1H, s), 8.23 (1H, d, J=6.9 Hz), 9.62 (1H, bs).

Mass (m/z): 393.2 (M+H)+.

Step (ii): Preparation of N—[N-benzyl morpholin-2-yl methyl]-2-isopropyl-2H-indazole-7-carboxamide fumarate To the stirred solution of N—[N-benzyl morpholin-2-yl methyl]-2-isopropyl-2H-indazole-7-carboxamide (158.4 mg, 0.40 mmol, obtained in the above step) in ethanol (2.0 mL) cooled at 0° C., fumaric acid (42.1 mg, 0.36 mmol) was added. The reaction mass was gradually warmed to room temperature and stirred for 1 hour. The volatiles were removed under reduced pressure and the crude mass was triturated several times with solvent ether which afforded the above titled compound as hygroscopic solid (153.8 mg). Yield: 83%.

1H-NMR DMSO-d6 (δ ppm): 1.60 (bs, 6H), 1.93-2.06 (1H, m), 2.08-2.18 (1H, m), 2.58-2.65 (1H, m), 2.73-2.83 (1H, m), 3.35-3.50 (3H, m), 3.50-3.60 (2H, m), 3.60-3.70 (1H, m), 3.80-3.90 (1H, m), 4.83-4.95 (1H, m), 6.60 (2H, s), 7.17 (1H, t, J=7.6 Hz), 7.23-7.30 (1H, m), 7.30-7.40 (4H, m), 7.92 (1H, d, J=8.1 Hz), 7.97 (1H, d, J=6.8 Hz), 8.63 (1H, s), 9.44 (1H, bs), 13.15 (2H, bs).

Mass (m/z): 393.2 (M+H)+.

Example 9: Preparation of N—[(N-tetrahydropyran-4-yl methyl) morpholine-2-yl methyl]-2-isopropyl-2H-indazole-7-carboxamide A solution of 2-isopropyl-2H-indazole-7-carboxylic acid (0.1 gram, 0.49 mmols, obtained in the preparation 1) and CDI (0.105 gram, 0.648 mmole) in DCM (15 mL) was stirred for 2 hours at room temperature. Added a solution of 2-Aminomethyl-4-(tetrahydropyran-4-yl methyl) morpholine (0.115 gram, 0.537 mmol, obtained in the preparation 13) in DCM (3 mL). The reaction mixture was stirred for 10 hours at room temperature. The reaction mixture was diluted with DCM and water. The two layers were separated, the organic layer was washed with brine, dried over anhydrous Na2SO4 and the volatiles were removed under reduced pressure and the crude mass was purified by silica gel column chromatography to obtain the titled compound (0.17 gram). Yield: 86.73%.

1H-NMR (δ ppm): 1.06-1.10 (2H, m), 1.59-1.61 (7H, m), 1.70-2.13 (5H, m), 2.54-2.60 (1H, m), 2.69-2.72 (1H, m), 3.21-3.81 (10H, m), 4.87-4.93 (1H, m), 7.15-7.197 (1H, m), 7.91-7.97 (2H, m), 8.64 (1H, s) 9.44-9.46 (1H, t).

Mass (m/z): 401.4 (M+H)+.

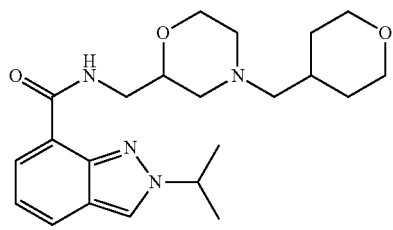 [SMILES: CC(C)n1cc2cccc(C(=O)NCC3CN(CC4CCOCC4)CCO3)c2n1]

Examples 10 to 25

The compounds of Examples 10 to 25 were prepared by following the experimental procedure as described in the Examples 1 to 9 given above, with some noncritical variations.

| Example Number | Chemical name and Structure | Characterization data |
|---|---|---|
| 10. | N-[N-(tetrahydropyran-4-yl methyl)-3-aza bicyclo[3.1.0]hexane-6-yl methyl]-2-isopropyl-2H-indazole-7-carboxamide | 1H-NMR DMSO-d6 (δ ppm): 1.03-1.21 (2H, m), 1.52-1.60 (3H, m), 1.59 (6H, d, J = 6.5 Hz), 1.68-1.82 (3H, m), 2.72-2.88 (2H, m), 3.03-3.15 (2H, m), 3.21 (2H, t, J = 11.1 Hz), 3.32 (2H, t, J = 6.0 Hz), 3.40-3.60 (2H, m), 3.73-3.81 (2H, m), 4.82-4.95 (1H, m), 7.16 (1H, t, J = 7.6 Hz,), 7.92 (1H, d, J = 8.2 Hz), 7.96 (1H, d, J = 6.9 Hz,), 8.64 (1H, s), 9.27 (1H, bs). Mass (m/z): 397.3 (M + H)+. |
| 11. | N-[N-(1-hydroxy cyclopentylmethyl) piperidin-4-yl methyl]-2-isopropyl-2H-indazole-7-carboxamide L(+) tartarate | 1H-NMR (δ ppm): 1.53-1.59 (12H, m), 1.65-1.73 (3H, m), 1.78-1.84 (2H, m), 2.55-2.65 (1H, m), 2.71-2.79 (2H, m), 3.15 (1H, s), 3.20-3.29 (3H, m), 3.36-3.42 (4H, m), 4.04 (2H, m), 4.88-4.94 (1H, m), 7.16-7.20 (1H, m), 7.91-7.97 (2H, m), 8.66 (1H, s) 9.26 (1H, bs). Mass (m/z): 399.7 (M + H)+. |

-continued

| Example Number | Chemical name and Structure | Characterization data |
|---|---|---|
| 12. | N-[N-(tetrahydropyran-4-yl)-3-aza bicyclo[3.1.0]hexane-6-yl methyl]-2-isopropyl-2H-indazole-7-carboxamide | $^1$H-NMR DMSO-$d_6$ (δ ppm): 1.40-1.57 (3H, m,), 1.61 (6H, d, J = 6.5 Hz), 1.75-1.91 (4H, m), 3.05-3.20 (2H, m), 3.21 (2H, t, J = 11.5 Hz,), 3.38 (2H, t, J = 5.7 Hz,), 3.40-3.60 (2H, m), 3.82-3.92 (2H, m), 4.90-5.00 (1H, m), 7.18 (1H, t, J = 7.6 Hz), 7.94 (1H, d, J = 8.2 Hz), 7.98 (1H, d, J = 6.89 Hz), 8.66 (1H, s), 9.28 (1H, bs). Mass (m/z): 383.4 (M + H)$^+$. |
| 13. | N-(N-isopropyl piperidin-4-ylmethyl)-2-isopropyl-2H-indazole-7-carboxamide fumarate | $^1$H-NMR DMSO-$d_6$ (δ ppm): 1.02 (6H, d, J = 6.5 Hz), 1.38-1.52 (2H, m), 1.60 (6H, d, J = 6.6 Hz), 1.65-1.80 (1H, m), 1.80-1.90 (2H, m), 2.45-2.60 (2H, m), 2.96-3.12 (3H, m), 3.36 (2H, t, J = 5.9 Hz), 4.85-5.00 (1H, m), 6.49 (2H, s), 7.18 (1H, t, J = 7.6 Hz), 7.93 (1H, d, J = 8.2 Hz), 7.97 (1H, d, J = 6.9 Hz), 8.65 (1H, s), 9.28 (1H, bs), Mass (m/z): 343.3 (M + H)$^+$. |
| 14. | N-(N-cyclobutyl piperidin-4-yl methyl)-2-isopropyl-2H-indazole-7-carboxamide fumarate | $^1$H-NMR DMSO-$d_6$ (δ ppm): 1.30-1.48 (2H, m), 1.60 (6H, d, J = 6.6 Hz,), 1.55-1.68 (3H, m), 1.70-1.78 (2H, m), 1.78-1.92 (2H, m), 1.92-2.08 (4H, m), 2.82-3.00 (3H, m), 3.36 (2H, t, J = 5.9 Hz), 4.82-5.00 (1H, m), 6.53 (2H, s), 7.18 (1H, t, J = 7.6 Hz), 7.93 (1H, d, J = 8.2 Hz), 7.97 (1H, d, J = 6.9 Hz), 8.65 (1H, s), 9.28 (1H, bs). Mass (m/z): 355.3 (M + H)$^+$. |
| 15. | N-(N-cyclohexyl piperidin-4-yl methyl)-2-isopropyl-2H-indazole-7-carboxamide fumarate | $^1$H-NMR DMSO-$d_6$ (δ ppm): 1.00-1.10 (1H, m), 1.13-1.35 (5H, m), 1.38-1.50 (2H, m), 1.59 (6H, t, J = 6.6 Hz), 1.75-1.90 (7H, m), 2.45-2.70 (3H, m), 3.00-3.12 (2H, m), 3.36 (2H, t, J = 5.9 Hz), 4.85-4.97 (1H, m), 6.50 (2H, s), 7.18 (1H, t, J = 7.6 Hz), 7.93 (1H, d, J = 8.2 Hz), 7.97 (1H, d, J = 7.0 Hz), 8.65 (1H, s), 9.28 (1H, bs). Mass (m/z): 383.5 (M + H)$^+$. |

| Example Number | Chemical name and Structure | Characterization data |
|---|---|---|
| 16. | N-(N-isopropyl-3-aza bicyclo[3.1.0]hexane-6-yl methyl)-2-isopropyl-2H-indazole-7-carboxamide fumarate 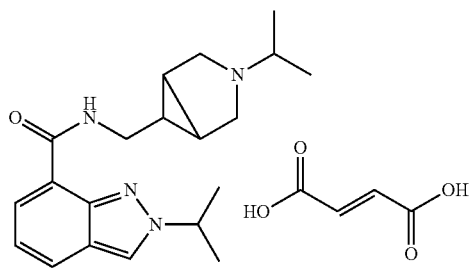 | $^1$H-NMR DMSO-$d_6$ (δ ppm): 1.01 (t, J = 6.5 Hz, 6H), 1.45-1.60 (1H, m), 1.61 (6H, d, J = 6.6 Hz), 2.60-2.80 (2H, m), 3.00-3.65 (7H, m), 4.85-4.98 (1H, m), 6.55 (2H, s), 7.18 (1H, t, J = 7.6 Hz), 7.93 (1H, d, J = 8.2 Hz), 7.97 (1H, d, J = 6.9 Hz), 8.65 (1H, s), 9.27 (1H, bs). Mass (m/z): 341.3 (M + H)$^+$. |
| 17. | N-[N-(4-hydroxy tetrahydro pyran-4-yl methyl)piperidin-4-yl methyl]-2-isopropyl-2H-indazole-7-carboxamide fumarate 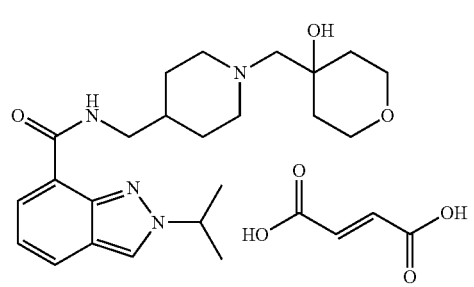 | $^1$H-NMR DMSO-$d_6$ (δ ppm): 1.30-1.50 (4H, m), 1.50-1.65 (9H, m), 1.67-1.78 (2H, m), 2.22-2.35 (2H, m), 2.36 (2H, s), 2.96-3.10 (2H, m), 3.30-3.40 (2H, m), 3.50-3.70 (4H, m), 4.85-5.00 (1H, m), 6.58 (2H, s), 7.18 (1H, t, J = 7.6 Hz), 7.93 (1H, d, J = 8.2 Hz), 7.97 (1H, d, J = 6.9 Hz), 8.65 (1H, s), 9.26 (1H, bs). Mass (m/z): 415.4 (M + H)$^+$. |
| 18. | N-[N-(tetrahydro pyran-4-yl)-3-aza bicyclo[3.1.0]hexane-6-yl methyl]-2-ethyl-2H-indazole-7-carboxamide oxalate 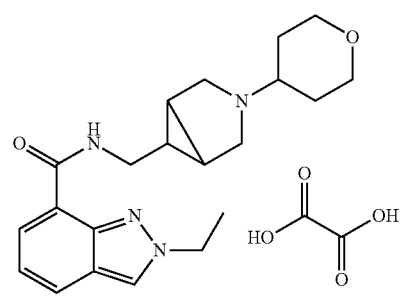 | $^1$H-NMR DMSO-$d_6$ (δ ppm): 1.40-1.55 (3H, m), 1.56 (3H, t, J = 7.2 Hz), 3.75-3.90 (4H, m), 3.00-3.18 (3H, m), 3.21 (2H, t, J = 11.4 Hz), 3.36 (2H, t, J = 6.0 Hz), 3.40-3.58 (2H, m), 3.80-3.90 (2H, m), 4.55 (2H, q), 7.18 (1H, t, J = 7.6 Hz), 7.95 (1H, d, J = 8.2 Hz), 7.98 (1H, d, J = 7.0 Hz), 8.63 (1H, s), 9.24 (1H, bs). Mass (m/z): 369.3 (M + H)$^+$. |

-continued

| Example Number | Chemical name and Structure | Characterization data |
|---|---|---|
| 19. | N-(N-isopropyl piperidine-4-yl)-2-isopropyl-2H-indazole-7-carboxamide fumarate | $^1$H-NMR DMSO-d$_6$ (δ ppm): 1.10 (d, J = 6.6 Hz, 6H), 1.60 (6H, d, J = 6.6 Hz), 1.65-1.80 (2H, m), 2.00-2.10 (2H, m), 2.63-2.75 (2H, m), 2.90-3.10 (3H, m), 4.10-4.12 (1H, m), 4.85-4.95 (1H, m), 6.52 (2H, s), 7.18 (1H, t, J = 7.6 Hz), 7.93 (1H, d, J = 8.2 Hz), 7.98 (1H, d, J = 6.9 Hz), 8.65 (1H, s), 9.33 (1H, d, J = 7.3 Hz). Mass (m/z): 329.3 (M + H)$^+$. |
| 20. | N-(N-cyclopropylmethyl piperidine-4-yl)-2-isopropyl-2H-indazole-7-carboxamide fumarate | $^1$H-NMR DMSO-d$_6$ (δ ppm): 0.10-0.20 (m, 2H), 0.50-0.58 (2H, m), 0.87-1.00 (1H, m), 1.60 (6H, d, J = 6.6 Hz), 1.62-1.80 (2H, m), 2.00-2.10 (2H, m), 2.46 (2H, d, J = 6.7 Hz), 2.58-2.72 (2H, m), 2.95-3.10 (2H, m), 4.00-4.12 (1H, m), 4.86-5.00 (1H, m), 6.56 (2H, s), 7.18 (1H, t, J = 7.6 Hz), 7.94 (1H, d, J = 8.2 Hz), 7.98 (1H, d, J = 7.0 Hz), 8.65 (1H, s), 9.36 (1H, bs). Mass (m/z): 341.3 (M + H)+. |
| 21. | N-(N-cyclobutylmethyl piperidine-4-yl)-2-isopropyl-2H-indazole-7-carboxamide fumarate | $^1$H-NMR DMSO-d$_6$ (δ ppm): 1.60 (6H, d, J = 6.6 Hz), 1.60-1.90 (6H, m), 1.95-2.10 (4H, m), 2.52-2.70 (5H, m), 2.85-3.00 (2H, m), 4.00-4.12 (1H, m), 6.57 (2H, s), 4.85-4.98 (1H, m), 7.18 (1H, t, J = 7.6 Hz), 7.93 (1H, d, J = 8.2 Hz), 7.97 (1H, d, J = 6.9 Hz), 8.65 (1H, s), 9.33 (1H, d, J = 7.0 Hz). Mass (m/z): 355.2 (M + H)+. |
| 22. | N-[(N-tetrahydropyran-4-yl methyl)-4-fluoro piperidin-4-yl methyl]-2-isopropyl-2H-indazole-7-carboxamide | $^1$H-NMR (δ ppm): 1.21-1.28 (4H, m), 1.63-1.65 (2H, m), 1.67-1.69 (6H, d), 1.72-1.75 (1H, m), 1.87-1.96 (2H, m), 2.20-2.22 (2H, m), 2.31-2.36 (2H, m), 2.62-2.65 (2H, m), 3.34-3.40 (2H, m), 3.77-3.84 (2H, m), 3.94-3.96 (2H, m), 4.78-4.84 (1H, m), 7.19-7.23 (1H, m), 7.80-7.82 (1H, m), 8.06 (1H, s), 8.23-8.25 (1H, m), 9.63-9.66 (1H, m); Mass (m/z): 417.4 (M + H)$^+$. |

| Example Number | Chemical name and Structure | Characterization data |
|---|---|---|
| 23. | N-[(N-tetrahydrofuran-3-yl methyl) piperidin-4-yl methyl]-2-isopropyl-2H-indazole-7-carboxamide | ¹H-NMR (δ ppm): 1.43-1.46 (2H, m), 1.67-1.69 (6H, d), 1.70-1.72 (1H, m), 1.82-1.85 (2H, m), 1.94-2.03 (4H, m), 2.30-2.34 (2H, m), 2.44-2.45 (1H, m), 2.89-2.97 (2H, m), 3.47-3.51 (3H, m), 3.72-3.76 (1H, m), 3.80-3.88 (2H, m), 4.76-4.84 (1H, m), 7.18-7.21 (1H, m), 7.78-7.80 (1H, m), 8.05 (1H, s), 8.23-8.25 (1H, m), 9.38-9.41 (1H, m); Mass (m/z): 385.4 (M + H)⁺. |
| 24. | N-[N-(3-methoxy propyl)piperidin-4-yl methyl]-2-isopropyl-2H-indazole-7-carboxamide fumarate | ¹H-NMR DMSO-d₆ (δ ppm): 1.33-1.50 (2H, m), 1.59 (6H, d, J = 6.6 Hz), 1.60-1.86 (5H, m), 2.16-2.30 (2H, m), 2.50-2.60 (2H, m), 3.00-3.12 (2H, m), 3.19 (3H, s), 3.31 (2H, t, J = 6.2 Hz), 3.36 (2H, t, J = 5.9 Hz), 4.85-4.98 (1H, m), 6.53 (2H, s), 7.18 (1H, t, J = 7.6 Hz), 7.93 (1H, d, J = 8.2 Hz), 7.97 (1H, d, J = 7.0 Hz), 8.65 (1H, s), 9.27 (1H, bs). Mass (m/z): 373.4 (M + H)⁺. |
| 25. | N-[N-(2-methoxy ethyl)piperidin-4-yl methyl]-2-isopropyl-2H-indazole-7-carboxamide fumarate | ¹H-NMR (DMSO-d₆ (δ ppm): 1.32-1.48 (2H, m), 1.59 (6H, d, J = 6.6 Hz), 1.60-1.70 (1H, m), 1.73-1.82 (2H, m), 2.12-2.25 (2H, m), 2.60 (2H, t, J = 5.6 Hz), 2.98-3.08 (2H, m), 3.22 (3H, s), 3.35 (2H, t, J = 5.9 Hz), 3.44 (2H, t, J = 5.6 Hz), 4.85-4.98 (1H, m), 6.56 (2H, s), 7.18 (1H, t, J = 7.6 Hz), 7.93 (1H, d, J = 8.2 Hz), 7.97 (1H, d, J = 7.0 Hz), 8.65 (1H, s), 9.28 (1H, bs), Mass (m/z): 359.3 (M + H)⁺. |

Example 26: Preparation of N—[(N-tetrahydropyran-4-yl methyl)-4-hydroxy piperidin-4-yl methyl]-2-isopropyl-2H-indazole-7-carboxamide fumarate

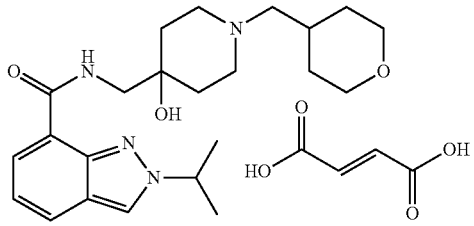

Step (i): Preparation of N-[(1-tert-butyloxy carbonyl-4-hydroxy piperidin-4-yl)methyl]-2-isopropyl-2H-indazole-7-carboxamide

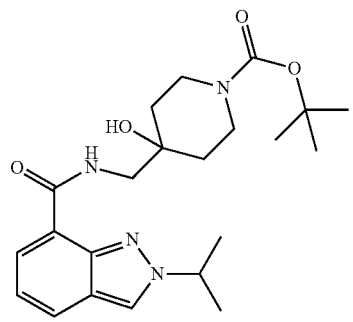 [SMILES: CC(C)n1cc2cccc(C(=O)NCC3(O)CCN(C(=O)OC(C)(C)C)CC3)c2n1]

To a stirred solution of 2-isopropyl-2H-indazole-7-carboxylic acid (0.209 gram, 1.02 mmol, obtained in the preparation 1) in DCM (4 mL) cooled at 0° C. was added DIPEA (0.26 mL, 1.5 mmol) and TBTU (0.35 gram, 1.1 mmol). After stirring for 15 minutes, tert-butyl 4-aminomethyl-4-hydroxy piperidine-1-carboxylate (0.27 gram, 1.18 mmol, obtained in the preparation 4) was added. The reaction mixture was gradually warmed to room temperature and stirred for 16 hours. The reaction mixture was diluted with DCM and water. The two layers were separated, the organic layer was washed with brine, dried over anhydrous Na2SO4 and the volatiles were removed under reduced pressure and the crude mass was purified by silica gel column chromatography to obtain the titled compound (0.41 gram). Yield: 100%

1H-NMR CDCl3 (δ ppm): 1.45 (9H, s), 1.55-1.80 (11H, m), 3.20-3.35 (2H, m), 3.60-3.95 (4H, m), 4.75-4.90 (1H, m), 7.21 (1H, t, J=7.5 Hz), 7.84 (1H, d, J=8.2 Hz), 8.08 (1H, s), 8.23 (1H, d, J=7.0 Hz), 9.57 (1H, bs).

Mass (m/z): 417.4 (M+H)+.

Step (ii): Preparation N-(4-hydroxy piperidin-4-yl methyl)-2-isopropyl-2H-indazole-7-carboxamide hydrochloride

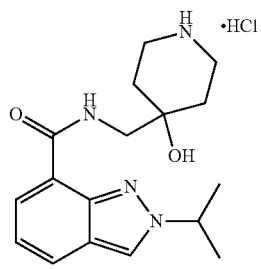 [SMILES: Cl ; CC(C)n1cc2cccc(C(=O)NCC3(O)CCNCC3)c2n1]

To a stirred solution of N-[(1-tert-butyloxy carbonyl-4-hydroxy piperidin-4-yl)methyl]-2-isopropyl-2H-indazole-7-carboxamide (0.55 gram, 1.0 mmol, obtained in the above step) in isopropanol (3 mL) cooled at 0° C., a solution of dry HCl in isopropanol (15% w/v, 4 mL) was added. The reaction was gradually warmed to room temperature and stirred for 12 hours. The volatiles were removed under reduced pressure and the crude product was triturated with hexanes and ether to obtain above titled compound (0.39 gram). Yield: 100% 1H-NMR DMSO-d6 (δ ppm): 1.60 (6H, d, J=6.6 Hz); 1.70-1.90 (4H, m), 2.95-3.20 (4H, m), 3.75 (2H, d, J=6.0 Hz), 4.85-4.98 (1H, m), 7.17 (1H, t, J=7.6 Hz), 7.93 (1H, d, J=8.2 Hz), 7.99 (1H, d, J=7.0 Hz), 8.68 (1H, s), 8.84 (1H, bs), 9.15 (1H, bs), 9.50 (1H, bs).

Mass (m/z): 317.3 (M+H)+.

Step (iii): Preparation of N—[(N-tetrahydropyran-4-yl methyl)-4-hydroxy piperidin-4-yl methyl]-2-isopropyl-2H-indazole-7-carboxamide

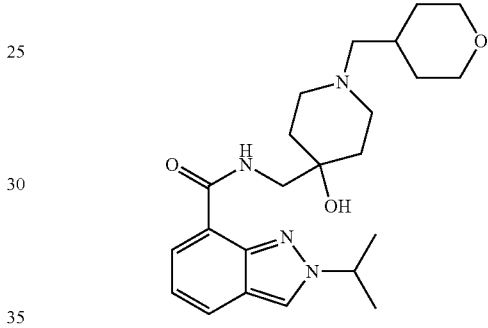

To a stirred solution of N-(4-hydroxy piperidin-4-yl methyl)-2-isopropyl-2H-indazole-7-carboxamide hydrochloride (200.8 mg, 0.56 mmol, obtained in the above step) in DMF at room temperature, K2CO3 (196.5 mg, 1.42 mmols) and 4-(methanesulfonyloxymethyl) tetrahydropyran (144.0 mg, 0.74 mmol) were added. The reaction mixture was heated to 120° C. for 16 hours. After cooling the reaction mass to room temperature, it was diluted with ether and washed with water. The organic layer was dried over anhydrous Na2SO4 and the solvent was removed under reduced pressure. The crude product was purified by silica gel column chromatography which yielded above titled compound (56.0 mg). Yield: 24%.

1H-NMR CDCl3 (δ ppm): 1.20-1.35 (2H, m), 1.60-1.66 (2H, m), 1.69 (6H, d, J=6.6 Hz), 1.70-1.85 (5H, m), 2.20-2.28 (2H, m), 2.32-2.48 (2H, m), 2.52-2.63 (2H, m), 3.37 (2H, t, J=11.4 Hz), 3.64 (2H, d, J=5.9 Hz), 3.90-4.02 (2H, m), 4.78-4.90 (1H, m), 7.17 (1H, t, J=7.4 Hz), 7.83 (1H, d, J=8.2 Hz), 8.07 (1H, s), 8.24 (1H, d, J=7.0 Hz), 9.56 (1H, bs).

Mass (m/z): 415.4 (M+H)+.

Step (iv): Preparation of N—[(N-tetrahydropyran-4-yl methyl)-4-hydroxy piperidin-4-yl methyl]-2-isopropyl-2H-indazole-7-carboxamide fumarate To the stirred solution of N—[(N-tetrahydropyran-4-yl methyl)-4-hydroxy piperidin-4-yl methyl]-2-isopropyl-2H-indazole-7-carboxamide (55.6 mg, 0.13 mmol, obtained in the above step) in ethanol (2.6 mL), fumaric acid (14.8 mg, 0.127 mmol) was added. The reaction mass was stirred for 1 hour at room temperature and the volatiles were removed under reduced pressure to obtain a crude mass which was triturated with ether and filtered which yielded the above titled compound (43.1 mg). Yield: 64%.

1H-NMR DMSO-d6 (δ ppm): 1.00-1.15 (2H, m), 1.55-1.70 (11H, m), 1.70-1.88 (1H, m), 2.27-2.38 (2H, m), 2.42-2.59 (2H, m), 2.60-2.72 (2H, m), 3.25 (2H, t, J=11.3 Hz), 3.43 (2H, d, J=4.3 Hz), 3.80 (2H, d, J=8.6 Hz), 4.64 (1H, bs), 4.83-4.97 (1H, m), 6.56 (2H, s), 7.17 (1H, t, J=7.5 Hz), 7.92 (1H, d, J=8.2 Hz), 7.98 (1H, d, J=7.0 Hz), 8.63 (1H, s), 9.46 (1H, bs)

Mass (m/z): 415.4 (M+H)+.

Example 27

The compound of Example 27 was prepared by following the experimental procedure as described in the Example 26 given above, with some noncritical variations.

1H-NMR CDCl3 (δ ppm): 1.35-1.20 (m, 2H), 1.60-1.66 (2H, m), 1.68 (6H, d, J=6.6 Hz), 1.72-1.88 (6H, m), 2.40-2.52 (4H, m), 2.63-2.75 (2H, m), 3.25 (1H, bs), 3.32 (3H, s), 3.41 (2H, t, J=6.2 Hz), 3.64 (2H, d, J=5.8 Hz), 4.75-4.90 (1H, m), 7.20 (1H, t, J=7.2 Hz), 7.82 (1H, d, J=8.2 Hz), 8.06 (1H, s), 8.23 (1H, d, J=6.9 Hz), 9.57 (1H, bs).

Mass (m/z): 389.3 (M+H)+.

Step (ii): Preparation of N—[N-(3-methoxy propyl)-4-hydroxypiperidin-4-yl methyl]-2-isopropyl-2H-indazole-7-carboxamide fumarate To the stirred solution of N—[N-(3-methoxy propyl)-4-hydroxypiperidin-4-yl methyl]-2-isopropyl-2H-indazole-7-carboxamide (40.1 mg, 0.103 mmol) obtained in the above step) in ethanol (2.0 mL), fumaric acid (11.8 mg, 0.1 mmol) was added. The reaction mass was stirred for 1 hour at room temperature and the volatiles were removed under reduced

| Example Number | Chemical name and Structure | Characterization data |
|---|---|---|
| 27. | N-[(N-tetrahydropyran-4-yl)-4-hydroxy piperidin-4-yl methyl]-2-isopropyl-2H-indazole-7-carboxamide fumarate 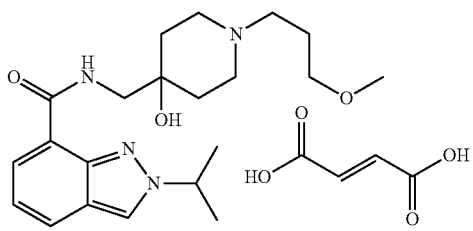 | ¹H-NMR DMSO-d₆ (δ ppm): 1.35-1.57 (2H, m), 1.60 (6H, d, J = 6.4 Hz), 1.60-1.85 (6H, m), 2.65-2.88 (5H, m), 3.25 (2H, t, J = 11.4 Hz), 3.40-3.52 (2H, m), 3.89 (2H, d, J = 8.5 Hz), 4.69 (1H, bs), 4.85-4.98 (1H, m), 6.54 (2H, s), 7.17 (1H, t, J = 7.5 Hz), 7.93 (1H, d, J = 8.2 Hz), 7.98 (1H, d, J = 6.8 Hz), 8.64 (1H, s), 9.48 (1H, bs). Mass (m/z): 401.3 (M + H)⁺. |

Example 28: Preparation of N—[N-(3-methoxy propyl)-4-hydroxypiperidin-4-yl methyl]-2-isopropyl-2H-indazole-7-carboxamide fumarate Step (i): Preparation of N—[N-(3-methoxy propyl)-4-hydroxypiperidin-4-yl methyl]-2-isopropyl-2H-indazole-7-carboxamide To a stirred suspension of N-(4-hydroxy piperidin-4-yl methyl)-2-isopropyl-2H-indazole-7-carboxamide 100.5 mg, 0.28 mmol), obtained in the step (ii) of example 26) in acetonitrile (2.8 mL) at room temperature, cesium carbonate (0.23 grams, 0.71 mmol) and 1-bromo-3-methoxypropane (0.05 mL, 0.43 mmol) were added. The mixture was then heated to reflux for 5 hours. The reaction mass was diluted with water and EtOAc. The two layers were separated; the organic layer was dried over anhydrous Na2SO4 and solvent was removed under reduced pressure. The crude product was purified by silica gel column to obtain the above titled compound (40.1 mg). Yield: 36%.

pressure to obtain a crude mass which was triturated with ether and filtered which yielded the above titled compound (41.4 mg). Yield: 83%.

1H-NMR DMSO-d6+D20 (δ ppm): 1.58 (6H, d, J=6.5 Hz), 1.70-1.90 (6H, m), 2.85-3.00 (2H, m), 3.05-3.18 (2H, m), 3.18 (3H, s), 3.28-3.40 (4H, m), 3.40-3.58 (2H, m), 4.85-4.98 (1H, m), 6.45 (2H, s), 7.18 (1H, t, J=7.5 Hz), 7.93 (1H, d, J=8.2 Hz), 7.97 (1H, d, J=6.8 Hz), 8.60 (1H, s), 9.55 (1H, bs).

Mass (m/z): 389.3 (M+H)+.

Example 29: Preparation of N—[N-(3-Hydroxy-3-methyl butyl) piperidin-4-yl methyl]-2-isopropyl-2H-indazole-7-carboxamide

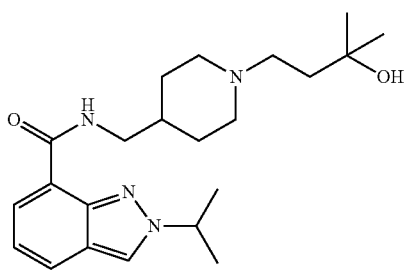 [SMILES: CC(C)n1cc2cccc(C(=O)NCC3CCN(CCC(C)(C)O)CC3)c2n1]

A solution of N-(piperidin-4-yl methyl)-2-isopropyl-2H-indazole-7-carboxamide (0.12 gram, 0.4 mmol, obtained from preparation 8), 4-chloro-2-methyl butan-2-ol (0.059 gram, 0.048 mmol) and K2CO3 (0.11 gram, 0.8 mmol) in DMF (5 mL) was stirred for 48 hours at 120° C., the progress of the reaction was monitored by TLC. After completion of the reaction, it was cooled to room temperature and diluted with cold water (10 mL). The compound was extracted with EtOAc (3×5 mL), the extract was washed with water (5 mL), brine solution (5 mL) and dried over Na2SO4. The organic layer was concentrated on rotavacuum to obtain the crude residue, which was further purified by flash chromatography using a mixture of triethylamine, methanol & chloroform in 0.5:2:97.5 ratio respectively to afford the title compound (0.056 gram). Yield: 36.36%.

1H-NMR (δ ppm): 1.06 (6H, s), 1.22-1.32 (3H, m), 1.48-1.51 (2H, m), 1.57-1.59 (6H, d), 1.69-1.71 (1H, m), 1.73-1.76 (2H, m), 1.84-1.90 (2H, m), 2.36-2.40 (2H, m), 2.89-2.91 (2H, m), 3.15 (1H, s), 4.76-4.80 (1H, m), 4.87-4.94 (1H, m), 7.16-7.19 (1H, m), 7.91-7.93 (1H, m), 7.95-7.97 (1H, m), 8.64 (1H, s), 9.26-9.29 (1H, m).

Mass (m/z): 387.3 (M+H)+.

Example 30: Preparation of N—[N-(2-hydroxy-2-methyl propyl)-4-hydroxy piperidin-4-ylmethyl]-2-isopropyl-2H-indazole-7-carboxamide oxalate

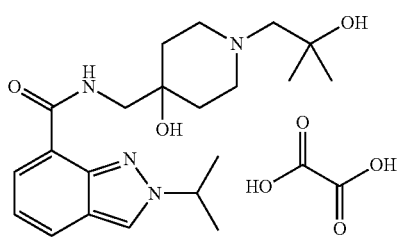

Step (i): Preparation of N—[N-(2-hydroxy-2-methyl propyl)-4-hydroxy piperidin-4-ylmethyl]-2-isopropyl-2H-indazole-7-carboxamide

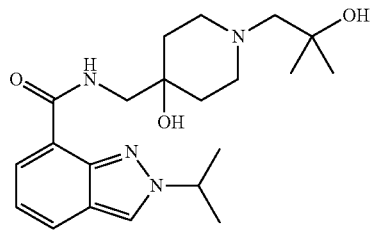 [SMILES: CC(C)n1cc2cccc(C(=O)NCC3(O)CCN(CC(C)(C)O)CC3)c2n1]

To a stirred solution of N-[(4-hydroxy piperidin-4-yl) methyl]-2-isopropyl-2H-indazole-7-carboxamide hydrochloride (200.4 mg, 0.56 mmol, obtained in step (ii) of example 26), triethylamine (0.20 mL, 1.41 mmols) in methanol (4.5 mL) at room temperature, 2,2-dimethyloxirane (0.06 mL, 0.68 mmol) was added and the reaction mass was gradually heated to reflux. After 6 hours at reflux, the reaction mass was concentrated under vacuum to dryness, diluted with DCM (15 mL) and washed with water (2×5 mL). The organic layer was dried over anhydrous Na2SO4 and the solvent was removed under reduced pressure to obtain the titled compound as solid (132.0 mg). Yield: 60%.

1H-NMR CDCl3 (δ ppm): 1.15 (6H, s), 1.69 (6H, d, J=6.6 Hz), 1.69-1.80 (4H, m), 2.35 (2H, s), 2.65-2.80 (4H, m), 3.31 (1H, bs), 3.65 (2H, d, J=6.0 Hz), 4.78-4.90 (1H, m), 7.21 (1H, t, J=7.7 Hz), 7.83 (1H, d, J=8.2 Hz), 8.07 (1H, s), 8.24 (1H, d, J=7.0 Hz), 9.56 (1H, bs).

Mass (m/z): 389.4 (M+H)+.

Step (ii): Preparation of N—[N-(2-hydroxy-2-methyl propyl)-4-hydroxy piperidin-4-ylmethyl]-2-isopropyl-2H-indazole-7-carboxamide oxalate To a stirred solution of N—[N-(2-hydroxy-2-methyl propyl)-4-hydroxy piperidin-4-ylmethyl]-2-isopropyl-2H-indazole-7-carboxamide (131.0 mg, 0.337 mmol, obtained in the above step) in ethanol (3.3 mL) at room temperature, oxalic acid (28.8 mg, 0.32 mmol) was added. The reaction mass was stirred at room temperature for 1 hour and the volatiles were removed under reduced pressure to obtain the crude salt which was triturated with several portion of hexane and ether to obtain a free flowing oxalate salt (106.8 mg). Yield: 73%. 1H-NMR DMSO-d6 (δ ppm): 1.20 (6H, s), 1.60 (6H, d, J=6.6 Hz), 1.65-1.78 (2H, m), 1.90-2.08 (2H, m), 3.00-3.10 (2H, m), 3.10-3.45 (4H, m), 3.47-3.58 (2H, m), 4.85-4.98 (1H, m), 5.10 (1H, bs), 7.18 (1H, t, J=7.6 Hz), 7.94 (1H, d, J=8.0 Hz), 7.99 (1H, d, J=6.7 Hz), 8.66 (1H, s), 9.50 (1H, bs).

Mass (m/z): 389.3 (M+H)+.

Example 31: Preparation of N—[N-(4-hydroxy tetrahydropyran-4-yl methyl)-4-fluoro piperidin-4-yl methyl]-2-isopropyl-2H-indazole-7-carboxamide L(+) Tartarate

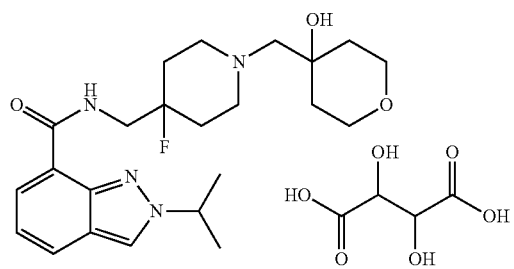

Step (i): Preparation of N—[N-(4-hydroxy tetrahydropyran-4-yl methyl)-4-fluoro piperidin-4-yl methyl]-2-isopropyl-2H-indazole-7-carboxamide

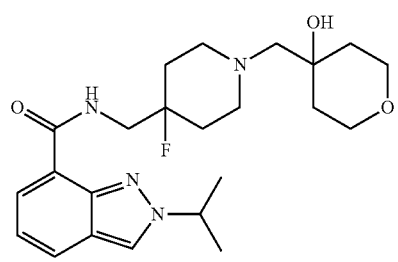 [SMILES: CC(C)n1cc2cccc(C(=O)NCC3(F)CCN(CC4(O)CCOCC4)CC3)c2n1]

A solution of N-(4-fluoro piperidin-4-yl methyl)-2-isopropyl-2H-indazole-7-carboxamide (0.19 gram, 0.596 mmol, obtained in the preparation 7), 1,6-dioxa spiro[2.5] octane (0.145 grams, 1.27 mole) and triethylamine (0.2 grams, 1.19 mmol) in methanol (15 mL) was stirred 7 hours at 78° C., while monitoring the progress of the reaction by TLC. After completion of the reaction, it was concentrated and the crude residual mass, thus obtained, was further purified by flash chromatography using a mixture of methanol, TEA & chloroform in 5:2:93 ratio respectively to afford the title compound (0.114 gram).

Yield: 43.84%.

$^1$H-NMR (δ ppm): 1.14-1.43 (4H, m), 1.54-1.56 (6H, d), 1.80-1.87 (4H, m), 2.43-2.61 (5H, m), 2.89-3.20 (5H, m), 3.68-3.76 (3H, m), 4.89-4.91 (1H, m), 7.18-7.22 (1H, m), 7.92-8.01 (2H, m), 8.69 (1H, s), 9.47 (1H, bs).

Mass (m/z): 433.4 (M+H)$^+$.

Step (ii): Preparation of N—[N-(4-hydroxy tetrahydropyran-4-yl methyl)-4-fluoro piperidin-4-yl methyl]-2-isopropyl-2H-indazole-7-carboxamide L(+) Tartarate A clear solution of L(+)-tartaric acid (0.038 gram, 0.254 mol) in methanol (5.0 mL) was added to a stirred solution of N—[N-(4-hydroxy tetrahydropyran-4-yl methyl)-4-fluoro piperidin-4-yl methyl]-2-isopropyl-2H-indazole-7-carboxamide (0.11 gram, 0.254 mmole, obtained in above step) in methanol (10 mL) at room temperature. The clear mass was stirred further for 2 hours at room temperature. The solvent was evaporated to afford solid mass. The solid mass was further triturated with diethyl ether (2×5 mL) and dried under reduced pressure to obtain the title compound (0.13 gram). Yield: 86.66%.

$^1$H-NMR (δ ppm): 1.12-1.39 (4H, m), 1.56-1.58 (6H, d), 1.82-1.86 (4H, m), 2.42-2.57 (5H, m), 2.84-3.20 (5H, m), 3.66-3.71 (3H, m), 4.23 (2H, s), 4.88-4.89 (1H, m) 7.17-7.20 (1H, m), 7.93-8.00 (2H, m), 8.66 (1H, s), 9.47 (1H, bs).

Mass (m/z): 433.4 (M+H)$^+$.

Example 32: Preparation of N—[N-(2-hydroxy-2-methyl propyl) piperidin-4-yl methyl]-2-isopropyl-2H-indazole-7-carboxamide L(+) Tartarate

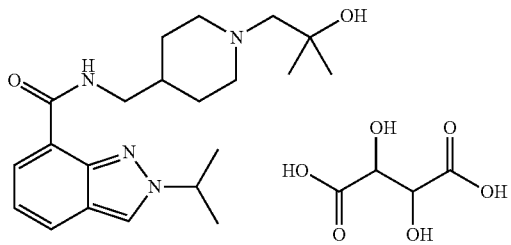 [SMILES: CC(C)n1cc2cccc(C(=O)NCC3CCN(CC(C)(C)O)CC3)c2n1 ; O=C(O)C(O)C(O)C(=O)O]

Step (i): Preparation of N—[N-(2-hydroxy-2-methyl propyl) piperidin-4-yl methyl]-2-isopropyl-2H-indazole-7-carboxamide

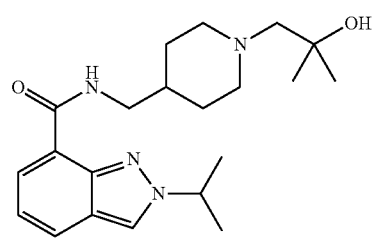 [SMILES: CC(C)n1cc2cccc(C(=O)NCC3CCN(CC(C)(C)O)CC3)c2n1]

A solution of N-(piperidin-4-yl methyl)-2-isopropyl-2H-indazole-7-carboxamide (0.25 gram, 0.833 mmol, obtained in the preparation 8), isobutyleneoxide (0.18 gram, 2.49 mmol) and TEA (0.25 gram, 2.49 mmol) in methanol (10 mL) was stirred for 7 hours at 78° C., while monitoring the progress of the reaction by TLC. After completion of the reaction, it was concentrated and the crude residual mass, thus obtained, was further purified by flash chromatography using a mixture of ammonical methanol (14% w/v) & chloroform in 1:99 ratio to afford the title compound (0.26 grams).

Yield: 83.87%.

$^1$H-NMR (δ ppm): 1.05 (6H, s), 1.35-1.69 (11H, m), 2.06-2.15 (2H, m), 2.49 (2H, s), 2.93-2.96 (2H, m), 3.29-3.35 (2H, m), 3.98 (1H, s), 4.89-4.93 (1H, m), 7.16-7.19 (1H, m), 7.91-7.97 (2H, m), 8.65 (1H, s) 9.25-9.28 (1H, t).

Mass (m/z): 373.3 (M+H)$^+$.

Step (ii): Preparation of N—[N-(2-hydroxy-2-methyl propyl) piperidin-4-yl methyl]-2-isopropyl-2H-indazole-7-carboxamide L(+) Tartarate A mixture of L(+)-tartaric acid (0.104 gram, 0.693 mmol), N—[N-(2-hydroxy-2-methyl propyl) piperidin-4-yl methyl]-2-isopropyl-2H-indazole-7-carboxamide (0.26 gram, 0.701 mmol, obtained in the above step) and methanol (15 mL) was stirred for 2 hours at room temperature. The solvent was evaporated to afford solid mass. The solid mass was further triturated with diethyl ether (2×5 mL) and dried under reduced pressure to obtain the title compound (0.34 gram). Yield: 94.4%.

$^1$H-NMR (δ ppm): 1.12 (6H, s), 1.46-1.77 (11H, m), 2.06-2.15 (2H, m), 2.49-2.52 (2H, m), 3.15-3.19 (2H, m), 3.36-3.39 (2H, m), 4.11 (2H, s), 4.88-4.94 (1H, m), 7.16-7.20 (1H, m), 7.91-7.98 (2H, m), 8.66 (1H, s), 9.25-9.28 (1H, t).

Mass (m/z): 373.4 (M+H)$^+$.

Example 33: Preparation of N—[N-(2-Methoxy-2-methyl propyl) piperidin-4-yl methyl]-2-isopropyl-2H-indazole-7-carboxamide

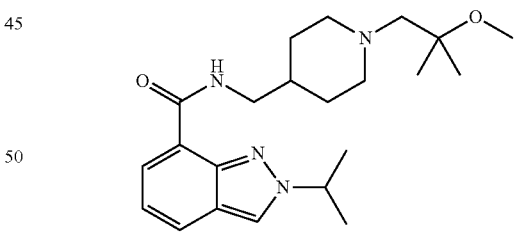

A solution of N-(piperidin-4-yl methyl)-2-isopropyl-2H-indazole-7-carboxamide (0.05 gram, 0.166 mmol, obtained in the preparation 8), 2-methoxy-2-methyl propyl toluene-4-sulfonate (0.065 gram, 0.249 mmol, obtained in the preparation 14), cesium carbonate (0.11 gram, 0.337 mmol) and potassium iodide (0.055 gram, 0.333 mmol) in DMF (5 mL) was stirred for 24 hours at 120° C., the progress of the reaction was monitored by TLC. After completion of the reaction, it was cooled to room temperature and quenched with chilled water (10 mL). The compound was extracted with EtoAc (3×5 mL), the extract was washed with water (5 mL), brine solution (5 mL) and dried over sodium sulphate. The organic layer was concentrated on rotavacuum to obtain the crude residue, which was further purified by flash chromatography using a mixture of TEA, methanol & chloroform in 0.5:2:97.5 ratio respectively to afford the title compound (0.022 gram). Yield: 34.37%.

$^1$H-NMR (δ ppm): 1.16 (6H, s), 1.37-1.48 (2H, m), 1.67-1.69 (8H, m), 1.76-1.79 (2H, m), 2.14-2.20 (2H, m), 2.29 (2H, s), 2.95-2.98 (2H, m), 3.20 (2H, s), 3.47-3.50 (2H, m), 4.77-4.84 (1H, m), 7.18-7.22 (1H, m), 7.78-7.80 (1H, m), 8.05 (1H, s), 8.23-8.25 (1H, m), 9.37 (1H, m).

Mass (m/z): 387.3 (M+H)$^+$.

Example 34: Preparation of N—[N-(2-fluoro-2-methyl propyl) piperidin-4-yl methyl]-2-isopropyl-2H-indazole-7-carboxamide L(+) Tartarate

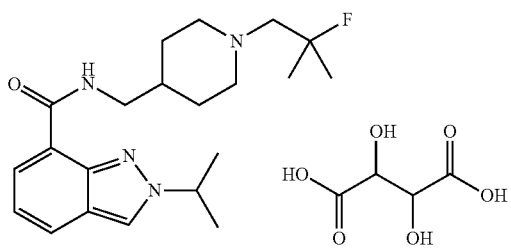 [SMILES: CC(C)n1cc2cccc(C(=O)NCC3CCN(CC(C)(C)F)CC3)c2n1 ; O=C(O)C(O)C(O)C(=O)O]

Step (i): Preparation of N—[N-(2-fluoro-2-methyl propyl) piperidin-4-yl methyl]-2-isopropyl-2H-indazole-7-carboxamide

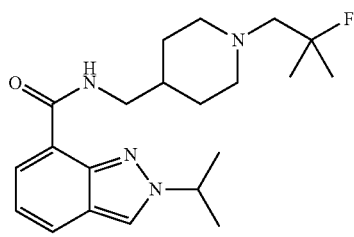 [SMILES: CC(C)n1cc2cccc(C(=O)NCC3CCN(CC(C)(C)F)CC3)c2n1]

Diethylaminosulfur trifluoride (DAST) (0.07 gram, 0.436 mmol) was added to a stirred solution of N—[N-(2-hydroxy-2-methyl propyl) piperidin-4-yl methyl]-2-isopropyl-2H-indazole-7-carboxamide (0.065 gram, 0.174 mmol, obtained from step (i) of example 32) in DCM (2.5 mL) at 0° C. Then reaction mass temperature was slowly raised to room temperature and stirred over night at the same temperature. The progress of the reaction was monitored by thin layer chromatography. After completion of the reaction, it was quenched with chilled water (20 mL). The pH of the mass was adjusted to ~9.5 using aqueous ammonia and the compound was extracted with DCM (3×3 mL). The combined organic phase was washed with water (3 mL), brine solution (3 mL) and dried over Na$_2$SO$_4$. The organic phase was concentrated on rotavacuum to obtain the crude residue, which was further purified by flash chromatography using a mixture of methanolic ammonia (14% w/v) & chloroform in 1:99 ratio respectively to afford the title compound (0.035 gram). Yield: 53.84%.

Step (ii): Preparation of N—[N-(2-fluoro-2-methyl propyl) piperidin-4-yl methyl]-2-isopropyl-2H-indazole-7-carboxamide L(+) Tartarate A mixture of L(+)-tartaric acid (13.6 mg, 0.09 mmol), N—[N-(2-fluoro-2-methyl propyl) piperidin-4-yl methyl]-2-isopropyl-2H-indazole-7-carboxamide (34 mg, 0.09 mmol, obtained in the above step) and methanol (5 mL) was stirred for 2 hours at room temperature. The solvent was evaporated to afford solid mass. The solid mass was further triturated with diethyl ether (2×2 mL) and dried under reduced pressure to obtain the title compound (0.04 gram). Yield: 85.1%.

$^1$H-NMR (δ ppm): 1.22-1.43 (8H, m), 1.57-1.59 (6H, d), 1.70-1.73 (2H, m), 2.13-2.16 (2H, m), 2.42-2.45 (1H, m), 2.94-2.97 (2H, m), 3.32-3.37 (4H, m), 4.26 (2H, s), 4.88-4.94 (1H, m), 7.16-7.20 (1H, m), 7.91-7.97 (2H, m), 8.65 (1H, s) 9.25-9.28 (1H, t).

Mass (m/z): 375.4 (M+H)$^+$.

Example 35: Preparation of N—[N-(2-hydroxy-2-methyl propyl)-4-fluoro piperidin-4-ylmethyl]-2-isopropyl-2H-indazole-7-carboxamide L(+) Tartarate

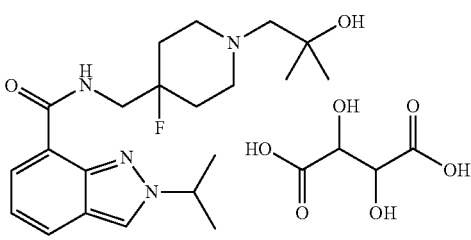

Step (i) Preparation of N—[N-(2-hydroxy-2-methyl propyl)-4-fluoro piperidin-4-ylmethyl]-2-isopropyl-2H-indazole-7-carboxamide

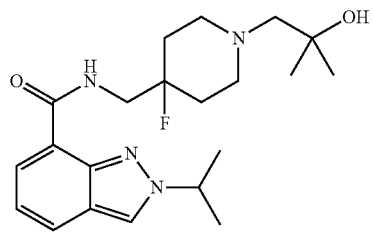 [SMILES: CC(C)n1cc2cccc(C(=O)NCC3(F)CCN(CC(C)(C)O)CC3)c2n1]

A solution of N-(4-fluoro piperidin-4-yl methyl)-2-isopropyl-2H-indazole-7-carboxamide (0.12 gram, 0.376 mmol, obtained in the preparation 7), isobutyleneoxide (0.067 gram, 0.942 mmol) and TEA (0.114 gram, 1.13 mmol) in methanol (10 mL) was stirred 7 hours at 78° C., while monitoring the progress of the reaction by TLC. After completion of the reaction, it was concentrated and the crude residual mass, thus obtained, was further purified by flash chromatography using a mixture of methanol, TEA & chloroform in 4:0.5:95.5 ratio respectively to afford the title compound (0.1 gram). Yield: 68.02%

$^1$H-NMR (δ ppm): 1.03 (6H, s), 1.54-1.56 (6H, d), 1.66-1.75 (4H, m), 2.17 (2H, s), 2.46 (2H, s), 2.69-2.72 (2H, m), 3.33-3.68 (2H, m), 4.01 (1H, s), 4.84-4.90 (1H, m), 7.15-7.18 (1H, m), 7.90-7.97 (2H, m), 8.63 (1H, s), 9.47 (1H, bs).

Mass (m/z): 391.3 (M+H)$^+$.

Step (ii): Preparation of N—[N-(2-hydroxy-2-methyl propyl)-4-fluoro piperidin-4-ylmethyl]-2-isopropyl-2H-indazole-7-carboxamide L(+) Tartarate A mixture of L(+)-tartaric acid (0.039 gram, 0.26 mmol), N—[N-(2-hydroxy-2-methyl propyl)-4-fluoro piperidin-4-ylmethyl]-2-isopropyl-2H-indazole-7-carboxamide (0.1 gram, 0.256 mmol, obtained in the above step) and methanol (5 mL) was stirred for 2 hours at room temperature. The solvent was evaporated to afford solid mass. The solid mass was further triturated with diethyl ether (2×5 mL) and dried under reduced pressure to obtain the title compound (0.13 gram). Yield: 0.13 94.0%

¹H-NMR (δ ppm): 1.06 (6H, s), 1.54-1.56 (6H, d), 1.80-1.84 (5H, m), 2.35-2.54 (4H, m), 2.87-2.94 (2H, m), 3.64-3.81 (2H, m), 4.18 (2H, s), 4.84-4.91 (1H, m) 7.15-7.19 (1H, m), 7.91-7.98 (2H, m), 8.64 (1H, s), 9.45 (1H, bs).

Mass (m/z): 391.3 (M+H)⁺.

Example 36: Preparation of N—[N-(2-hydroxy-2-methyl propyl)-3-aza bicyclo[3.1.0]hexane-6-yl methyl]-2-isopropyl-2H-indazole-7-carboxamide L(+) Tartarate

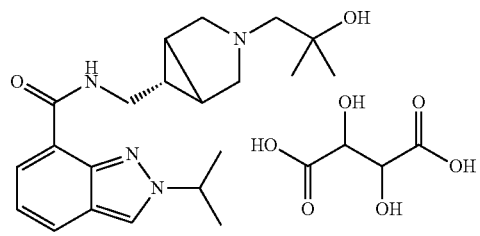

Step (i): Preparation of N—[N-(2-hydroxy-2-methyl propyl)-3-aza bicyclo[3.1.0]hexane-6-yl methyl]-2-isopropyl-2H-indazole-7-carboxamide

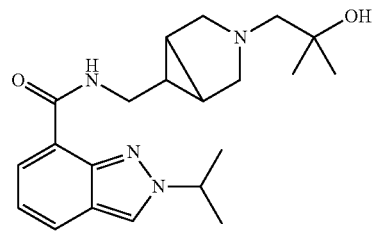 [SMILES: CC(C)n1cc2cccc(C(=O)NCC3C4CN(CC(C)(C)O)CC34)c2n1]

A solution of N-[(3-aza bicyclo[3.1.0]hexane-6-yl) methyl]-2-isopropyl-2H-indazole-7-carboxamide (0.224 gram, 0.75 mmol, obtained in the preparation 9), isobutyleneoxide (0.135 gram, 1.87 mmol) and TEA (0.22 gram, 2.25 mmol) in methanol (10 mL) was stirred 7 hours at 78° C., while monitoring the progress of the reaction by TLC. After completion of the reaction, it was concentrated and the crude residual mass, thus obtained, was further purified by flash chromatography using a mixture of ammonical methanol (14% w/v) & chloroform in 1:99 ratio to afford the title compound. Yield: 53.57%.

¹H-NMR (δ ppm): 1.01 (6H, s), 1.14-1.38 (4H, m), 1.59-1.61 (6H, d), 2.28-2.49 (4H, m), 3.07-3.09 (2H, m), 3.68-3.76 (2H, m), 4.88-4.95 (1H, m), 7.15-7.19 (1H, m), 7.91-7.97 (2H, m), 8.65 (1H, s) 9.30 (1H, bs).

Mass (m/z): 371.3 (M+H)⁺.

Step (ii): Preparation of N—[N-(2-hydroxy-2-methyl propyl)-3-aza bicyclo[3.1.0]hexane-6-yl methyl]-2-isopropyl-2H-indazole-7-carboxamide L(+) Tartarate A mixture of L(+)-tartaric acid (0.03 gram, 0.2 mmol), N—[N-(2-hydroxy-2-methyl propyl)-3-aza bicyclo[3.1.0] hexane-6-yl methyl]-2-isopropyl-2H-indazole-7-carboxamide (0.07 gram, 0.19 mmol, obtained in the above step) and methanol (5 mL) was stirred for 2 hours at room temperature. The solvent was evaporated to afford solid mass. The solid mass was further triturated with diethyl ether (2×5 mL) and dried under reduced pressure to obtain the title compound (0.08 gram). Yield: 81.63%.

¹H-NMR (δ ppm): 1.02 (6H, m), 1.28-1.41 (3H, m), 1.57-1.58 (6H, d), 2.67-2.78 (2H, m), 3.14-3.35 (7H, m), 4.22 (2H, s), 4.86-4.92 (1H, m), 7.13-7.17 (1H, m), 7.89-7.95 (2H, m), 8.63 (1H, s) 9.27 (1H, bs).

Mass (m/z): 371.3 (M+H)⁺.

Example 37: Preparation of 2-isopropyl-7-{5-[1-(3-methoxy propyl) piperidin-4-yl]-[1,3,4]oxadiazol-2-yl)}-2H-indazole fumarate

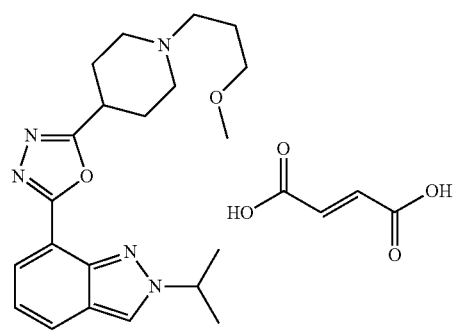

Step (i): Preparation of N'-(2-isopropyl-2H-indazole-7-carbonyl)-1-(3-methoxypropyl) piperidine-4-carboxylic acid hydrazide

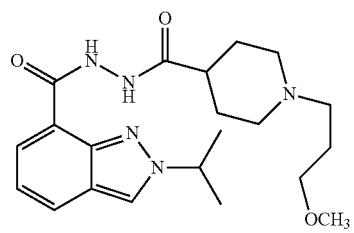 [SMILES: COCCCN1CCC(C(=O)NNC(=O)c2cccc3cn(C(C)C)nc23)CC1]

To a solution of 2-isopropyl-1H-indazole-7-carboxylic acid (50.3 grams, 246 mmol, obtained in the preparation 1) in dichloroethane (350 mL) stirred at room temperature, neat thionyl chloride (35 mL, 486 mmol) was added over a period of 15 minutes. The reaction mixture was then heated to reflux for 2 hours. The volatiles were removed under reduced pressure and the crude acid chloride was cooled to 0° C. before it was redissolved in DCM (250 mL). A solution of 1-(3-methoxypropyl) piperidine-4-carboxylic acid hydrazide (49.8 grams, 231 mmol, obtained in the preparation 10) in DCM (300 mL) was added slowly over a period of 30 minutes to the above acid chloride solution. The reaction was gradually warmed to room temperature and stirred for 1 hour before diluting it with water (500 mL). The two layers were separated and the aqueous layer was once again extracted with DCM (500 mL). The aqueous layer was cooled to 0° C. and basified to pH 9-10 with saturated aqueous NaHCO$_3$ solution (625 mL) then it was extracted with DCM (2×500 mL). The combined organic layer was dried over anhydrous Na$_2$SO$_4$ and the volatiles were removed under reduced pressure to obtain the title product (62.0 grams) as white solid. Yield: 63%.

$^1$H-NMR CDCl$_3$ (δ ppm): 1.73 (6H, d, J=6.5 Hz), 1.75-1.85 (6H, m), 2.00-2.10 (1H, m), 2.30-2.50 (4H, m), 3.00-3.10 (2H, m), 3.33 (3H, s), 3.43 (2H, t, J=6.3 Hz), 4.83-4.92 (1H, m), 7.22 (1H, t, J=7.8 Hz), 7.86 (1H, d, J=8.2 Hz), 8.0 (1H, s), 8.22 (1H, d, J=6.9 Hz), 12.21 (1H, bs).

Mass (m/z): 402.2 (M+H)$^+$.

Step (ii): Preparation of 2-isopropyl-7-{5-[1-(3-methoxy propyl) piperidin-4-yl]-[1,3,4]oxadiazol-2-yl}-2H-indazole

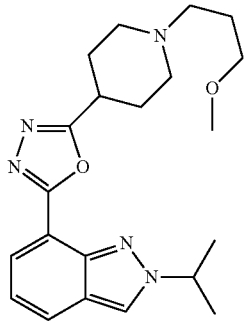 [SMILES: COCCCN1CCC(c2nnc(-c3cccc4cn(C(C)C)nc34)o2)CC1]

Phosphorusoxychloride (POCl$_3$) (8.0 mL) was added to a solution of N'-(2-isopropyl-2H-indazole-7-carbonyl)-1-(3-methoxypropyl) piperidine-4-carboxylic acid hydrazide (2.45 grams, 6.10 mmols, obtained in the preparation 10) in DCM (70 mL) cooled at 0° C. over a period of 15 minutes. The reaction mixture was gradually heated to reflux. After six hours at reflux temperature, the excess POCl$_3$ was distilled off under vacuum. The crude product was cooled to 0° C., diluted with water (20 mL) and extracted with DCM (2×20 mL). The combined organic layer was washed with cold 5% NaOH solution (2×20 mL), dried over anhydrous Na$_2$SO$_4$ and the solvent was removed under reduced pressure to obtain above titled compound (2.0 grams) as an off white solid. Yield: 85%.

$^1$H-NMR CDCl$_3$ (δ ppm): 1.58-1.67 (m, 2H), 1.70 (6H, d, J=6.6 Hz), 1.80-1.95 (2H, m), 2.08-2.20 (2H, m), 2.20-2.38 (2H, m), 2.50-2.65 (2H, m), 3.00-3.10 (2H, m), 3.10-3.20 (1H, m), 3.36 (3H, s), 3.45 (2H, t, J=6.2 Hz), 4.95-5.10 (1H, m), 7.18 (1H, t, J=7.6 Hz), 7.87 (1H, d, J=8.2 Hz), 8.01 (1H, d, J=7.0 Hz), 8.10 (1H, s).

Mass (m/z): 384.3 (M+H)$^+$.

Step (iii): Preparation of 2-isopropyl-7-{5-[1-(3-methoxy propyl) piperidin-4-yl]-[1,3,4]oxadiazol-2-yl}-2H-indazole fumarate To the stirred solution of 2-isopropyl-7-{5-[1-(3-methoxy propyl) piperidin-4-yl]-[1,3,4]oxadiazol-2-yl}-2H-indazole (75.2 mg, 0.196 mmol, obtained in the above step) in ethanol (2.0 mL) cooled at 0° C., fumaric acid (21.6 mg, 0.19 mmol) was added. The reaction mass was gradually warmed to room temperature and stirred for 1 hour. The volatiles were removed under reduced pressure and the crude mass was triturated several times with solvent ether which afforded the above titled compound as hygroscopic solid (80.3 mg). Yield: 86%.

$^1$H-NMR DMSO-d$_6$ (δ ppm): 1.57 (6H, d, J=6.4 Hz), 1.75-1.86 (2H, m), 1.90-2.07 (2H, m), 2.17-2.30 (2H, m), 2.60-2.87 (4H m), 3.21 (3H, s), 3.20-3.32 (3H, m), 3.34 (2H, t, J=6.0 Hz), 4.82-4.95 (m, 1H), 6.54 (2H, s), 7.20 (1H, t, J=7.7 Hz), 7.94 (1H, d, J=7.0 Hz), 7.98 (1H, d, J=8.2 Hz), 8.60 (s, 1H), Mass (m/z): 384.3 (M+H)$^+$.

Examples 38 to 39

The compounds of Examples 38 to 39 were prepared by following the experimental procedure as described in the Example 37 given above, with some noncritical variations.

| Example Number | Chemical name and Structure | Characterization data |
|---|---|---|
| 38. | 2-isopropyl-7-{5-[1-(tetrahydropyran-4-yl methyl)piperidin-4-yl]-[1,3,4]oxadiazol-2-yl}-2H-indazole fumarate | $^1$H-NMR DMSO-d$_6$ (δ ppm): 1.20-1.0 (2H, m), 1.59 (6H, d, J = 6.6 Hz), 1.52-1.65 (2H, m), 1.70-1.92 (3H, m), 2.05-2.12 (2H, m), 2.12-2.33 (4H, m), 2.85-2.98 (2H, m), 3.05-3.18 (1H, m), 3.20-3.40 (4H, m), 3.83 (2H, d, J = 8.3 Hz), 4.82-4.98 (1H, m), 6.60 (2H, s), 7.19 (1H, t, J = 7.6 Hz), 7.93 (1H, d, J = 7.0 Hz), 7.98 (1H, d, J = 8.2 Hz), 8.63 (1H, s), 12.90 (1H, bs). Mass (m/z): 410.2 (M + H)$^+$. |

| Example Number | Chemical name and Structure | Characterization data |
|---|---|---|
| 39. | 2-isopropyl-7-{5-[1-(tetrahydropyran-4-yl)piperidin-4-yl]-[1,3,4]oxadiazol-2-yl}-2H-indazole fumarate 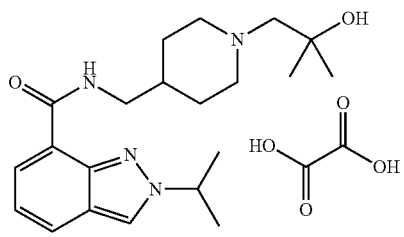 | $^1$H-NMR DMSO-d$_6$ (δ ppm): 1.43-1.57 (2H, m), 1.59 (6H, d, J = 6.6 Hz), 1.67-1.78 (2H, m), 1.80-1.95 (2H, m), 2.08-2.20 (2H, m), 2.60-2.72 (1H, m), 3.00-3.10 (2H, m), 3.10-3.20 (1H, m), 3.20-3.50 (4H, m), 3.85-3.96 (2H, m), 4.85-4.98 (1H, m), 6.59 (2H, s), 7.20 (1H, t, J = 7.6 Hz), 7.94 (1H, d, J = 7.0 Hz), 7.98 (1H, d, J = 8.3 Hz), 8.63 (1H, s), 13.0 (1H, bs). Mass (m/z): 396.2 (M + H)$^+$. |

Example 40: Preparation of N—[N-(2-hydroxy-2-methyl propyl) piperidin-4-yl methyl]-2-isopropyl-2H-indazole-7-carboxamide Oxalate

Step (i): Preparation of N—[N-(2-hydroxy-2-methyl propyl) piperidin-4-yl methyl]-2-isopropyl-2H-indazole-7-carboxamide Oxalate Oxalic acid (0.350 grams, 2.782 mmole) was added to a solution of N—[N-(2-hydroxy-2-methyl propyl) piperidin-4-yl methyl]-2-isopropyl-2H-indazole-7-carboxamide (obtained in step (i) example 32; 1.035 grams, 2.782 mmole) in acetone (10 mL) and stirred for 2 hours at room temperature. The reaction mass was filtered through celite pad, the obtained mass was dried under vacuum to afford the title compound.

Yield: 1.057 gram (82.25%).

$^1$H-NMR (δ ppm): 1.33 (6H s), 1.67-1.69 (6H, d), 1.74-1.83 (2H, m), 1.98-2.07 (3H, m), 3.08-3.21 (4H, m), 3.55-3.58 (2H, t), 3.69-3.71 (2H, bs), 4.91-4.98 (1H, m), 7.19-7.23 (1H, t, J=3.3, 7.8 Hz), 7.93-7.95 (1H, d, J=8.2 Hz), 8.08-8.09 (1H, d, J=7.0 Hz), 8.46 (1H, s), 9.72 (1H, bs);

Mass (m/z): 373.4 (M+H)$^+$.

Step (ii): Recrystallization of N—[N-(2-hydroxy-2-methyl propyl) piperidin-4-yl methyl]-2-isopropyl-2H-indazole-7-carboxamide Oxalate A solution of N—[N-(2-hydroxy-2-methyl propyl) piperidin-4-yl methyl]-2-isopropyl-2H-indazole-7-carboxamide Oxalate (0.40 grams, obtained in the above step) in 5% water in isopropyl alcohol (7.2 mL) was heated at 80° C. under stirring for 30 minutes to obtain a clear solution. The mass was air cooled under stirring to room temperature and then to 10° C. using ice bath. After 15 minutes the solid mass was filtered under vacuum. The solid mass, thus obtained, was dried under vacuum to afford the title compound.

Yield: 0.337 gram (84.25%).

$^1$H-NMR (δ ppm): 1.33 (6H s), 1.67-1.69 (6H, d), 1.72-1.80 (2H, m), 1.96-2.07 (3H, m), 3.06-3.21 (4H, m), 3.52-3.62 (2H, m), 3.64-3.71 (2H, bs), 4.92-4.96 (1H, m), 7.19-7.23 (1H, m), 7.93-7.95 (1H, d, J=8.2 Hz), 8.08-8.09 (1H, d, J=7.0 Hz), 8.46 (1H, s), 9.72 (1H, bs);

Mass (m/z): 373.4 (M+H)$^+$.

Biological Assays

Example 41: Determination of EC$_{50}$ Values for 5-HT$_4$ Receptor

A stable CHO cell line expressing recombinant human 5-HT$_4$ receptor and pCRE-Luc reporter system was used for cell-based assay. The assay offers a non-radioactive based approach to determine binding of a compound to GPCRs. In this specific assay, the level of intracellular cyclic AMP, which is modulated by activation, or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50%.

Using this protocol, compounds described herein were found to exhibit binding affinity towards 5-$HT_4$ receptor. For instance, examples 1, 2, 4, 6, 11, 13, 14, 15, 17, 23, 24, 29, 32, 33, 34 and 40 as described herein, exhibited 5-$HT_4$ receptor agonistic binding in-vitro $EC_{50}$ values of less than or equal to 1 nM; examples 3, 5, 10, 12, 16, 22, 25, 26, 27, 28, 30, 31 and 39 as described herein, exhibited 5-$HT_4$ receptor agonistic binding in-vitro $EC_{50}$ values between 1.1 nM to 5 nM; examples 7, 9, 18, 20, 21, 35, 36, 37 and 38 as described herein, exhibited 5-$HT_4$ receptor agonistic binding in-vitro $EC_{50}$ values between 5.1 nM to 20 nM; examples 8 and 19 as described herein, exhibited 5-$HT_4$ receptor agonistic binding in-vitro $EC_{50}$ values between 20.1 nM to 50 nM.

Example 42: Rodent Pharmacokinetic Study

Male wistar rats (225=25 grams) were used as experimental animals. Three to five animals were housed in each cage. Two days prior to dosing day, male wistar rats (225-250 grams) were anesthetized with isoflurane for surgical placement of jugular vein catheter. Animals were fasted over night before oral dosing (p.o) and food pellets were allowed 2 hours post dosing, whereas during intravenous dosing food and water were provided as ad libitum. Three rats were dosed with compounds of formula (I) (3 mg/kg) orally and intravenously (1 mg/kg).

At each time point blood was collected through jugular vein and immediately replenish with an equivalent volume of normal saline from freely moving rats. Collected blood was transferred into a labeled eppendr off containing 10 μL of heparin as anticoagulant. Typically blood samples were collected as following time points: Pre dose, 0.08 (only i.v.), 0.25, 0.5, 1, 2, 4, 6, 8, and 24 hours post dose (n=3). Blood was centrifuged at 4000 rpm for 10 minutes. Plasma was prepared and stored frozen at −20° C. until analysis. The concentrations of the compounds of formula (I) were quantified in plasma by qualified LC-MS/MS method using suitable extraction technique. The compounds of formula (I) were quantified in the calibration range around 2-2000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using standard non-compartmental model by using WinNonLin 5.0.1 or Phoenix WinNonlin 6.2 version Software package.

| Example Number | Dose (mg/kg) | Vehicle | Route of administration | $C_{max}$ (ng/mL) | $T_{max}$ (h) | $AUC_t$ (ng · hr/mL) | $T_{1/2}$ (h) | Bioavailability (%) |
|---|---|---|---|---|---|---|---|---|
| 1. | 3 | Reagent grade Water | oral (gavage) | 107 ± 22 | 0.42 ± 0.14 | 212 ± 46 | 1.5± 0.0 | 25 ± 5% |
|  | 1 | Water for injection | intravenous (bolus) | — | — | 287 ± 40 | 1.1 ± 0.1 |  |
| 2. | 3 | Reagent grade Water | oral (gavage) | 223 ± 118 | 0.33 ± 0.14 | 190 ± 43 | 1.1 ± 0.6 | 44 ± 10% |
|  | 1 | Water for injection | intravenous (bolus) | — | — | 145 ± 18 | 1.7 ± 0.5 |  |
| 3. | 3 | Reagent grade Water | oral (gavage) | 467 ± 37 | 0.33± 0.14 | 560 ± 117 | 0.8 ± 0.1 | 47 ± 10% |
|  | 1 | Water for injection | intravenous (bolus) | — | — | 397 ± 28 | 0.9± 0.1 |  |
| 32. | 3 | Reagent grade Water | oral (gavage) | 110 ± 8 | 0.50 ± 0.00 | 155 ± 3 | 0.8± 0.0 | 18 ± 0.0% |
|  | 1 | Water for injection | intravenous (bolus) | — | — | 281 ± 6 | 1.2 ± 0.1 |  |

Example 43: Rodent Brain Penetration Study

Male Wistar rats (225±25 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male wistar rats (225-250 grams) were acclimatized. After acclimatization the rats were grouped according to their weight. In each group, 3 animals were kept in individual cage and allowed free access to food and water. At each time point (0.50, 1, and 2 hours) n=3 animals were used.

The compounds of formula (I) were suitably preformulated and administered orally at (free base equivalent) 3 mg/kg. Blood samples were removed via, cardiac puncture by using isoflurane anesthesia. The animals were sacrificed to collect brain tissue. Plasma was separated and brain samples were homogenized and stored frozen at −20° C. until analysis. The concentrations of the compounds of formula (I) in plasma and brain were determined using LC-MS/MS method.

The compounds of formula (I) were quantified in plasma and brain homogenate by qualified LC-MS/MS method using suitable extraction technique. The compounds of formula (I) were quantified in the calibration range of 1-500 ng/mL in plasma and brain homogenate. Study samples were analyzed using calibration samples in the batch and quality control samples spread across the batch. Extent of brain-plasma ratio was calculated ($C_b/C_p$).

| Example Number | Dose (mg/kg) | Vehicle | Route of administration | Single dose Brain Penetration ($C_b/C_p$) |
|---|---|---|---|---|
| 1. | 3 | Reagent grade Water | oral (gavage) | 0.98 ± 0.34 |
|  | 1 | Water for injection | intravenous (bolus) |  |
| 2. | 3 | Reagent grade Water | oral (gavage) | 1.00 ± 0.15 |
|  | 1 | Water for injection | intravenous (bolus) |  |
| 3. | 3 | Reagent grade Water | oral (gavage) | 0.96 ± 0.12 |
|  | 1 | Water for injection | intravenous (bolus) |  |
| 32. | 3 | Reagent grade Water | oral (gavage) | 0.52 ± 0.08 |
|  | 1 | Water for injection | intravenous (bolus) |  |

Example 44: Object Recognition Task Model

The cognition enhancing properties of compounds of this invention were estimated by using this model.

Male Wistar rats (230-280 grams) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cms from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Behaviour Brain Research, 31 (1988), 47-59.

| Example Number | Dose mg/kg, p.o. | Exploration time mean ± S.E.M (sec) | | Inference |
|---|---|---|---|---|
| | | Familiar object | Novel object | |
| 1. | 1 mg/kg, p.o. | 8.51 ± 1.35 | 15.51 ± 1.37 | Active |
| 2. | 0.3 mg/kg, p.o. | 7.21 ± 1.99 | 13.10 ± 1.78 | Active |
| 3. | 1 mg/kg, p.o. | 5.67 ± 1.15 | 14.26 ± 1.64 | Active |
| 32 | 0.3 mg/kg, p.o. | 7.79 ± 1.27 | 17.98 ± 2.41 | Active |

Example 45: Radial Arm Maze

The cognition enhancing properties of compounds of formula (I) of this invention were estimated by using this model.

Radial arm maze consists of a central hub of 45 cm diameter. Each arm was of dimension 42.5×15×24 cm. The maze was elevated to a height of 1 m above the ground. The animals were placed on a restricted diet until they reached approximately 85% of their free feeding weight. During this diet restriction period animals were habituated to the novel feed (pellets). Once the rats reached approximately 85% of their free feeding weight rats were habituated to the maze on the $1^{St}$ and $2^{nd}$ day. The animals that did not eat the pellets were rejected from the study. Animals were randomized on day 2. On the subsequent days the treatment was given as per the allotment. Each animal was introduced into the maze individually for a period of 10 minutes. The arms were baited only once and the animal had to learn the rule that repeated arm entries would not be rewarded. The trial ended once the rat had visited 16 arms or 10 minutes were over or all the pellets were eaten. The arm entries were recorded using the software. Once the trial was over the rat was removed and the maze was cleaned using soap water.

| Example Number | Reversal of Scopolamine Induced amnesia - Effective dose range |
|---|---|
| 2. | 0.3 mg/kg, p.o. |
| 3. | 3 mg/kg, p.o. |
| 32. | 0.3 mg/kg, p.o. |

Example 46: Estimation of Mice Brain Cortical sAPPα Levels

Experimental Procedure

The control group of mice received a subcutaneously (s.c.) sterile water for injection. The treated groups (9 mice per group) received a single s.c. injection of test compound (Example 3) (0.1, 1 and 10 mg/kg in a volume of 5 ml/kg) or Prucalopride (10 mg/kg in a volume of 5 mL/kg) dissolved in sterile water for injection. Mice were killed 60 minutes after the drug injection by cervical dislocation, the brains were quickly isolated and the cortex was dissected at −20° C. The cortex was immediately put in dry ice and weighed before being stored at −80° C. until ELISA was performed.

Sample Preparation:

1. Brain tissues will be thawed and added 4 times volume (0.8 mL/200 mg tissues) of Tris Buffer Saline containing protease inhibitors (TBS).

2. Brian tissue samples homogenized using glass-Teflon homogenizer at 10 strokes. The resulting homogenates centrifuged at 15,000 rpm 4° C. for 60 minutes.
3. The supernatant was discarded and to the precipitate added 4 times volume (0.8 mL/200 mg tissues) of Tris Buffer Saline containing protease inhibitors (TBS). Again homogenized followed by centrifugation at 15,000 rpm 4° C. for 30 minutes.
4. From the above centrifuged mixture the supernatant was discarded and added 10 times volume of 6M Guanidine-HCl in 50 mM Tris buffer pH7.6 (500 µL/50 mg tissues). The resulting solution was sonicated for 5 sec for 4 times.
5. Incubated the above resulting mixture at room temperature for 30 minutes, followed by, centrifugation at 15,000 rpm 4° C. for 30 minutes. Form this taken 5 µL of supernatant solution and diluted with 155 µL of EIA buffer (dilution factor 32).

Measurement of sAPPα by ELISA Kit:

To investigate the role of an acute treatment of 5-HT$_4$ receptor agonists on sAPPα levels, we measured the expression of this protein in homogenates from the cortex of treated and untreated mice by ELISA assay. The entire procedure followed as per ELISA kit manual (Mouse/Rat sAPPα ELISA, Cat No: JP27415, Lot No: ID-118, Exp Date: 2012 Apr. 10, IBL International, Hamburg, Germany).

Statistical Analysis:

Statistical analyses were performed using the Graph Pad Prism (Version 4). Data are Mean±SD of sAPPa levels expressed as percentage of control values (mice which received a water for injection). Values were compared between the different groups by using unpaired t test. The significance level was set at *p<0.05; p<0.01; *p<0.001.

Results (FIG. 1):

The test compound (Example 3) at 0.1 and 10 mg/kg dose levels significantly increased (~25-30%) mice brain cortical sAPPα levels in comparison with control group. The positive control 5-HT4 receptor agonist Prucalopride increased the level of sAPPα in adult mice cortex at 10 mg/kg s.c.

References: Nature Medicine, 14(8), 837-842, 2008; Annual Review of Neuroscience, 17, 489-517, 1994; British Jourl of Pharmacology, 2007, 150, 883-892, 2007.

We claim:

1. A compound of the general formula (I),

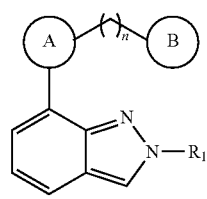

(I)

or a stereoisomer, a pharmaceutically acceptable salt thereof,
wherein,
  $R_1$ is alkyl or cycloalkyl;

Ⓐ is

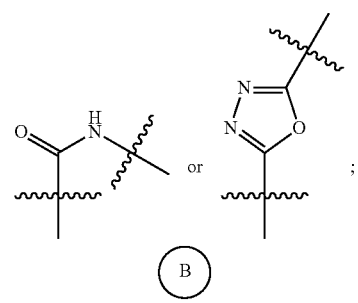

Ⓑ is

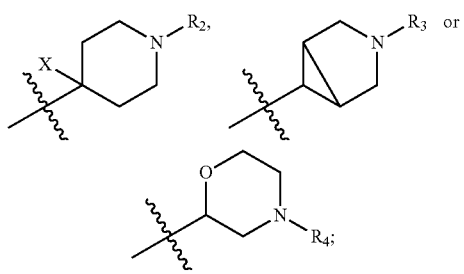

$R_2$ is

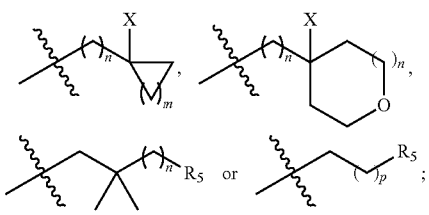

$R_3$ is alkyl,

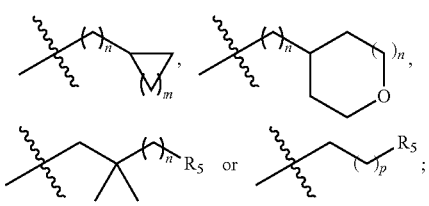

$R_4$ is

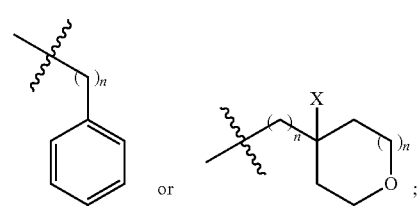

R₅ is fluoro, hydroxy, alkoxy or

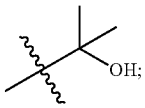 [SMILES: *C(C)(C)O]

X is hydrogen, hydroxy or halogen;
"n" is an integer ranging from 0 to 1, both inclusive;
"m" is an integer ranging from 1 to 4, both inclusive;
"p" is an integer ranging from 0 to 3, both inclusive.

2. The compound as claimed in claim 1, wherein the compound is selected from:

(a) a compound of formula (I):

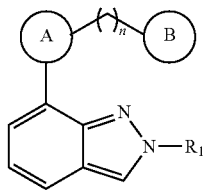

(I)

or a stereoisomer, a pharmaceutically acceptable salt thereof,
wherein,
R₁ is alkyl or cycloalkyl;

is

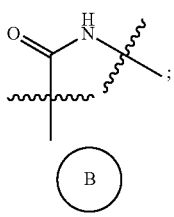

B is

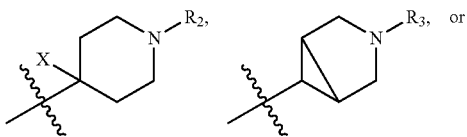

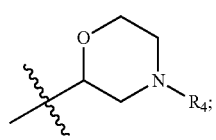

R₂ is

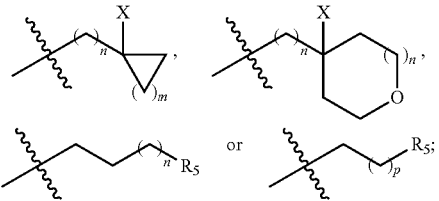

R₃ is alkyl,

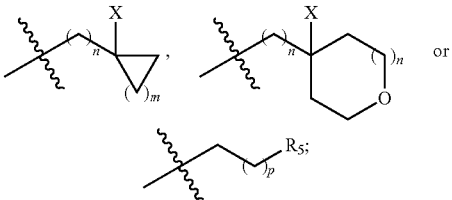

R₄ is

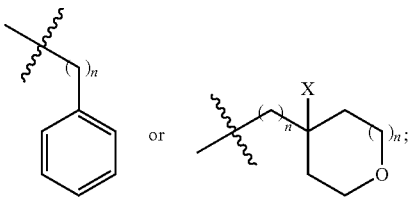

R₅ is fluoro, hydroxy or alkoxy;
X is hydrogen, hydroxy or halogen;
"n" is an integer ranging from 0 to 1, both inclusive;
"m" is an integer ranging from 1 to 4, both inclusive;
"p" is an integer ranging from 0 to 3, both inclusive;

(b) a compound of formula (I):

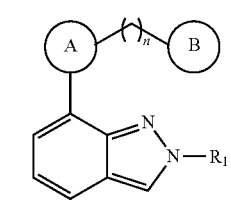

(I)

or a stereoisomer, or a pharmaceutically acceptable salt thereof,
wherein,
R₁ is alkyl or cycloalkyl;

is

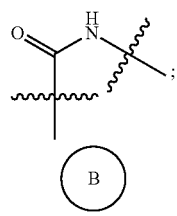

is

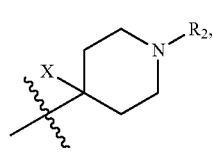

R₂ is

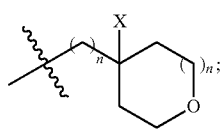

X is hydroxy;
"n" is an integer ranging from 0 to 1, both inclusive;
(c) a compound of formula (I):

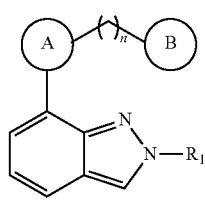

(I)

or a stereoisomer, a pharmaceutically acceptable salt thereof,
wherein,
  R₁ is alkyl;

is

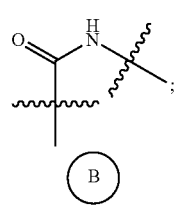

is

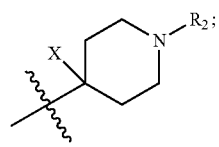

R₂ is

R₅ is alkoxy

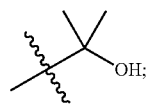 [SMILES: *C(C)(C)O]

X is hydrogen or hydroxy;
"n" is an integer ranging from 0 to 1, both inclusive;
"p" is an integer ranging from 0 to 3, both inclusive;
(d) a compound of formula (I):

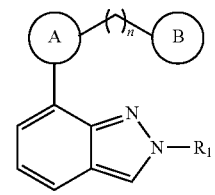

(I)

or a stereoisomer, a pharmaceutically acceptable salt thereof,
wherein,
  R₁ is alkyl;

is

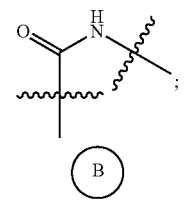

is

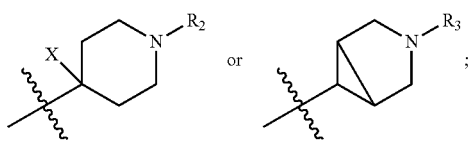

is
R₂ is

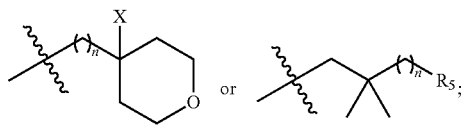

R₃ is

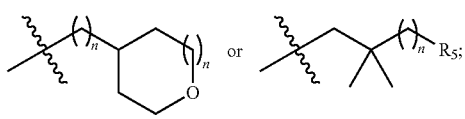

R₅ is fluoro, hydroxy or alkoxy;
X is hydrogen, hydroxy or halogen;
"n" is an integer ranging from 0 to 1, both inclusive;
(e) a compound of formula (I):

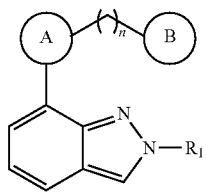

(I)

or a stereoisomer, a pharmaceutically acceptable salt thereof,
wherein,
R₁ is alkyl;

A is

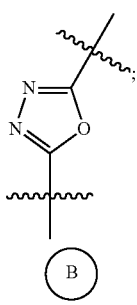

is

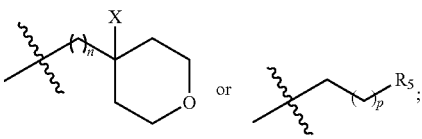

R₂ is (structure) or (structure);

R₅ is alkoxy;
X is hydrogen;
"n" is an integer ranging from 0 to 1, both inclusive;
"p" is an integer ranging from 0 to 3, both inclusive.

3. The compound according to claim 1, which is selected from the group consisting of:
N—[N-(tetrahydropyran-4-yl methyl) piperidin-4-yl methyl]-2-isopropyl-2H-indazole-7-carboxamide fumarate;
N—[N-(tetrahydropyran-4-yl methyl) piperidin-4-yl methyl]-2-ethyl-2H-indazole-7-carboxamide fumarate;
N—[N-(3-methoxy propyl)-3-aza bicyclo[3.1.0]hexane-6-yl methyl]-2-isopropyl-2H-indazole-7-carboxamide oxalate;
N—[N-(3-methoxy propyl) piperidin-4-ylmethyl]-2-ethyl-2H-indazole-7-carboxamide fumarate;
N—[N-(3-methoxy propyl)-3-aza bicyclo[3.1.0]hexane-6-yl methyl]-2-ethyl-2H-indazole-7-carboxamide oxalate;
N—[N-(3-hydroxy-2,2-dimethyl propyl) piperidin-4-yl-methyl]-2-isopropyl-2H-indazole-7-carboxamide L(+) Tartarate;
N—[N-(2-fluoroethyl) piperidin-4-yl methyl]-2-isopropyl-2H-indazole-7-carboxamide;
N—[N-benzyl morpholin-2-yl methyl]-2-isopropyl-2H-indazole-7-carboxamide fumarate;
N—[N-(tetrahydropyran-4-yl methyl) morpholine-2-yl methyl]-2-isopropyl-2H-indazole-7-carboxamide;
N—[N-(tetrahydropyran-4-yl methyl)-3-aza bicyclo[3.1.0]hexane-6-yl methyl]-2-isopropyl-2H-indazole-7-carboxamide;
N—[N-(1-hydroxy cyclopentylmethyl) piperidin-4-yl methyl]-2-isopropyl-2H-indazole-7-carboxamide L(+) tartarate;
N—[N-(tetrahydropyran-4-yl)-3-aza bicyclo[3.1.0]hexane-6-yl methyl]-2-isopropyl-2H-indazole-7-carboxamide;
N—(N-cyclobutyl piperidin-4-yl methyl)-2-isopropyl-2H-indazole-7-carboxamide fumarate;
N—(N-cyclohexyl piperidin-4-yl methyl)-2-isopropyl-2H-indazole-7-carboxamide fumarate;
N—[N-(4-hydroxy tetrahydro pyran-4-yl methyl) piperidin-4-yl methyl]-2-isopropyl-2H-indazole-7-carboxamide fumarate;
N—[N-(tetrahydro pyran-4-yl)-3-aza bicyclo[3.1.0]hexane-6-yl methyl]-2-ethyl-2H-indazole-7-carboxamide oxalate;

N—(N-cyclopropylmethyl piperidine-4-yl)-2-isopropyl-2H-indazole-7-carboxamide fumarate;
N—(N-cyclobutylmethyl piperidine-4-yl)-2-isopropyl-2H-indazole-7-carboxamide fumarate;
N—[N-(tetrahydropyran-4-yl methyl)-4-fluoro piperidin-4-yl methyl]-2-isopropyl-2H-indazole-7-carboxamide;
N—[N-(tetrahydrofuran-3-yl methyl) piperidin-4-yl methyl]-2-isopropyl-2H-indazole-7-carboxamide;
N—[N-(3-methoxy propyl) piperidin-4-yl methyl]-2-isopropyl-2H-indazole-7-carboxamide fumarate;
N—[N-(2-methoxy ethyl) piperidin-4-yl methyl]-2-isopropyl-2H-indazole-7-carboxamide fumarate;
N—[N-(tetrahydropyran-4-yl methyl)-4-hydroxy piperidin-4-yl methyl]-2-isopropyl-2H-indazole-7-carboxamide fumarate;
N—[(N-tetrahydropyran-4-yl)-4-hydroxy piperidin-4-yl methyl]-2-isopropyl-2H-indazole-7-carboxamide fumarate;
N—[N-(3-methoxy propyl)-4-hydroxypiperidin-4-yl methyl]-2-isopropyl-2H-indazole-7-carboxamide fumarate;
N—[N-(3-Hydroxy-3-methyl butyl) piperidin-4-yl methyl]-2-isopropyl-2H-indazole-7-carboxamide;
N—[N-(2-hydroxy-2-methyl propyl)-4-hydroxy piperidin-4-ylmethyl]-2-isopropyl-2H-indazole-7-carboxamide oxalate;
N—[N-(4-hydroxy tetrahydropyran-4-yl methyl)-4-fluoro piperidin-4-yl methyl]-2-isopropyl-2H-indazole-7-carboxamide L(+) Tartarate;
N—[N-(2-hydroxy-2-methyl propyl) piperidin-4-yl methyl]-2-isopropyl-2H-indazole-7-carboxamide L(+) Tartarate;
N—[N-(2-Methoxy-2-methyl propyl) piperidin-4-yl methyl]-2-isopropyl-2H-indazole-7-carboxamide;
N—[N-(2-fluoro-2-methyl propyl) piperidin-4-yl methyl]-2-isopropyl-2H-indazole-7-carboxamide L(+) Tartarate;
N—[N-(2-hydroxy-2-methyl propyl)-4-fluoro piperidin-4-ylmethyl]-2-isopropyl-2H-indazole-7-carboxamide L(+) Tartarate;
N—[N-(2-hydroxy-2-methyl propyl)-3-aza bicyclo[3.1.0]hexane-6-yl methyl]-2-isopropyl-2H-indazole-7-carboxamide L(+) Tartarate;
2-Isopropyl-7-{5-[1-(3-methoxy propyl) piperidin-4-yl]-[1,3,4]oxadiazol-2-yl}-2H-indazole fumarate;
2-Isopropyl-7-{5-[1-(tetrahydropyran-4-yl methyl) piperidin-4-yl]-[1,3,4]oxadiazol-2-yl}-2H-indazole fumarate;
2-Isopropyl-7-{5-[1-(tetrahydropyran-4-yl) piperidin-4-yl]-[1,3,4]oxadiazol-2-yl}-2H-indazole fumarate;
N—[N-(2-hydroxy-2-methyl propyl) piperidin-4-yl methyl]-2-isopropyl-2H-indazole-7-carboxamide Oxalate;
N—[N-(tetrahydropyran-4-yl methyl) piperidin-4-yl methyl]-2-isopropyl-2H-indazole-7-carboxamide;
N—[N-(tetrahydropyran-4-yl methyl) piperidin-4-yl methyl]-2-ethyl-2H-indazole-7-carboxamide;
N—[N-(3-methoxy propyl)-3-aza bicyclo[3.1.0]hexane-6-yl methyl]-2-isopropyl-2H-indazole-7-carboxamide;
N—[N-(3-methoxy propyl) piperidin-4-ylmethyl]-2-ethyl-2H-indazole-7-carboxamide;
N—[N-(3-methoxy propyl)-3-aza bicyclo[3.1.0]hexane-6-yl methyl]-2-ethyl-2H-indazole-7-carboxamide;
N—[N-(3-hydroxy-2,2-dimethyl propyl) piperidin-4-yl methyl]-2-isopropyl-2H-indazole-7-carboxamide;
N—[N-benzyl morpholin-2-yl methyl]-2-isopropyl-2H-indazole-7-carboxamide;
N—[N-(1-hydroxy cyclopentylmethyl) piperidin-4-yl methyl]-2-isopropyl-2H-indazole-7-carboxamide;
N—(N-isopropyl piperidin-4-ylmethyl)-2-isopropyl-2H-indazole-7-carboxamide;
N—(N-cyclobutyl piperidin-4-yl methyl)-2-isopropyl-2H-indazole-7-carboxamide;
N—(N-cyclohexyl piperidin-4-yl methyl)-2-isopropyl-2H-indazole-7-carboxamide;
N—(N-isopropyl-3-aza bicyclo[3.1.0]hexane-6-yl methyl)-2-isopropyl-2H-indazole-7-carboxamide;
N—[N-(4-hydroxy tetrahydro pyran-4-yl methyl) piperidin-4-yl methyl]-2-isopropyl-2H-indazole-7-carboxamide;
N—[N-(tetrahydro pyran-4-yl)-3-aza bicyclo[3.1.0]hexane-6-yl methyl]-2-ethyl-2H-indazole-7-carboxamide;
N—(N-isopropyl piperidine-4-yl)-2-isopropyl-2H-indazole-7-carboxamide;
N—(N-cyclopropylmethyl piperidine-4-yl)-2-isopropyl-2H-indazole-7-carboxamide;
N—(N-cyclobutylmethyl piperidine-4-yl)-2-isopropyl-2H-indazole-7-carboxamide;
N—[N-(3-methoxy propyl) piperidin-4-yl methyl]-2-isopropyl-2H-indazole-7-carboxamide;
N—[N-(2-methoxy ethyl) piperidin-4-yl methyl]-2-isopropyl-2H-indazole-7-carboxamide;
N—[N-(tetrahydropyran-4-yl methyl)-4-hydroxy piperidin-4-yl methyl]-2-isopropyl-2H-indazole-7-carboxamide;
N—[N-(tetrahydropyran-4-yl)-4-hydroxy piperidin-4-yl methyl]-2-isopropyl-2H-indazole-7-carboxamide;
N—[N-(3-methoxy propyl)-4-hydroxypiperidin-4-yl methyl]-2-isopropyl-2H-indazole-7-carboxamide;
N—[N-(2-hydroxy-2-methyl propyl)-4-hydroxy piperidin-4-ylmethyl]-2-isopropyl-2H-indazole-7-carboxamide;
N—[N-(4-hydroxy tetrahydropyran-4-yl methyl)-4-fluoro piperidin-4-yl methyl]-2-isopropyl-2H-indazole-7-carboxamide;
N—[N-(2-hydroxy-2-methyl propyl) piperidin-4-yl methyl]-2-isopropyl-2H-indazole-7-carboxamide;
N—[N-(2-fluoro-2-methyl propyl) piperidin-4-yl methyl]-2-isopropyl-2H-indazole-7-carboxamide;
N—[N-(2-hydroxy-2-methyl propyl)-4-fluoro piperidin-4-ylmethyl]-2-isopropyl-2H-indazole-7-carboxamide;
N—[N-(2-hydroxy-2-methyl propyl)-3-aza bicyclo[3.1.0]hexane-6-yl methyl]-2-isopropyl-2H-indazole-7-carboxamide;
2-Isopropyl-7-{5-[1-(3-methoxy propyl) piperidin-4-yl]-[1,3,4]oxadiazol-2-yl}-2H-indazole;
2-Isopropyl-7-{5-[1-(tetrahydropyran-4-yl methyl) piperidin-4-yl]-[1,3,4]oxadiazol-2-yl}-2H-indazole; and
2-Isopropyl-7-{5-[1-(tetrahydropyran-4-yl) piperidin-4-yl]-[1,3,4]oxadiazol-2-yl}-2H-indazole;

or a stereoisomer, a pharmaceutically acceptable salt thereof.

4. A pharmaceutical composition comprising a compound according to claim 1 and pharmaceutically acceptable excipients.

5. The pharmaceutical composition according to claim 4, for the treatment of clinical conditions mediated through 5-HT$_4$ receptor agonists selected from Alzheimer's disease, schizophrenia, and depression.

6. A method for the treatment of clinical conditions selected from Alzheimer's disease, schizophrenia, and depression, comprising the step of administering to a patient in need thereof an effective amount of the compound or the pharmaceutically acceptable salt thereof according to claim 1.

7. A method for enhancing cognition in a subject having a clinical condition selected from Alzheimer's disease, schizophrenia, and depression, comprising the step of administering to the subject an effective amount of the compound according to claim 3, or pharmaceutically acceptable salt thereof.

\* \* \* \* \*